(12) United States Patent
Stoessel et al.

(10) Patent No.: US 9,871,213 B2
(45) Date of Patent: Jan. 16, 2018

(54) ORGANIC ELECTROLUMINESCENT DEVICE

(71) Applicant: Merck Patent GmbH, Darmstadt (DE)

(72) Inventors: Philipp Stoessel, Frankfurt am Main (DE); Esther Breuning, Ober-Ramstadt (DE); Arne Buesing, Frankfurt am Main (DE); Amir Hossain Parham, Frankfurt am Main (DE); Holger Heil, Frankfurt am Main (DE); Horst Vestweber, Gilserberg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/186,723

(22) Filed: Jun. 20, 2016

(65) Prior Publication Data

US 2016/0322570 A1   Nov. 3, 2016

Related U.S. Application Data

(62) Division of application No. 14/154,323, filed on Jan. 14, 2014, now Pat. No. 9,403,849, which is a division
(Continued)

(30) Foreign Application Priority Data

May 3, 2005  (EP) ..................................... 05009643

(51) Int. Cl.

| C07F 5/04 | (2006.01) |
|---|---|
| C07F 5/05 | (2006.01) |
| C07F 9/46 | (2006.01) |
| C08G 79/08 | (2006.01) |
| C09B 1/00 | (2006.01) |
| C09B 1/02 | (2006.01) |
| C09B 3/02 | (2006.01) |
| H01L 51/00 | (2006.01) |
| C07F 5/02 | (2006.01) |
| C07F 15/00 | (2006.01) |
| C09K 11/06 | (2006.01) |
| H05B 33/14 | (2006.01) |
| C09B 23/14 | (2006.01) |
| C09B 57/00 | (2006.01) |
| C09B 57/10 | (2006.01) |
| C09B 3/78 | (2006.01) |
| C07F 9/53 | (2006.01) |
| C09K 11/02 | (2006.01) |
| H01L 51/50 | (2006.01) |

(52) U.S. Cl.
CPC ............ *H01L 51/008* (2013.01); *C07F 5/025* (2013.01); *C07F 5/04* (2013.01); *C07F 5/05* (2013.01); *C07F 9/46* (2013.01); *C07F 9/5325* (2013.01); *C07F 15/0033* (2013.01); *C07F 15/0086* (2013.01); *C08G 79/08* (2013.01); *C09B 1/00* (2013.01); *C09B 1/02* (2013.01); *C09B 3/02* (2013.01); *C09B 3/78* (2013.01); *C09B 23/141* (2013.01); *C09B 23/148* (2013.01); *C09B 57/00* (2013.01); *C09B 57/001* (2013.01); *C09B 57/008* (2013.01); *C09B 57/10* (2013.01); *C09K 11/025* (2013.01); *C09K 11/06* (2013.01); *H01L 51/009* (2013.01); *H01L 51/0034* (2013.01); *H01L 51/0035* (2013.01); *H01L 51/0085* (2013.01); *H05B 33/14* (2013.01); *C09K 2211/104* (2013.01); *C09K 2211/107* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/1055* (2013.01); *C09K 2211/1062* (2013.01); *C09K 2211/1096* (2013.01); *C09K 2211/185* (2013.01); *H01L 51/0052* (2013.01); *H01L 51/0059* (2013.01); *H01L 51/5012* (2013.01); *H01L 51/5016* (2013.01); *H01L 51/5048* (2013.01); *H01L 51/5072* (2013.01); *Y02E 10/549* (2013.01)

(58) Field of Classification Search
CPC .... C07F 5/025; C07F 5/04; C07F 5/05; C07F 9/46; C07F 9/5325; C07F 15/0033; C07F 15/0086; C08G 79/08; C09B 1/00; C09B 1/02; C09B 3/02; C09B 3/78; C09B 23/141; C09B 23/148; C09B 57/00; C09B 57/001; C09B 57/008; C09B 57/10
USPC ............................................................ 546/4
See application file for complete search history.

(56) References Cited

U.S. PATENT DOCUMENTS

| 6,287,713 B1 | 9/2001 | Heuer et al. |
|---|---|---|
| 6,911,551 B2 | 6/2005 | Stossel et al. |

(Continued)

FOREIGN PATENT DOCUMENTS

| EP | 1142895 A1 | 10/2001 |
|---|---|---|
| JP | 2000150163 A | 5/2000 |

(Continued)

OTHER PUBLICATIONS

Amann, N., et al., "Electron Injection into DNA: Synthesis and Spectroscopic Properties of Pyrenyl-Modified Oligonucleotides", Chemistry AEuropean Journal, vol. 8, No. 21, (2002), pp. 4877-4883.

(Continued)

*Primary Examiner* — Yevegeny Valenrod
(74) *Attorney, Agent, or Firm* — Drinker Biddle & Reath LLP

(57) ABSTRACT

The present invention relates to the use of aromatic boronic acid or borinic acid derivatives in organic electronic devices, in particular electroluminescent devices.

2 Claims, 1 Drawing Sheet

Related U.S. Application Data of application No. 11/912,939, filed as application No. PCT/EP2006/003150 on Apr. 6, 2006, now Pat. No. 8,674,141.

(56) References Cited

U.S. PATENT DOCUMENTS

| | | | |
|---|---|---|---|
| 7,060,369 | B2 | 6/2006 | Stössel et al. |
| 8,674,141 | B2 | 3/2014 | Stoessel et al. |
| 2002/0019527 | A1 | 2/2002 | Wang et al. |
| 2003/0146443 | A1 | 8/2003 | Yamazaki et al. |
| 2003/0229096 | A1 | 12/2003 | Buettelmann et al. |
| 2004/0147742 | A1 | 7/2004 | Wong et al. |
| 2004/0260090 | A1 | 12/2004 | Treacher et al. |

FOREIGN PATENT DOCUMENTS

| | | | |
|---|---|---|---|
| JP | 2003031368 | | 1/2003 |
| JP | 2003229275 A | | 8/2003 |
| JP | 2004189705 | | 7/2004 |
| WO | WO-02/051850 A1 | | 7/2002 |
| WO | WO-02/052661 A1 | | 7/2002 |
| WO | WO-03/033617 A1 | | 4/2003 |
| WO | WO-2003/095445 A1 | | 11/2003 |
| WO | WO 2004055129 A1 * | 7/2004 | .......... C08G 61/123 |

OTHER PUBLICATIONS

Amann, N., et al., "Preparation of Pyrenyl-Modified Nucleosides via Suzuki-Miyaura Cross-Coupling Reactions", Synlett 2002, No. 5, (2002), pp. 687-691.

Baumgarten, M, et al., "Electronic Decoupling in Ground and Excited States of Asymmetric Biaryls", Journal of Physical Chemistry, vol. 104, No. 6, (2000), pp. 1130-1140.

Beinhoff, M., et al., "Synthesis and Spectroscopic Properties of Arene-Substituted Pyrene Derivatives as Model Compounds for Fluorescent Polarity Probes", European Journal of Organic Chemistry, vol. 2001, No. 20, (2001), pp. 3819-3829.

Finocchiaro, P., et al., "Conformational Dynamics of Alkoxydiarylboranes", Journal of the American Chemical Society, vol. 95, No. 21, (1973), pp. 7029-7036.

International Search Report for PCT/EP2006/003150 dated Jul. 26, 2006.

Modrakowski, C., et al., "Synthesis of Pyrene Containing Building Blocks for Dendrimer Synthesis", Synthesis 2001, vol. 14, (2001), pp. 2143-2155.

Ramsey, B., et al., "A laser desorption ionization mass spectrometry investigation of triarylboranes and tri-9-anthrylborane photolysis products", Journal of Organometallic Chemistry, vol. 690, No. 4, (2005), pp. 962-971.

Yamashita, M., et al., "Synthesis of a Versatile Tridentate Anthracene Ligand and its Application for the Synthesis of Hypervalent Pentacoordinate Boron Compounds (10-B-5)", Angewandte Chemie International Edition, vol. 39, No. 22, (2000), pp. 4055-4058.

Cheung, et al., "Direct Functionalization of the Cyclometalated 2-(2'-pyridyl)phenyl Ligand Bound to Iridium (III)", Journal of Organometallic Chemistry, (2005), vol. 690, No. 12, pp. 2913-2921.

\* cited by examiner

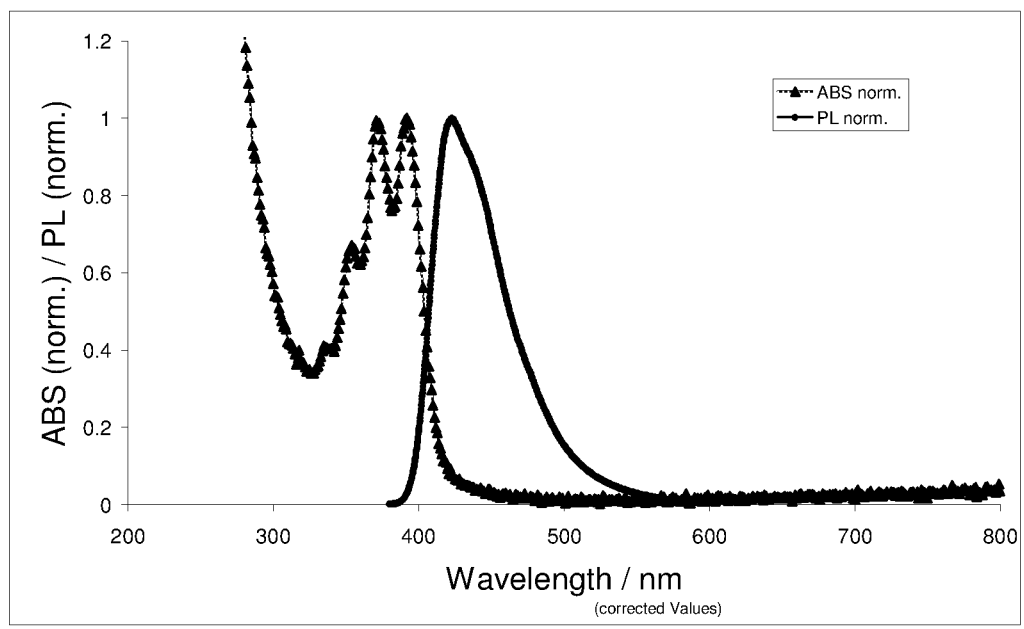
Absorption and photoluminescence spectrum of anthracene-9,10-bis(boronic acid glycol ester).

ORGANIC ELECTROLUMINESCENT DEVICE

CROSS-REFERENCE TO RELATED APPLICATIONS

This application is a divisional of Ser. No. 14/154,323, filed Jan. 14, 2014, which is incorporated by reference. Application Ser. No. 14/154,323 is a divisional of Ser. No. 11/912,939, filed Oct. 29, 2007, which is incorporated by reference. Application Ser. No. 11/912,939 is a national stage application (under 35 U.S.C. §371) of PCT/EP2006/003150, filed Apr. 6, 2006, which claims benefit of European application 05009643.7, filed May 3, 2005. Both of which are incorporated herein by reference in their entirety.

DESCRIPTION

In a number of applications of various types which can be ascribed to the electronics industry in the broadest sense, the use of organic semiconductors as functional materials has been reality for some time or is expected in the near future. The general structure of organic electroluminescent devices described, for example, in U.S. Pat. No. 4,539,507, U.S. Pat. No. 5,151,629, EP 0676461 and WO 98/27136. However, these devices still exhibit considerable problems requiring urgent improvement:
1. The operating lifetime is still short, in particular in the case of blue emission, meaning that it has hitherto only been possible to achieve simple applications commercially.
2. In some cases, use is made of mixtures of isomeric compounds, which may have different physical properties (glass transition temperature, glass formation properties, absorption, photoluminescence). Since these stereoisomers in some cases also have different vapour pressures at the processing temperature, uniform, reproducible production of the organic electronic device is not possible. This problem is described in detail in unpublished application EP 04026402.0.
3. The compounds used are in some cases only sparingly soluble in common organic solvents, which makes their purification during synthesis more difficult, but also makes cleaning of the plants more difficult in the case of the production of the organic electronic devices.
4. Many of the compounds used, in particular those which are used as host materials in fluorescent or phosphorescent devices, are only accessible in multistep syntheses, and purification of the compound is also frequently very complex, which represents a significant disadvantage for use of these compounds.
5. Many of the materials used do not have adequate thermal stability or have a very high evaporation temperature, which is associated with a high thermal load on sensitive equipment parts, such as, for example, the shadow mask. This applies in particular to stilbenamine compounds and to ortho-metallated iridium complexes.

The closest prior art can be regarded as the use of various fused aromatic compounds, in particular anthracene or pyrene derivatives, as host materials in fluorescent OLEDs, in particular for blue-emitting electroluminescent devices, for example 9,10-bis(2-naphthyl)anthracene (U.S. Pat. No. 5,935,721). WO 03/095445 and CN 1362464 describe 9,10-bis(1-naphthyl)anthracene derivatives for use in OLEDs. Further anthracene derivatives which are suitable as host materials are described in WO 01/076323, WO 01/021729, WO 04/013073, WO 04/018588, WO 03/087023 or WO 04/018587. Host materials based on aryl-substituted pyrenes and chrysenes are described in WO 04/016575, which in principle also encompasses corresponding anthracene and phenanthrene derivatives. Although good results have already been achieved using these compounds, it is necessary, for high-quality applications, to have improved host materials available. In addition, some of these compounds are only accessible in a complex manner in multistep syntheses.

In phosphorescent OLEDs, the matrix material used is frequently 4,4'-bis(N-carbazolyl)biphenyl (CBP). The disadvantages are, inter alia, short lifetimes of the devices produced therewith and frequently high operating voltages, which result in low power efficiencies. Furthermore, it has been found that, for energetic reasons, CBP is unsuitable for blue-emitting electroluminescent devices, which results in poor efficiency. In addition, the structure of the devices is complex if CBP is used as matrix material, since a hole-blocking layer and an electron-transport layer additionally have to be used. Improved triplet matrix materials based on keto compounds of spirobifluorene are described in WO 04/093207. However, toxic inorganic cyanides are required in the synthesis of the best of the matrix materials described therein, meaning that the preparation of these materials is ecologically unacceptable.

The electron-transport compound used in organic electroluminescent devices is usually $AlQ_3$ (aluminium trishydroxyquinolinate) (U.S. Pat. No. 4,539,507). This has a number of disadvantages: it cannot be vapour-deposited without a residue since it partially decomposes at the sublimation temperature, which represents a major problem, in particular for production plants. A crucial practical disadvantage is the high hygroscopicity of $AlQ_3$. For use in OLEDs, $AlQ_3$ therefore has to be purified in a complex manner in complicated, multistep sublimation processes and subsequently stored and handled in a protective-gas atmosphere with exclusion of water. In addition, $AlQ_3$ has low electron mobility, which results in higher voltages and thus in lower power efficiency. In order to avoid short circuits in the display, it is desired to increase the layer thickness; this is not possible with $AlQ_3$ owing to the low charge-carrier mobility and the resultant increase in voltage. Furthermore, the inherent colour of $AlQ_3$ (yellow as a solid), which can result in colour shifts in the case of blue OLEDs in particular due to reabsorption and weak re-emission, proves to be very unfavourable. Blue OLEDs can only be produced here with considerable losses in efficiency and colour location impairment. A further disadvantage of $AlQ_3$ is the instability to holes (Z. Popovic et al., *Proceedings of SPIE* 1999, 3797, 310-315), which can always result in problems in the component on long-term use. In spite of the said disadvantages, $AlQ_3$ to date still represents the best compromise for the multifarious requirements of an electron-transport material in OLEDs.

There thus continues to be a demand for improved materials which result in good efficiencies and at the same time long lifetimes in organic electronic devices and which give reproducible results during production and operation of the device and are readily accessible synthetically.

Surprisingly, it has been found that organic electroluminescent devices which comprise aromatic boronic acid or borinic acid derivatives have significant improvements over the prior art. These materials enable an increase in the efficiency and lifetime of the organic electronic device compared with materials in accordance with the prior art. Since these materials cannot exhibit atropisomerism about the aryl-boron bond, which results in diastereomers, reproducible production of the organic electronic devices is thus possible. Furthermore, these materials have the advantage over materials in accordance with the prior art that they are readily accessible using standard methods of organic chemistry and in addition are easy to purify. A particularly surprising observation is that these materials have a relatively low evaporation temperature, in spite of the relatively high molecular weight. The present invention therefore relates to the use of these materials in organic electronic devices.

The use of boron-nitrogen compounds containing tetra-substituted boron is described in the literature (for example US 2005/0048311). These compounds carry a negative charge on the boron and a positive charge on the nitrogen and consequently have completely different electronic properties to boron-nitrogen compounds in which the boron atom is only trisubstituted. The use of boron-nitrogen compounds containing trisubstituted boron, in particular those which also have a boron-carbon bond, is not evident from the description.

Furthermore, WO 02/052661 and WO 02/051850 describe the use of aromatic boranes, i.e. boron compounds which have three boron-aryl bonds, in OLEDs. JP 2003/031368 describes bisboranes in which two substituted borane groups are bridged by an aromatic group, with further aromatic or aliphatic groups being bonded to the boron. These materials are described as electron-transport or hole-blocking materials and as host materials. However, boranes generally have the problem of high chemical reactivity. In particular, these compounds are highly sensitive to oxidation, which makes their synthesis and handling significantly more difficult. Thus, relatively sterically unhindered boranes decompose within only a short time in air (A. Schulz, W. Kaim, *Chem. Ber.* 1989, 122, 1863-1868), and even sterically hindered boranes, such as, for example, mesityl-substituted boranes, are still so sensitive that they have to be handled under a protective gas. This sensitivity significantly restricts the potential use of these compounds.

Arylboronic acid and arylborinic acid derivatives do not have the above-mentioned disadvantages of the boranes or only do so to a significantly reduced extent. Boronic acid and borinic acid derivatives of this type are key intermediates for Suzuki coupling reactions and have to date frequently been employed as starting materials or intermediates for the synthesis of organic semiconductors. However, their use as active component in OLEDs is unknown.

The invention relates to the use of aromatic boronic acid or borinic acid derivatives in organic electronic devices.

Use here is taken to mean that the corresponding compounds are employed directly as active component in the organic electronic device and not as intermediate for the synthesis of further compounds.

The invention furthermore relates to organic electronic devices comprising at least one organic layer which comprises at least one aromatic boronic acid or borinic acid derivative.

The term aromatic boronic acid or borinic acid derivative is taken to mean a compound in which the boron atom is bonded directly to an aromatic or heteroaromatic unit. The boron atom is preferably bonded to a carbon atom of the aromatic or heteroaromatic unit and not to any heteroatom that may be present. For the purposes of this invention, the term aromatic boronic acid or borinic acid derivative is not taken to mean polymers or oligomers in which the boronic acid or borinic acid derivative is only bonded to the chain ends.

For the purposes of this invention, the boron atom in a boronic acid or borinic acid derivative is trisubstituted. Compounds containing tetrasubstituted boron do not fall under the term boronic acid or borinic acid derivative. The boronic acid or borinic acid derivative is preferably a cyclic boronic acid anhydride, a cyclic boronic acid imide, a boronic acid ester, a boronic acid amide, a boronic acid amidoester, a boronic acid nitride, a borinic acid anhydride, a borinic acid imide, a borinic acid ester, a borinic acid amide or a borinic acid nitride. Preference is likewise given to the corresponding sulfur analogues. Oligomeric or polymeric boronic acid anhydrides, boronic acid imides, boronic acid esters or corresponding sulfur compounds are also suitable if they are applied from solution; however, they are less suitable if they are to be applied by sublimation. The use of free boronic acids or borinic acids in organic electronic devices is unsuitable since they tend towards thermal dehydration with formation of boronic or borinic acid anhydrides with liberation of water. The term boronic acid or borinic acid derivative thus does not encompass the free boronic acid or the free borinic acid. However, free boronic acids or borinic acids can be used as starting materials from which the corresponding boronic or borinic acid anhydrides are vapour-deposited in a vapour-deposition process. It is likewise possible to use free boronic acids or borinic acids for the production of the device and not convert them into the corresponding boronic acid or borinic acid derivative until in the device, for example by reaction with another compound in the layer. The general structures of some boronic acid derivatives are shown in scheme 1 below, where Ar generally stands for an aromatic ring system and R for an organic radical.

Scheme 1: Structures of some boronic acid and borinic acid derivatives

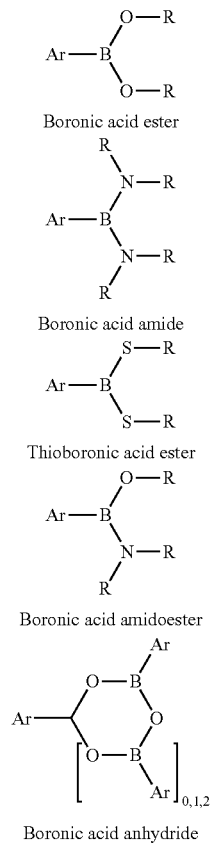

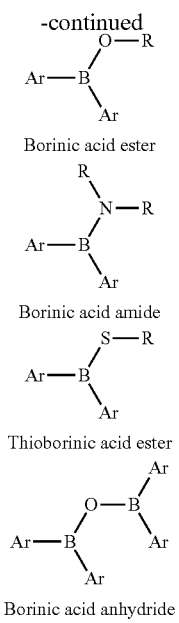

The boronic acid or borinic acid derivative preferably forms glass-like films having a glass transition temperature $T_g$ of above 70° C., particularly preferably above 100° C., very particularly preferably above 130° C.

The boronic acid or borinic acid derivative furthermore preferably has a molecular weight of at least 250 g/mol, particularly preferably at least 300 g/mol, very particularly preferably at least 400 g/mol. The molecular weight of the boronic acid or borinic acid derivative, if it is to be applied by a vapour-deposition process, is furthermore preferably less than 5000 g/mol, particularly preferably less than 2000 g/mol, very particularly preferably less than 1500 g/mol. This is preferably a defined compound.

The organic electronic device is preferably selected from the group consisting of organic and polymeric light-emitting diodes (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photo-receptors and organic laser diodes (O-lasers). Particular preference is given to organic and polymeric light-emitting diodes.

The organic electronic device usually comprises anode, cathode and at least one organic layer which comprises at least one aromatic boronic acid or borinic acid derivative. At least one of the organic layers in organic electroluminescent devices is an emission layer. The emission here can be fluorescence or phosphorescence, or a plurality of different emitters may also be present in one layer or in a plurality of layers, where some of the emitters exhibit fluorescence and the other emitters exhibit phosphorescence. It may also be preferred for the organic electronic device to comprise further layers in addition to the anode, cathode and emission layer. These layers may be, for example: hole-injection layer, hole-transport layer, hole-blocking layer, electron-transport layer and/or electron-injection layer. However, it should be pointed out at this point that each of these layers does not necessarily have to be present.

Thus, in particular on use of boronic acid or borinic acid derivatives in the emission layer, very good results are furthermore achieved if the organic electroluminescent device does not comprise a separate electron-transport layer and/or a separate hole-blocking layer and the emitting layer is directly adjacent to the electron-injection layer or to the cathode. It may likewise be preferred for the organic electroluminescent device not to comprise a separate hole-transport layer and for the emitting layer to be directly adjacent to the hole-injection layer or to the anode.

In a preferred embodiment of the invention, the boronic acid or borinic acid derivative is employed in an emission layer. It can be employed as the pure substance, but is preferably employed as host material in combination with a fluorescent or phosphorescent dopant. In principle, all fluorescent or phosphorescent dopants as described in the literature and mentioned in greater detail below are suitable for this purpose.

In fluorescent devices, the dopant is preferably selected from the class of the monostyrylamines, distyrylamines, tristyrylamines, tetrastyrylamines and arylamines. The term monostyrylamine is taken to mean a compound which contains a styryl group and at least one amine, which is preferably aromatic. The term distyrylamine is taken to mean a compound which contains two styryl groups and at least one amine, which is preferably aromatic. The term tristyrylamine is taken to mean a compound which contains three styryl groups and at least one amine, which is preferably aromatic. The term tetrastyrylamine is taken to mean a compound which contains four styryl groups and at least one amine, which is preferably aromatic. For the purposes of this invention, the term arylamine or aromatic amine is taken to mean a compound which contains three aromatic or heteroaromatic ring systems bonded directly to the nitrogen. For the purposes of this invention, the term styryl group is taken to mean a substituted or unsubstituted vinyl group which is bonded directly to an aryl or heteroaryl group. The styryl groups are particularly preferably stilbenes, which may also be further substituted on the double bond or on the aromatic rings. Suitable substituents here are, in particular, the groups $R^1$ mentioned below. Examples of such dopants are substituted or unsubstituted tristilbenamines or further dopants which are described, for example, in WO 06/000388 and in unpublished patent applications EP 04028407.7 and EP 05001891.0.

The proportion of the boronic acid or borinic acid derivative as host in the fluorescent mixture of the emission layer here is usually between 1 and 99.9% by weight, preferably between 50 and 99.5% by weight, particularly preferably between 80 and 99% by weight, in particular between 90 and 99% by weight. Correspondingly, the proportion of the fluorescent dopant is between 0.1 and 99% by weight, preferably between 0.5 and 50% by weight, particularly preferably between 1 and 20% by weight, in particular between 1 and 10% by weight.

In phosphorescent devices, the dopant is preferably selected from the class of the metal complexes containing at least one element having an atomic number of greater than 20, preferably greater than 38 and less than 84, particularly preferably greater than 56 and less than 80. The phosphorescent emitters used are preferably metal complexes which contain molybdenum, tungsten, rhenium, ruthenium, osmium, rhodium, iridium, palladium, platinum, silver, gold or europium, in particular iridium or platinum.

The ligands on the metal are preferably monoanionic ligands which chelate in a bidentate manner. Suitable for this purpose are, in particular, ligands which form a metal-carbon bond and furthermore a coordinative bond from a donor atom, in particular nitrogen, oxygen or phosphorus, to the metal. The metal complex preferably contains at least one such ligand, particularly preferably at least two such ligands. The formation of a metal-carbon and metal-nitrogen bond is preferred here. The two coordinating groups here may be cyclic, for example phenylpyridine, phenylisoquinoline or derivatives thereof, or they may also be acyclic, for example ligands which bond via pyridine and a vinyl C atom. It is also possible for further ligands to be present, for example β-diketonates, etc. In a particularly preferred embodiment of the invention, the complex contains only ligands which chelate in a bidentate manner and form a metal-carbon bond.

Preferred mixtures comprise, as phosphorescent emitters, at least one compound of the formulae (A) to (D)

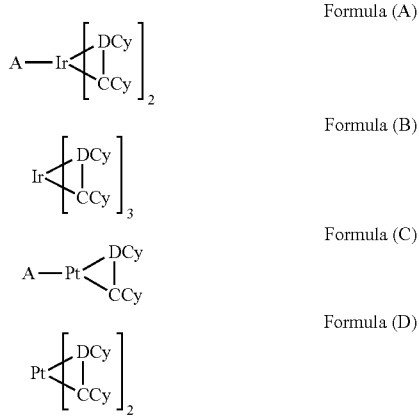

Formula (A)

Formula (B)

Formula (C)

Formula (D)

where the following applies to the symbols and indices used:

DCy is on each occurrence, identically or differently, a cyclic group which contains at least one donor atom, preferably nitrogen or phosphorus, via which the cyclic group is bonded to the metal and which may in turn carry one or more substituents $R^1$; the groups DCy and CCy are bonded to one another via at least one covalent bond;

CCy is on each occurrence, identically or differently, a cyclic group which contains a carbon atom via which the cyclic group is bonded to the metal and which may in turn carry one or more substituents $R^1$;

A is on each occurrence, identically or differently, a monoanionic ligand which chelates in a bidentate manner, preferably a diketonate ligand;

$R^1$ has the same meaning as mentioned below.

The cyclic groups CCy and DCy may be monocyclic or polycyclic and are preferably aromatic or heteroaromatic. The groups CCy and DCy are preferably monocyclic or bicyclic, where the individual rings preferably have 5 or 6 ring atoms, for example benzene, pyridine, naphthalene, quinoline or isoquinoline. Furthermore, a plurality of the ligands may also be linked via one or more substituents $R^1$ as bridging unit to form a relatively large polypodal ligand, and/or a bridge, in particular having 1, 2 or 3 bridge atoms, may be present between CCy and DCy in addition to the direct covalent bond.

Particular preference is given to structures of the formulae (B) and (D) which do not contain a further ligand A.

Examples of phosphorescent emitters are revealed by the applications WO 00/70655, WO 01/41512, WO 02/02714, WO 02/15645, EP 1191613, EP 1191612, EP 1191614, WO 04/081017, WO 05/033244 and the unpublished applications EP 04029182.5 and EP 05002237.5.

The proportion of the boronic acid or borinic acid derivative as host in the phosphorescent mixture is usually between 1 and 99.9% by weight, preferably between 50 and 99.5% by weight, particularly preferably between 70 and 99% by weight, in particular between 80 and 95% by weight. Correspondingly, the proportion of the phosphorescent dopant is between 0.1 and 99% by weight, preferably between 0.5 and 50% by weight, particularly preferably between 1 and 30% by weight, in particular between 5 and 20% by weight.

Preference is furthermore given to organic electroluminescent devices which are characterised in that a plurality of emitting compounds is used in the same layer or a plurality of emitting layers is present, where at least one of the emitting layers comprises at least one boronic acid or borinic acid derivative. This device particularly preferably has a plurality of emission maxima between 380 nm and 750 nm, resulting overall in white emission. The emitting compounds employed here can be both those which exhibit fluorescence and also those which exhibit phosphorescence. An alternative to the production of white emission is the use of broad-band emitters.

In a further preferred embodiment of the invention, the boronic acid or borinic acid derivative is employed as electron-transport material as the pure substance or in a mixture, preferably as the pure substance, in an electron-transport layer in an organic electronic device, in particular in a fluorescent or phosphorescent organic electroluminescent device. The boronic acid or borinic acid derivative here may also be doped, for example with alkali metals.

In a further preferred embodiment of the invention, the boronic acid or borinic acid derivative is employed as hole-blocking material as the pure substance or in a mixture, preferably as the pure substance, in a hole-blocking layer, in particular in a phosphorescent organic electroluminescent device.

In a further preferred embodiment of the invention, the boronic acid or borinic acid derivative is employed as hole-transport material as the pure substance or in a mixture, preferably as the pure substance, in a hole-transport layer or in a hole-injection layer in an organic electronic device, in particular in a fluorescent or phosphorescent organic electroluminescent device. This is the case, in particular, if the boronic acid or borinic acid derivative contains one or more triarylamine groups. The boronic acid or borinic acid derivative here may also be doped, as described, for example, in WO 03/070822.

In a further preferred embodiment of the invention, the boronic acid or borinic acid derivative is employed as fluorescent dopant, preferably in combination with a host material, in an emission layer in a fluorescent organic electroluminescent device. This is the case, in particular, if the boronic acid or borinic acid derivative contains one or more stilbene groups, in particular in combination with one or more triarylamine groups. Suitable host materials here are likewise boronic acid or borinic acid derivatives as already described above. Also suitable are other compounds usually used as host materials, preferably selected from the classes of the oligoarylenes (for example 2,2',7,7'-tetraphenylspirobifluorene in accordance with EP 676461 or dinaphthylanthracene), in particular the oligoarylenes containing fused aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 or WO 05/084082) or the atropisomers (for example in accordance with the unpublished application EP 04026402.0). Particularly preferred host materials are selected from the classes of the oligoarylenes, containing naphthalene, anthracene and/or pyrene or atropisomers of these compounds, the oligoarylenevinylenes, the ketones, the phosphine oxides and the sulfoxides. Very particularly preferred host materials are selected from the classes of the oligoarylenes, containing anthracene and/or pyrene or atropisomers of these compounds, the phosphine oxides and the sulfoxides. The proportion of the boronic acid or borinic acid derivative as dopant in the mixture is preferably as already described above for dopants in fluorescent organic electroluminescent devices.

In a further preferred embodiment of the invention, the boronic acid or borinic acid derivative is employed as phosphorescent dopant, preferably in combination with a host material, in an emission layer in a phosphorescent organic electroluminescent device. Suitable host materials here are likewise boronic acid or borinic acid derivatives as already described above. Also suitable are other compounds usually used as host materials, preferably selected from the classes of the carbazole derivatives, for example 4,4'-bis(N-carbazolyl)biphenyl (CBP), the ketones and imines (for example in accordance with WO 04/093207), the phosphine oxides, sulfoxides and sulfones (for example in accordance with WO 05/003253), the phosphines and sulfides (for example in accordance with WO 05/053051), the tetraarylsilanes (for example in accordance with WO 04/095598) or the oligoarylene derivatives. The phosphorescent dopant according to the invention comprising boronic acid or borinic acid derivatives preferably has the elements and a structure as already described above for phosphorescent emitters, with at least one boronic acid or borinic acid derivative being bonded to at least one ligand. If the ligand is a derivative of phenylpyridine, phenylquinoline or phenylisoquinoline and the boronic acid derivative is a boronic acid ester, this preferably has a cyclic structure. If the boronic acid derivative is a boronic acid ester, this generally preferably has a cyclic structure. Further preferred phosphorescent dopants which carry boronic acid or borinic acid derivative groups are metal/carbene complexes. Simple metal/carbene complexes as are known for use in OLEDs are described, for example, in WO 05/019373.

It may furthermore be preferred for a boronic acid or borinic acid derivative to be used simultaneously in a plurality of layers and/or functions. For example, it can be employed simultaneously both in one or more emission layers and also in one or more electron-transport layers and/or hole-blocking layers and/or hole-transport layers. The boronic acid or borinic acid derivatives in the different layers may be identical or different.

Preference is furthermore given to an organic electronic device which is characterised in that one or more layers are coated using a sublimation process. In this, the materials are vapour-deposited in vacuum sublimation units at a pressure of below $10^{-5}$ mbar, preferably below $10^{-6}$ mbar, particularly preferably below $10^{-7}$ mbar.

Preference is likewise given to an organic electronic device which is characterised in that one or more layers are coated by means of the OVPD (organic vapour phase deposition) process or with the aid of carrier-gas sublimation. The materials are generally applied here at a pressure of between $10^{-5}$ mbar and 1 bar.

Preference is furthermore given to an organic electronic device which is characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing.

In a preferred embodiment of the invention, the boronic acid or borinic acid derivative contains at least one sub-structure of the formula (1)

$$Ar\!-\!B^1\!-\!E \qquad \text{Formula (1)}$$

where the following applies to the symbols used:
$B^1$ stands on each occurrence for a boron atom which is trisubstituted;
Ar is on each occurrence, identically or differently, an aromatic or heteroaromatic ring system having 5 to 40 aromatic ring atoms, which may be substituted by one or more radicals $R^1$;
E is on each occurrence, identically or differently, an oxygen, sulfur or nitrogen atom, to which a further substituent other than hydrogen is bonded in the case of oxygen or sulfur and two further substituents, at least one of which is other than hydrogen, are bonded in the case of nitrogen;
$R^1$ is on each occurrence, identically or differently, F, Cl, Br, I, CN, a straight-chain alkyl, alkoxy or thioalkoxy chain having 1 to 40 C atoms or a branched or cyclic alkyl, alkoxy or thioalkoxy chain having 3 to 40 C atoms, each of which may be substituted by $R^3$ and in which one or more non-adjacent C atoms may be replaced by N—$R^3$, O, S, CO, O—CO—O, CO—O, —$CR^3$=$CR^3$— or —C≡C— and in which one or more H atoms may be replaced by F, Cl, Br, I or CN, or an aromatic or heteroaromatic ring system having 5 to 40 C atoms, which may also be substituted by one or more radicals $R^3$, or a combination of two, three or four of these systems; two or more radicals $R^1$ here may also form a mono- or polycyclic, aliphatic or aromatic ring system with one another;
$R^3$ is on each occurrence, identically or differently, H or an aliphatic or aromatic hydrocarbon radical having 1 to 20 C atoms.

The sub-structure of the formula (1) encompasses both compounds which have precisely one boronic acid or borinic acid derivative bonded to the aromatic ring system and also two or more. Likewise encompassed are compounds in which a plurality of sub-structures Ar—B' are bridged by a plurality of groups E, for example by oligoalcohols, oligothiols or oligoamines. In addition, defined low-molecular-weight compounds and oligomeric, dendritic or polymeric compounds are likewise encompassed. Also encompassed are metal complexes in which the group Ar is bonded to one or more metal atoms.

Preferred boronic acid or borinic acid derivatives are selected from the group of compounds of the formulae (2) to (8), which are explained in greater detail below.

The boronic acid or borinic acid derivative preferably has a structure of the formula (2), formula (3) or formula (4)

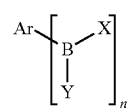

Formula (2)

Formula (3)

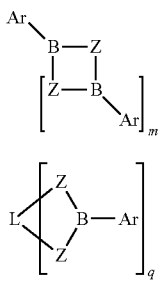

Formula (4)

where Ar, $R^1$ and $R^3$ have the same meaning as described above, and the following applies to the further symbols and indices:

B stands on each occurrence for a boron atom;

X is on each occurrence, identically or differently, a group $OR^2$, $SR^2$, $N(R^2)_2$, $NHR^2$ or $OBAr_2$;

Y is on each occurrence, identically or differently, a group Ar or X;

Z is on each occurrence, identically or differently, O, S, $NR^2$ or NH;

L is on each occurrence, identically or differently, an organic group having 4 to 60 C atoms, to which at least four groups Z are bonded in such a way that they are able, with the boron atom, to form a cyclic system;

$R^2$ is on each occurrence, identically or differently, a straight-chain alkyl chain having 1 to 40 C atoms or a branched or cyclic alkyl chain having 3 to 40 C atoms, each of which may be substituted by $R^3$ and in which one or more non-adjacent C atoms may be replaced by N—$R^3$, O, S, CO, O—CO—O, CO—O, —$CR^3$=$CR^3$— or —C≡C—, with the proviso that a heteroatom is not bonded directly to the oxygen or sulfur or nitrogen of the group X or Y, and in which one or more H atoms may be replaced by F, Cl, Br, I or CN, or an aromatic or heteroaromatic ring system having 5 to 40 C atoms, which may also be substituted by one or more radicals $R^3$, or a combination of two, three or four of these systems; two or more radicals $R^2$ here may also form a mono- or polycyclic, aliphatic or aromatic ring system with one another;

n is on each occurrence, identically or differently, 1, 2, 3, 4, 5 or 6;

m is on each occurrence, identically or differently, 1, 2 or 3;

q is on each occurrence, identically or differently, 2, 3, 4, 5 or 6.

The boronic acid or borinic acid derivative furthermore preferably has a structure of the formula (5), formula (6), formula (7) or formula (8)

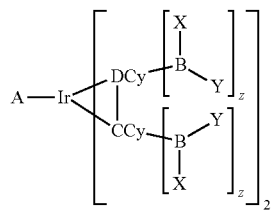

Formula (5)

Formula (6)

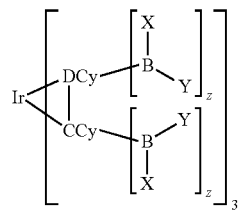

Formula (7)

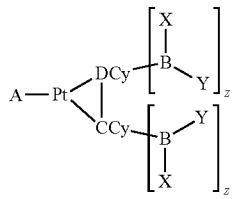

Formula (8)

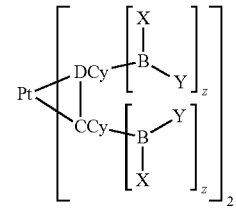

where B, X, Y, Ar, $R^1$, $R^2$ and $R^3$ have the same meaning as described above, and furthermore:

DCy is on each occurrence, identically or differently, a cyclic group which contains at least one donor atom, preferably nitrogen or phosphorus, via which the cyclic group is bonded to the metal and which may in turn carry one or more substituents $R^1$; the groups DCy and CCy are bonded to one another via at least one covalent bond;

CCy is on each occurrence, identically or differently, a cyclic group which contains a carbon atom via which the cyclic group is bonded to the metal and which may in turn carry one or more substituents $R^1$;

A is on each occurrence, identically or differently, a mono-anionic ligand which chelates in a bidentate manner, preferably a diketonate ligand;

z is on each occurrence, identically or differently, 0, 1, 2, 3, 4, 5 or 6, with the proviso that at least one z in each complex is other than 0 and furthermore with the proviso that z cannot adopt a number which is greater than the maximum number of substitutable hydrogen atoms on the corresponding ring DCy or CCy.

The cyclic groups CCy and DCy may be monocyclic or polycyclic and are preferably aromatic or heteroaromatic. Furthermore, a plurality of the ligands may also be linked via one or more substituents $R^1$ as bridging unit to form a relatively large polypodal ligand, and/or a bridge, in particular having 1, 2 or 3 direct bridge atoms, may be present between CCy and DCy in addition to the direct covalent bond.

Particular preference is given to structures of the formulae (6) and (8) which do not contain a further ligand A.

The formulae (2) and (5) to (8) where X=$OR^2$ and Y=$OR^2$ represent a boronic acid ester. The formulae (2) and (5) to (8) where X=$SR^2$ and Y=$SR^2$ represent a thioboronic acid ester. The formulae (2) and (5) to (8) where X=$OR^2$ and Y=Ar represent a borinic acid ester. The formulae (2) and (5) to (8) where X=$SR^2$ and Y=Ar represent a thioborinic acid ester. The formulae (2) and (5) to (8) where X=$N(R^2)_2$ or $NHR^2$ and Y=$N(R^2)_2$ or $NHR^2$ represent a boronic acid amide. The formulae (2) and (5) to (8) where $X=N(R^2)_2$ or $NHR^2$ and $Y=Ar$ represent a borinic acid amide. The formulae (2) and (5) to (8) where $X=OR^2$ and $Y=N(R^2)_2$ or $NHR^2$ represent a boronic acid amidoester. The formulae (2) and (5) to (8) where $X=SR^2$ and $Y=N(R^2)_2$ or $NHR^2$ represent a boronic acid amidothioester. The formulae (2) and (5) to (8) where $X=OBAr_2$ and $Y=Ar$ represent a borinic acid anhydride. The formula (3) where $Z=O$ represents a cyclic boronic acid anhydride. The formula (3) where $Z=NH$ or $NR^2$ represents a cyclic boronic acid imide. The formula (4) where $Z=O$ represents a compound containing a plurality of boronic acid ester units which are bridged via the group L. The formula (4) where $Z=NH$ or $NR^2$ represents a compound containing a plurality of boronic acid amide units which are bridged via the group L. The formula (4) where $Z=S$ represents a compound containing a plurality of thioboronic acid ester units which are bridged via the group L. Mixed forms are likewise permissible here, for example where some of the groups $Z=O$ and other groups $Z=NH$, $NR^2$ or S.

Although evident from the description, it should again be emphasised here that a plurality of radicals $R^1$ can form a ring system with one another and/or that a plurality of radicals $R^2$ can form a ring system with one another. In this connection, the term "aromatic ring system" is also intended to encompass heteroaromatic ring systems. It is preferred for a plurality of radicals $R^2$ to form an aliphatic or aromatic ring system with one another.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the total number of C atoms and heteroatoms is at least 5. The heteroatoms are preferably selected from N, O and/or S. These ring systems may be substituted by $R^1$. For the purposes of this invention, an aromatic or heteroaromatic ring system is taken to mean a system which does not necessarily contain only aryl or heteroaryl groups, but in which a plurality of aryl or heteroaryl groups may also be interrupted by a short, non-aromatic unit (preferably less than 10% of the atoms other than H, particularly preferably less than 5% of the atoms other than H), such as, for example, an $sp^3$-hybridised C, N or O atom. A plurality of aryl or heteroaryl groups may likewise be interrupted by vinyl groups or acetylene groups. A plurality of aryl or heteroaryl groups may furthermore be interrupted by carbonyl groups, phosphine oxide groups, etc. Thus, for example, aromatic ring systems for the purposes of this invention are also taken to mean systems such as 9,9'-spirobifluorene, 9,9-diarylfluorene, triarylamine, diaryl ether, stilbene, tolan, etc. The aromatic or heteroaromatic ring system or a part thereof may also be a fused group here in the sense of the following definition.

For the purposes of this invention, a fused aryl or heteroaryl group is taken to mean a ring system having 9 to 40 aromatic ring atoms in which at least two aromatic or heteroaromatic rings are fused to one another, i.e. have at least one common edge and a common aromatic π-electron system. These ring systems may be substituted by $R^1$ or unsubstituted. Examples of fused aromatic or heteroaromatic ring systems are naphthalene, quinoline, isoquinoline, quinoxaline, anthracene, acridine, phenanthrene, phenanthroline, pyrene, naphthacene, perylene, chrysene, etc., while biphenyl, for example, is not a fused aryl group since there is no common edge between the two ring systems therein. Fluorene or spirobifluorene is likewise not a fused aromatic ring system since the phenyl units therein do not form a common aromatic electron system.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methyl-butyl, n-pentyl, s-pentyl, cyclopentyl, n-hexyl, cyclohexyl, n-heptyl, cyclo-heptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. An aromatic ring system having 6 to 60 C atoms or a heteroaromatic ring system having 2 to 60 C atoms, which may also in each case be substituted by the above-mentioned radicals $R^1$ and which may be linked to the aromatic or heteroaromatic ring via any desired positions, is in particular taken to mean groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, diphenyl ether, triphenylamine, dihydrophenanthrene, dihydropyrene, tetrahydropyrene, cis- or trans-indenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine or benzothiadiazole.

In a preferred embodiment of the invention, the symbol X stands for $OR^2$ or $OBAr_2$. The compounds of the formulae (2) and (5) to (8) thus preferably stand for a boronic acid ester or for a borinic acid ester or for a borinic acid anhydride. In a particularly preferred embodiment of the invention, the symbol X stands for $OR^2$. In a very particularly preferred embodiment of the invention, the symbol X stands for $OR^2$ and the symbol Y simultaneously stands for $OR^2$. The compounds of the formulae (2) and (5) to (8) thus very particularly preferably stand for a boronic acid ester. It is very particularly preferred here for the two radicals $R^2$ of the groups $OR^2$ to form an aliphatic or aromatic ring system with one another. This means that the boronic acid ester is formed by an aliphatic or aromatic diol. The cyclic system which forms here is preferably a five-membered ring (1,3,2-dioxaborolane) or a six-membered ring (1,3,2-dioxaborinane), i.e. the cyclic boronic acid ester is preferably formed by a 1,2-diol or by a 1,3-diol.

In a further preferred embodiment of the invention, the symbols X and Y, identically or differently on each occurrence, stand for NHR² or N(R²)₂, particularly preferably for N(R²)₂. The compounds of the formulae (2) and (5) to (8) thus preferably stand for a boronic acid amide. It is very particularly preferred here for two radicals R² of the groups N(R²)₂ on different N atoms to form an aliphatic or aromatic ring system with one another. This means that the boronic acid ester is formed by an aliphatic or aromatic diamine. The cyclic system which forms here is preferably a five-membered ring (1,3,2-diazaborolane) or a six-membered ring (1,3,2-diazaborinane), i.e. the cyclic boronic acid amide is preferably formed by a 1,2-diamine or by a 1,3-diamine.

In a further preferred embodiment of the invention, the symbol Z in the formula (3) stands for O. The compound of the formula (3) thus preferably stands for a cyclic boronic acid anhydride. m here is particularly preferably 1 or 2, very particularly preferably 2.

In a further preferred embodiment of the invention, the symbol Z in the formula (4), identically or differently on each occurrence, stands for O or for NR², particularly preferably all Z stand for O or for NR². The compound of the formula (4) thus particularly preferably stands for an oligoboronic acid ester in which a plurality of boronic acid esters are linked via the group L, or for an oligoboronic acid amide in which a plurality of boronic acid amides are linked via the group L. q here is particularly preferably 2, 3 or 4, very particularly preferably q=2 or 3. Suitable as linking group L are both straight-chain, branched or cyclic aliphatic compounds and also aromatic compounds. In principle, all aliphatic oligoalcohols and oligoamines are suitable for the synthesis. Preference is given to those which are readily accessible synthetically or are naturally available. A preferred aliphatic alcohol is pentaerythritol. Further preferred aliphatic compounds are sugar alcohols, which are reacted with the corresponding free boronic acids to give the oligoboronic acid esters. These may be straight-chain (for example mannitol) or cyclic (for example cis-, epi-, allo-, myo-, neo-, muco-, chiro- or scyllo-inositol). In principle, preference is given to all naturally occurring sugar alcohols. Preference is furthermore given to monosaccharides, oligosaccharides or polysaccharides, likewise cyclic sugars, such as, for example, α-, β- or γ-cyclodextrins. In the case of aromatic compounds, all aromatic rings which are substituted by four or more hydroxyl groups and/or amino groups are in principle suitable. The hydroxyl groups here may be bonded to one or more aryl groups linked to one another. Preferred units here are 1,2,3,4-tetrahydroxybenzene, 1,2,4,5-tetrahydroxybenzene, 1,2,3,4,5,6-hexahydroxybenzene, 4,5,9,10-tetrahydroxytetrahydropyrene, 1,4,5,8-tetrahydroxynaphthalene, 2,2',3,3'-tetrahydroxy-1,1'-biphenyl, 3,3',4,4'-tetrahydroxy-1,1'-biphenyl, 2,3,6,7-tetrahydroxyspirobifluorene, etc.

Preferred radicals R¹ are, if present, identically or differently on each occurrence, F, a straight-chain alkyl or alkoxy chain having 1 to 10 C atoms or a branched alkyl or alkoxy chain having 3 to 10 C atoms, each of which may be substituted by R³ and in which one or more non-adjacent C atoms may be replaced by N—R³, O, S, —CR³=CR³— or —C≡C— and in which one or more H atoms may be replaced by F or CN, or an aromatic or heteroaromatic ring system having 5 to 16 aromatic ring atoms, which may also be substituted by one or more radicals R³, or a combination of two or three of these systems; two or more radicals R¹ here may also form a mono- or polycyclic, aliphatic or aromatic ring system with one another. Particularly preferred radicals R¹ are, if present, identically or differently on each occurrence, F, a straight-chain alkyl chain having 1 to 5 C atoms or a branched alkyl chain having 3 to 5 C atoms, in which, in addition, one or more non-adjacent C atoms may be replaced by —CR³=CR³— or —C≡C— and in which one or more H atoms may be replaced by F, or an aryl or heteroaryl group having 5 to 10 aromatic ring atoms, which may also be substituted by one or more radicals R³, or a combination of two of these systems; two or more radicals R¹ here may also form a mono- or polycyclic, aliphatic or aromatic ring system with one another.

Preferred radicals R² are, identically or differently on each occurrence, a straight-chain alkyl chain having 1 to 10 C atoms or a branched or cyclic alkyl chain having 3 to 10 C atoms, each of which may be substituted by R³ and in which one or more non-adjacent C atoms may be replaced by N—R³, O, S, —CR³=CR³— or —C≡C—, with the proviso that a heteroatom is not bonded directly to the oxygen or sulfur or nitrogen of the group X or Y, and in which one or more H atoms may be replaced by F, or an aromatic or heteroaromatic ring system having 5 to 16 aromatic ring atoms, which may also be substituted by one or more radicals R³, or a combination of two or three of these systems; two or more radicals R² here may also form a mono- or polycyclic, aliphatic or aromatic ring system with one another. In a particularly preferred embodiment of the invention, two radicals R², together with B, X and Y, form a ring system, where the formation of a five-, six- or seven-membered ring, in particular a five- or six-membered ring, is particularly preferred. Very particularly preferred groups R² in the formation of ring systems are 1,2-ethylene, 1,3-propylene, 1,2-phenylene and 1,8-naphthylene, each of which may also be substituted by one or more radicals R³. It is furthermore preferred for the radicals R² to form a ring system with R¹.

The preferred groups Ar in the formulae (2) to (4) depend on the respective intended use of the boronic acid or borinic acid derivatives in the organic electronic device. In particular, they differ depending on whether the compound is used as host for fluorescent or for phosphorescent emitters. The preferred host materials are equally suitable as electron-transport materials. Different groups Ar are likewise preferred if the boronic acid or borinic acid derivative is to be employed as hole-transport compound or as fluorescent or phosphorescent dopant.

For use as host material for fluorescent emitters and as electron-transport material, the aromatic ring system Ar in a preferred embodiment contains at least one fused aryl or heteroaryl group. The boron atom is preferably bonded directly to this fused aryl or heteroaryl group. It may be preferred here for further aromatic radicals to be bonded to the fused aryl or heteroaryl group. It may likewise be preferred for more than one boron atom to be bonded to the fused aryl or heteroaryl group or for a plurality of fused aryl or heteroaryl groups to each of which one or more boronic acid or borinic acid derivatives are bonded to be bonded to one another. It is furthermore preferred, in particular for blue-emitting devices, for the host material to contain no double bonds, i.e. no stilbene structures, etc.

The fused aryl or heteroaryl group particularly preferably contains two, three, four or five aromatic or heteroaromatic units, which are in each case fused to one another via one or more common edges and thus form a common aromatic system and which may be substituted by R¹ or unsubstituted. The substitution by R¹ may be appropriate in order to adjust the electronic properties or also in order to obtain compounds with better solubility. The fused aryl or heteroaryl group very particularly preferably contains three or four aromatic or heteroaromatic units, which are in each case fused to one another via one or more common edges and thus form a common aromatic system and which may be substituted by R¹ or unsubstituted. The aromatic and heteroaromatic units fused to one another are very particularly preferably selected from benzene, pyridine, pyrimidine, pyrazine and pyridazine, each of which may be substituted by R¹ or unsubstituted, in particular benzene and pyridine, each of which may be substituted by R¹ or unsubstituted.

The fused aryl or heteroaryl groups are particularly preferably selected from the group consisting of anthracene, acridine, phenanthrene, phenanthroline, pyrene, naphthacene, chrysene, pentacene and perylene, each of which may optionally be substituted by R¹. The fused aromatic ring systems are particularly preferably selected from the group consisting of anthracene, phenanthrene, pyrene and naphthacene, in particular anthracene, phenanthrene and pyrene, each of which may optionally be substituted by R¹. R² is very particularly preferably a bridging group between X and Y, selected from 1,2-phenylene, 1,8-naphthylene, 1,2-ethylene and 1,3-propylene. A plurality of groups R² on different boronic acid derivatives in the same compound may furthermore preferably also form a ring system and thus produce, for example, an ansa compound.

For clarity, the numbering of anthracene, phenanthrene, pyrene and perylene is shown below:

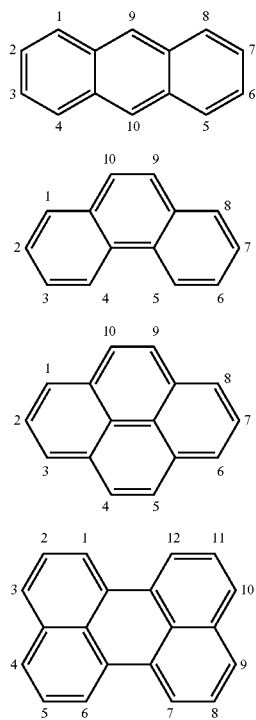

The boronic acid or borinic acid derivative is preferably linked to anthracene here via the 2- or 9-position if only one such group is present, in particular via the 9-position. The 10-position is then particularly preferably further substituted by an aromatic substituent. The boronic acid or borinic acid derivatives are preferably linked to anthracene via the 2,9-position, the 2,10-position, the 9,10-position or the 2,6-position if two such groups are present, particularly preferably via the 9,10-position.

The boronic acid or borinic acid derivative is preferably linked to pyrene via the 1- or 2-position if only one such group is present. The boronic acid or borinic acid derivatives are preferably linked to pyrene via the 1,6-, the 1,8-, the 1,3- or the 2,7-position if two such groups are present, particularly preferably via the 1,6- or via the 2,7-position. The boronic acid or borinic acid derivatives are preferably linked to pyrene via the 1,3,6,8-position if four such groups are present.

The boronic acid or borinic acid derivative is preferably linked to phenanthrene via the 2-, the 3- or the 9-position if only one such group is present. The boronic acid or borinic acid derivatives are preferably linked to phenanthrene via the 2,7-, the 3,6-, the 2,9-, the 2,10- or the 9,10-position if two such groups are present, particularly preferably via the 2,7- or via the 3,6-position.

The boronic acid or borinic acid derivative is preferably linked to perylene via the 3-position if only one such group is present. The boronic acid or borinic acid derivatives are preferably linked to perylene via the 3,4-, the 3,9- or the 3,10-position if two such groups are present, particularly preferably via the 3,9- or via the 3,10-position. The boronic acid or borinic acid derivatives are preferably linked to perylene via the 3,4,9,10-position if four such groups are present.

For use as host material for phosphorescent emitters and as electron-transport material, the aromatic ring system Ar in a preferred embodiment contains only aryl or heteroaryl groups having 5 to 14 aromatic ring atoms, but none having more than 14 aromatic ring atoms. This does not exclude that a plurality of such groups may be present in the aromatic ring system Ar, but excludes fused aryl or heteroaryl groups having more than 14 aromatic ring atoms. It may be preferred here for more than one boron atom to be bonded to the aromatic or heteroaromatic ring system. It is furthermore preferred for the host material to contain no double bonds, i.e. no stilbene structures, etc. In a particularly preferred embodiment, the aromatic ring system Ar contains only aryl or heteroaryl groups which contain not more than 10 aromatic ring atoms, in particular selected from benzene, naphthalene, pyridine, pyrimidine, pyrazine, pyridazine, quinoline, isoquinoline, quinoxaline, triazine, thiophene, benzothiophene, pyrrole, indole, furan, pyrazole, imidazole, triazole and oxadiazole, which may be substituted by R¹. In particular for use as host material for phosphorescent emitters and as electron-transport material, it is also preferred for a plurality of aryl groups to be interrupted by a non-conjugated unit, particularly preferably by a carbonyl group, an aromatic phosphine group, an aromatic phosphine oxide group, a thio group, a sulfoxide, a sulfone or a C(R¹)₂ group, in particular a carbonyl group or an aromatic phosphine oxide group.

Particularly preferred groups Ar contain benzene, 2-biphenyl, 3-biphenyl, 4-biphenyl, fluorene, dihydrophenanthrene, spirobifluorene, terphenyl, naphthyl or binaphthyl. These may each be substituted by R¹ or unsubstituted and may have one or more bonded boronic acid or borinic acid derivatives.

For use as hole-transport material for fluorescent or phosphorescent organic electroluminescent devices or for other organic electronic devices, it is preferred for the group Ar to contain at least one triarylamine unit and/or at least one thiophene derivative. The group particularly preferably contains at least one triarylamine unit. This may be structures having precisely one or having a plurality of nitrogen atoms, for example triphenylamine, naphthyldiphenylamine, TAD, NPB, NaphDATA, etc.

For use as fluorescent dopant for organic electroluminescent devices, it is preferred for the group Ar to contain at least one stilbene unit and/or at least one tolan unit, particularly preferably at least one stilbene unit. In addition to the stilbene unit, the group Ar very particularly preferably contains at least one triarylamine unit.

Examples of boronic acid or borinic acid derivatives which are suitable as host materials for fluorescent or phosphorescent devices, as electron-transport materials, as hole-transport materials or as emitters are the structures (1) to (198) shown below. Which of the compounds shown is particularly suitable for fluorescent devices and which for phosphorescent devices, or which is also suitable for other uses, is revealed by the above description.

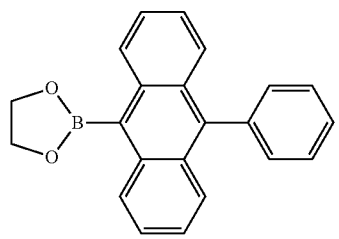
(1)

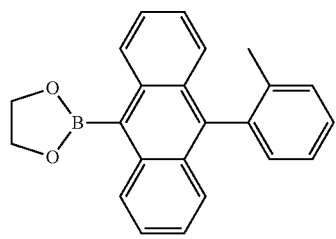
(2)

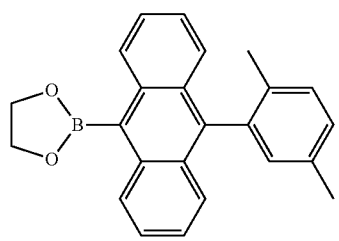
(3)

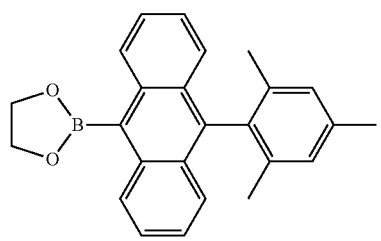
(4)

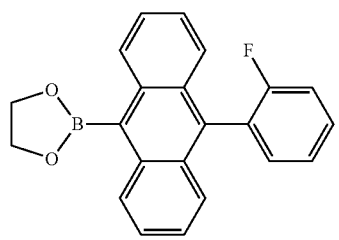
(5)

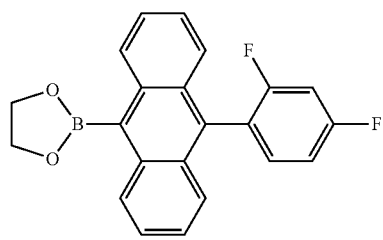
(6)

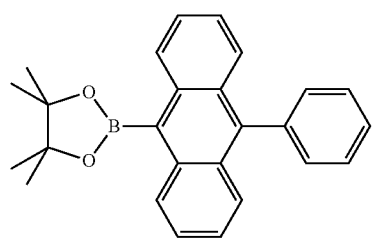
(7)

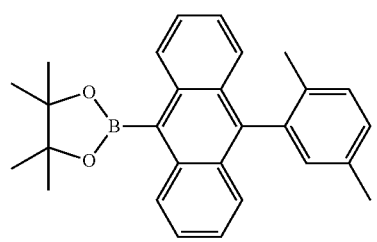
(8)

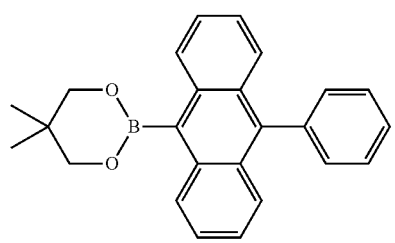
(9)

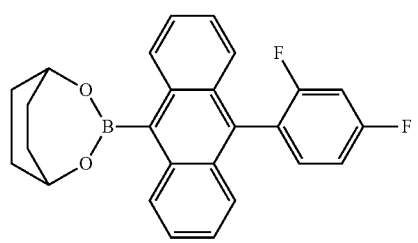
(10)

-continued
(11)
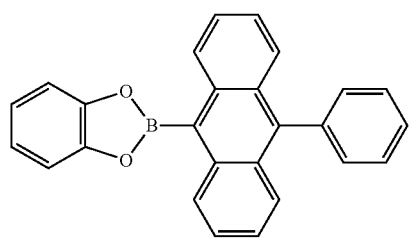
(12)
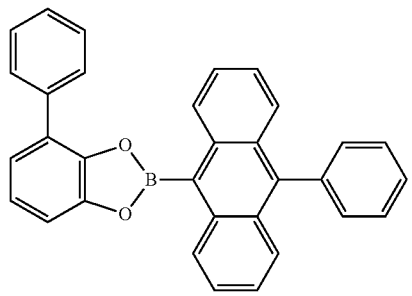
(13)
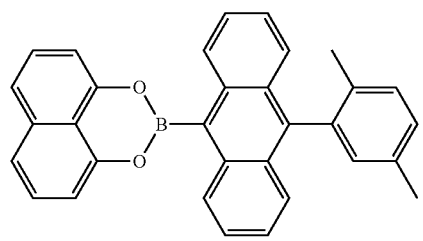
(14)
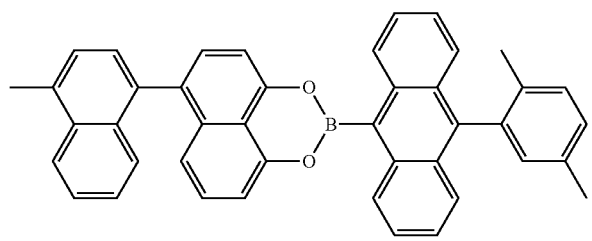
(15)
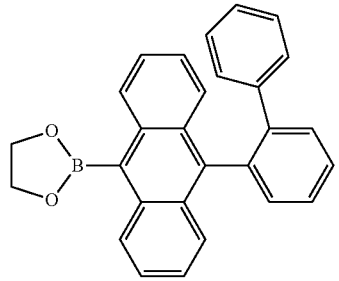
(16)
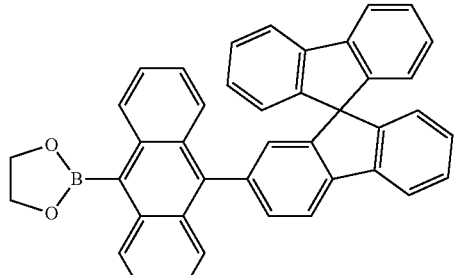
(17)
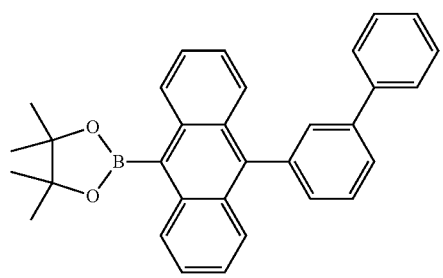
(18)
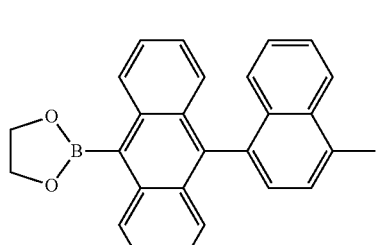
(19)
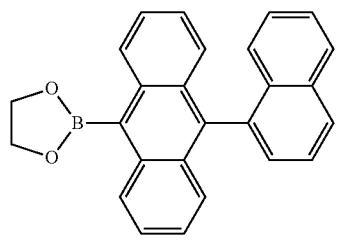
(20)
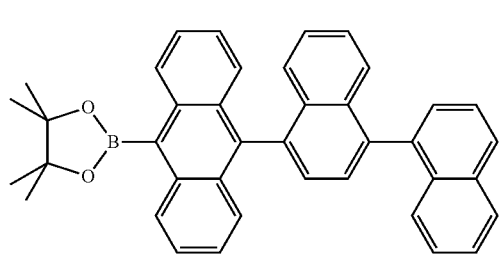
(21)
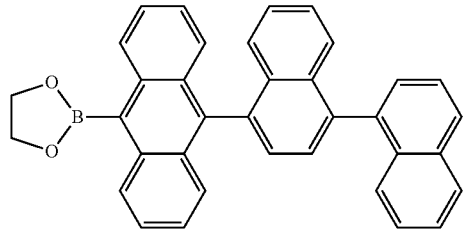
(22)

-continued
(23)
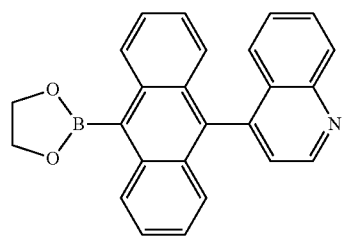
(24)
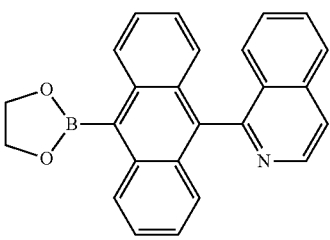
(25)
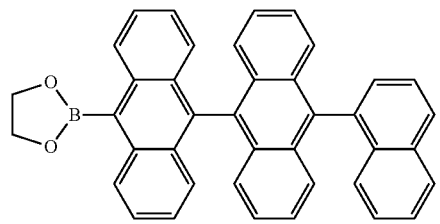
(26)
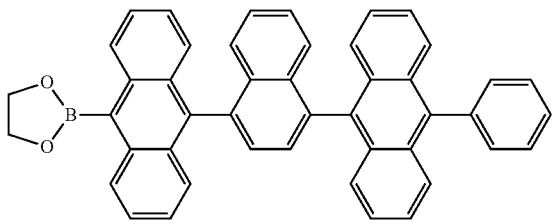
(27)
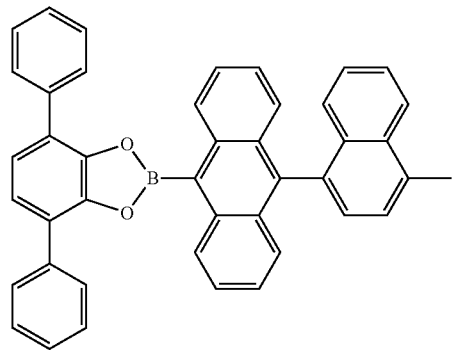
(28)
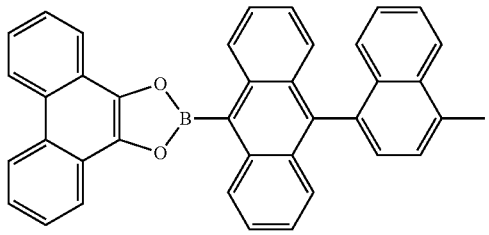
(29)
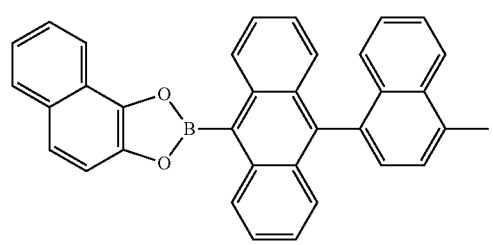
(30)
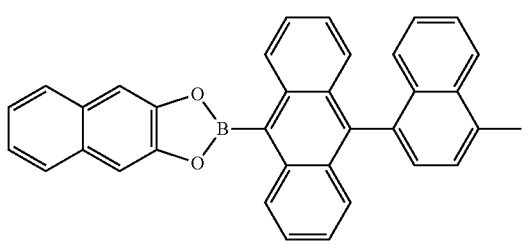
(31)
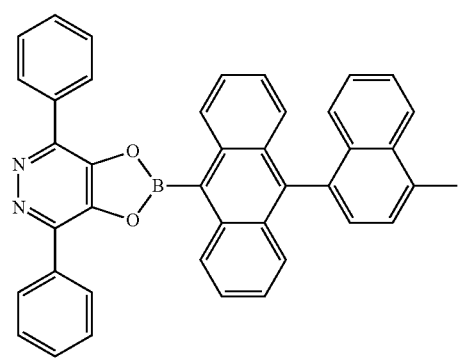
(32)
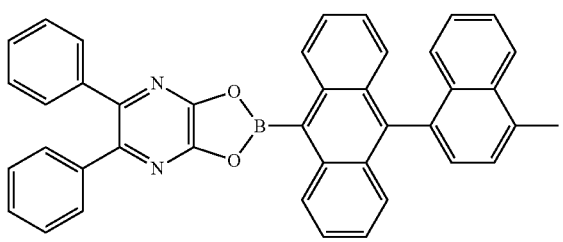

-continued
(33)
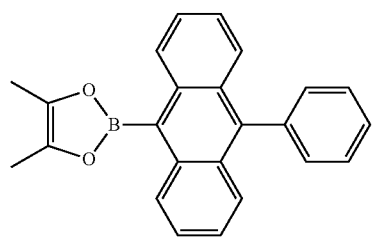
(34)
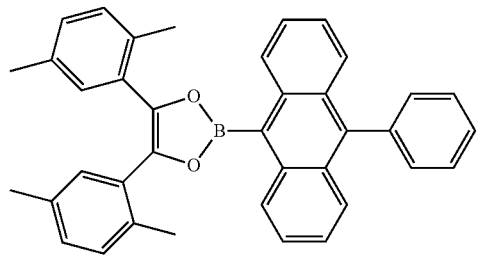
(35)
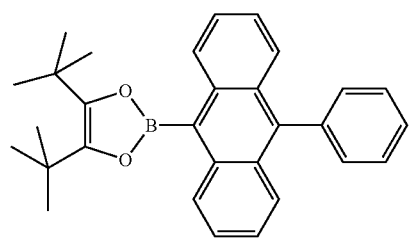
(36)
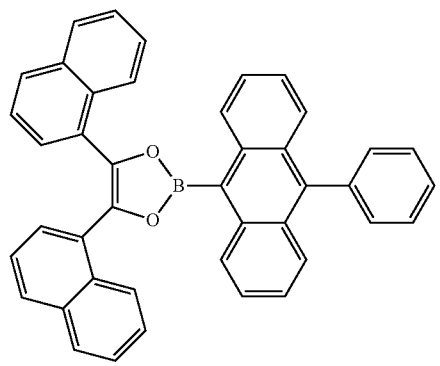
(37)
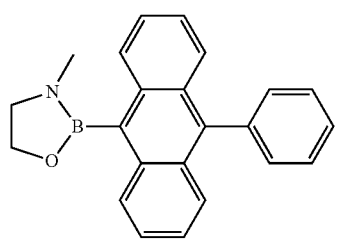
(38)
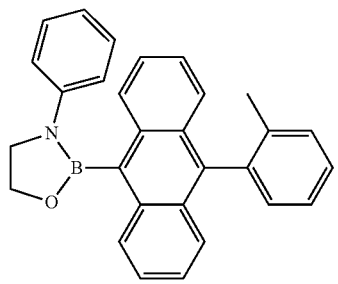
(39)
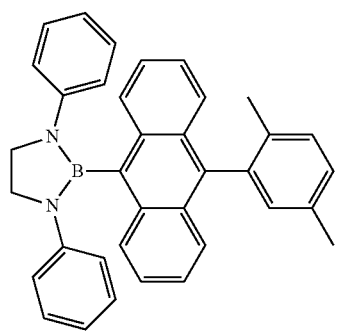
(40)
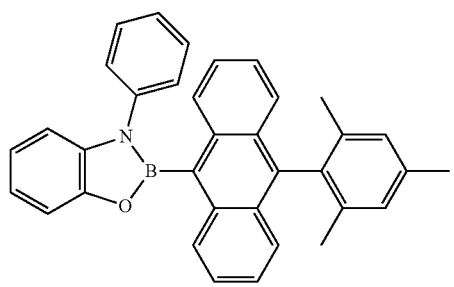
(41)
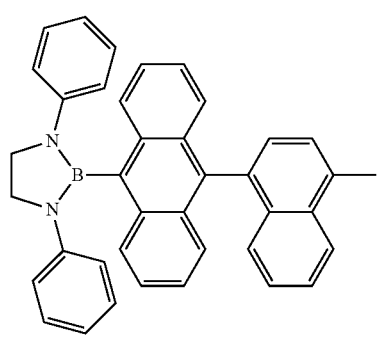
(42)
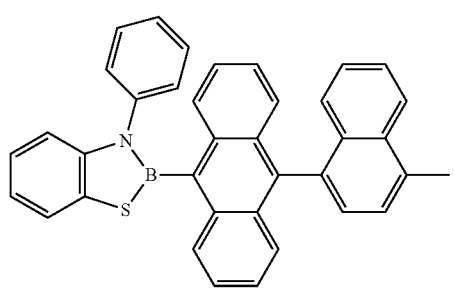

-continued
(43)
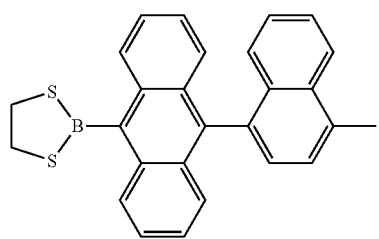
(44)
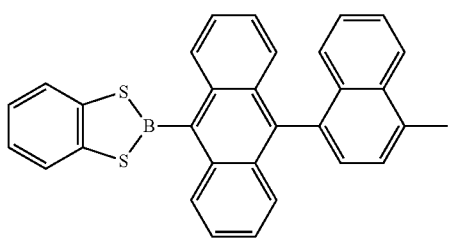
(45)
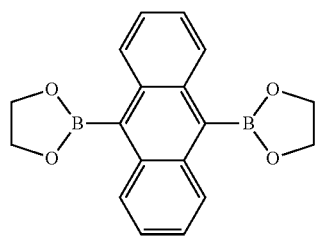
(46)
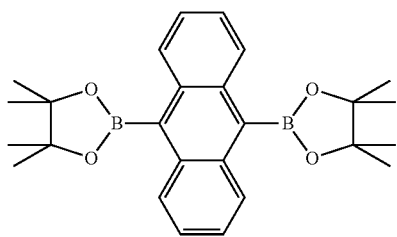
(47)
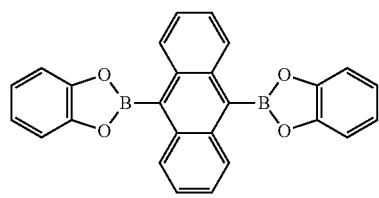
(48)
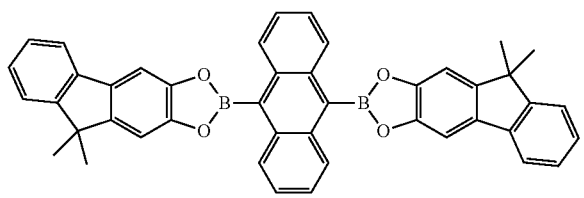
(49)
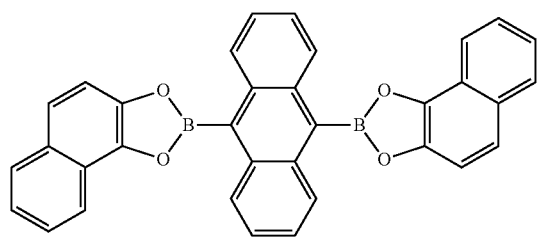
(50)
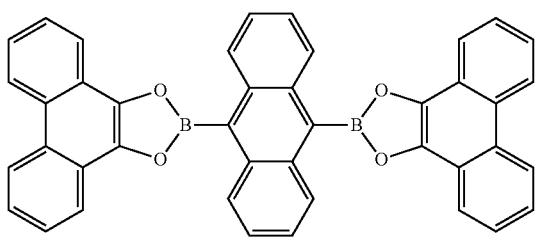
(51)
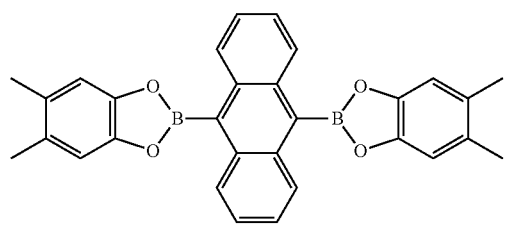
(52)
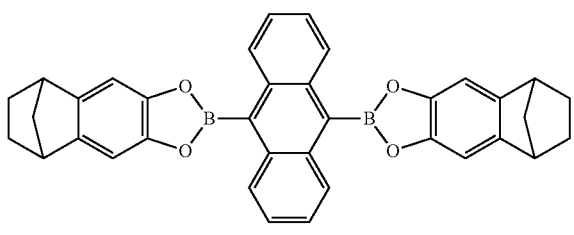
(53)
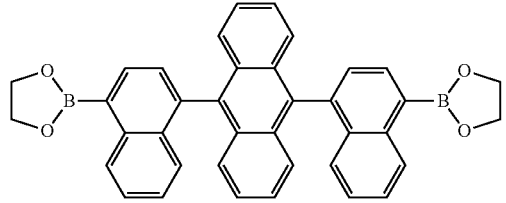
(54)
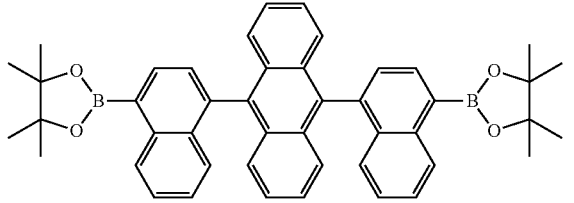
(55)
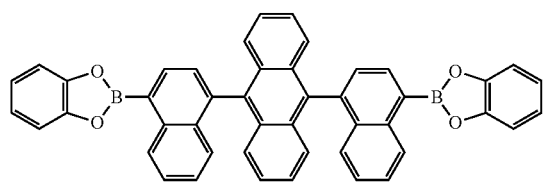
(56)
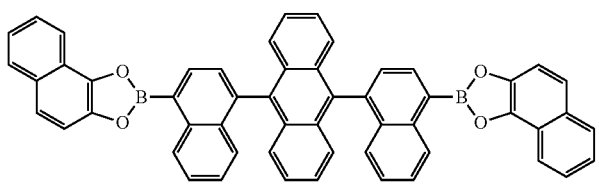

-continued
(57)
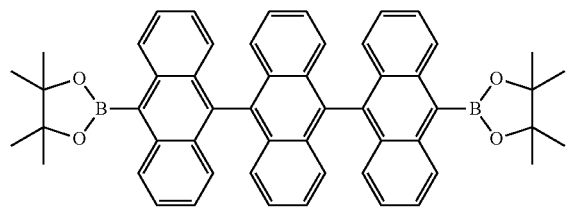
(58)
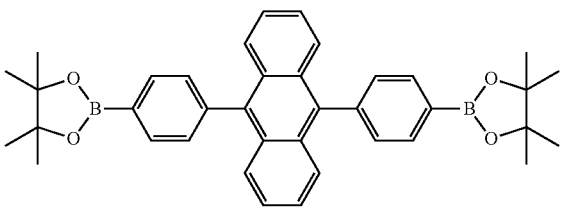
(59)
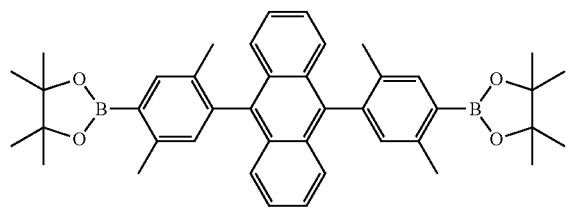
(60)
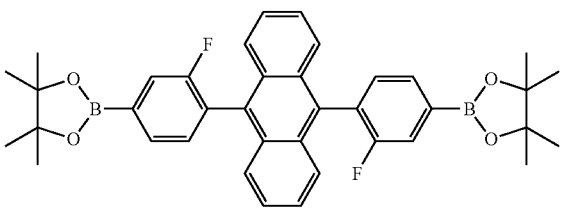
(61)
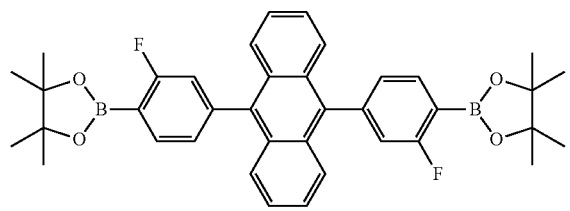
(62)
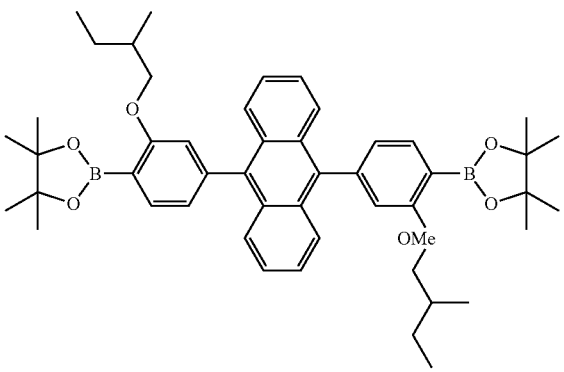
(63)
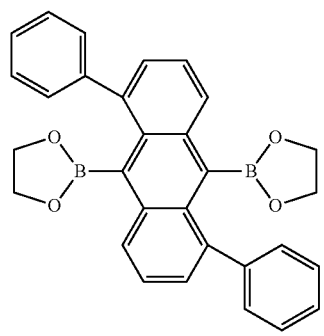
(64)
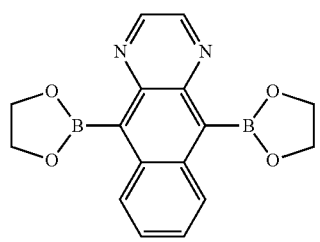
(65)
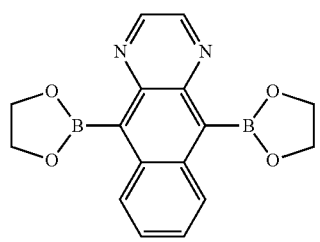
(66)
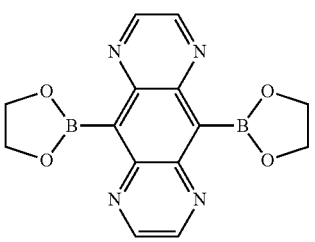

-continued
(67)
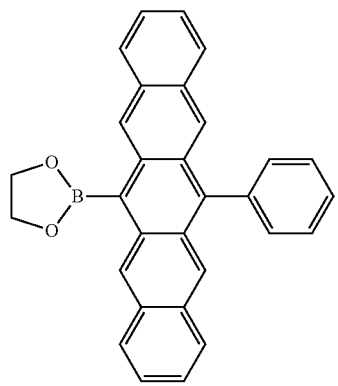
(68)
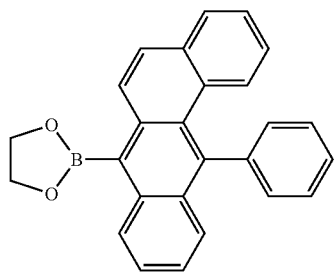
(69)
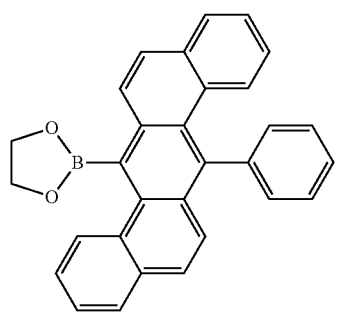
(70)
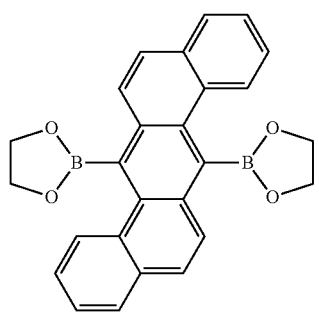
(71)
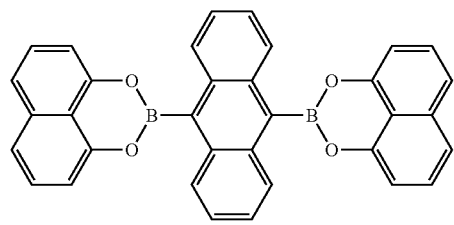
(72)
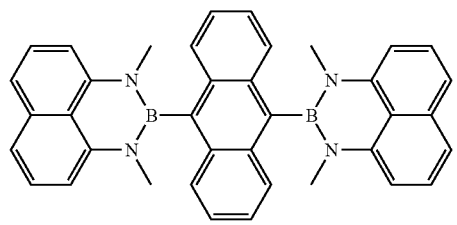
(73)
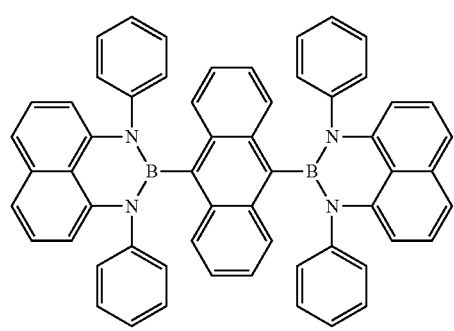
(74)
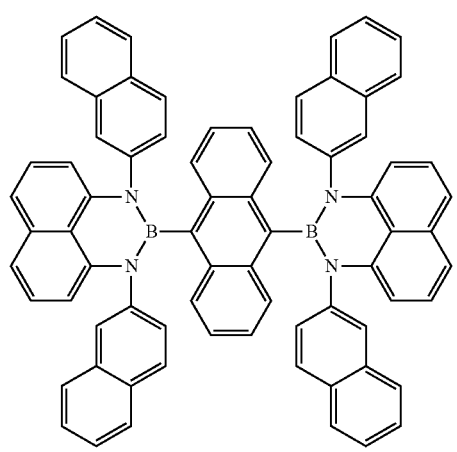
(75)
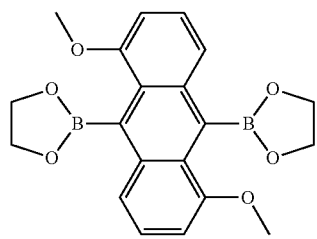
(76)
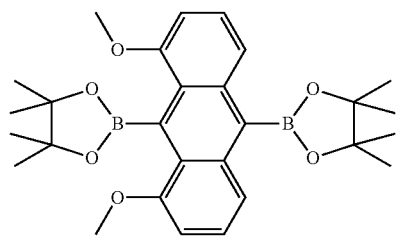

(77) 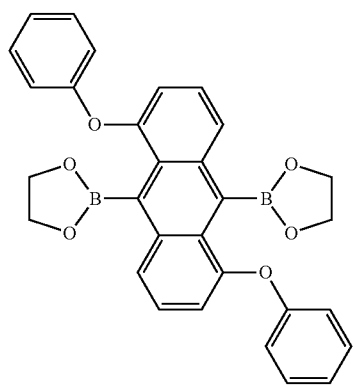
(78) 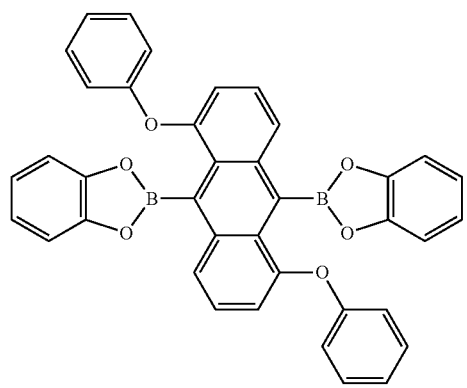
(79) 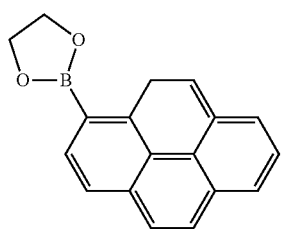
(80) 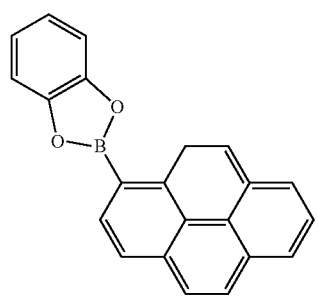
(81) 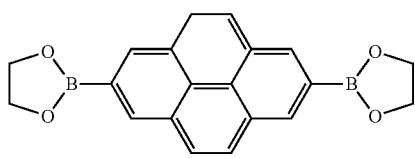
(82) 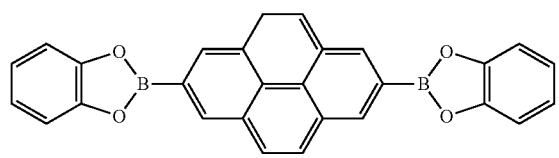
(83) 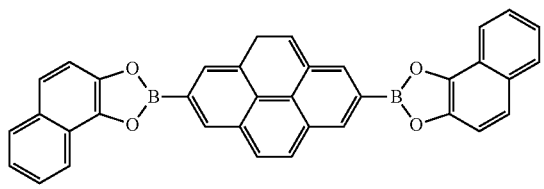
(84) 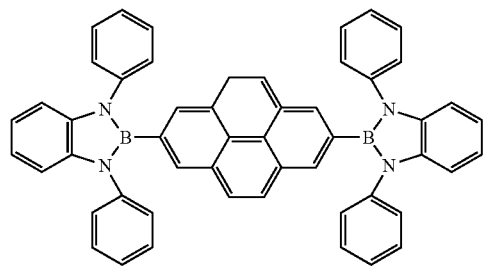
(85) 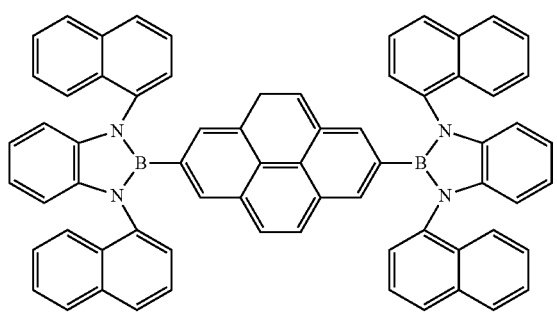
(86) 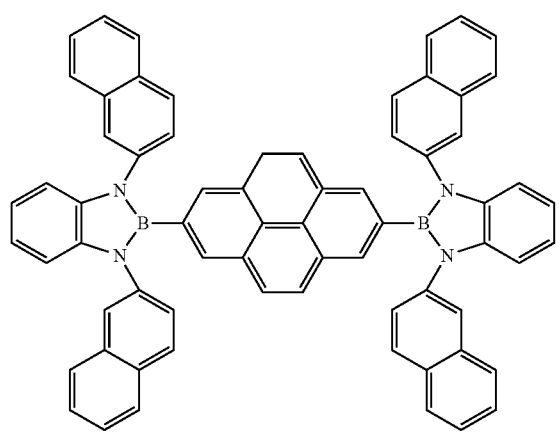

-continued
(87)
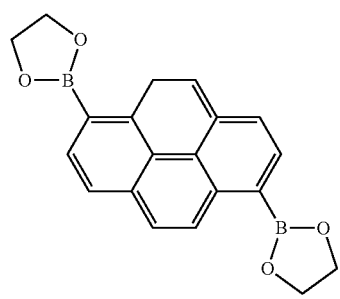
(88)
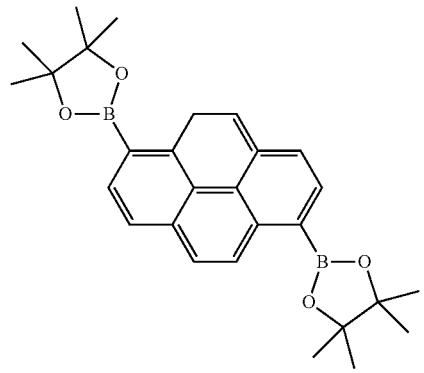
(89)
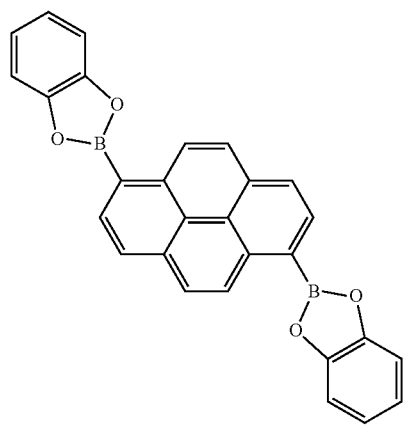
(90)
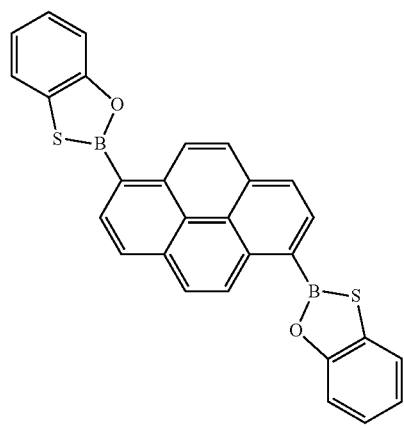
(91)
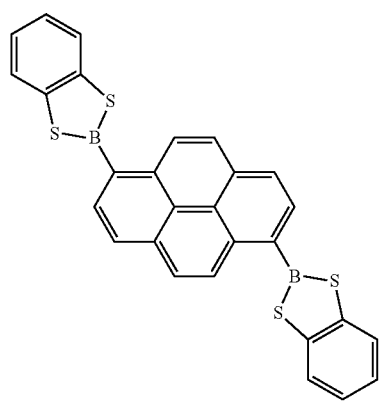
(92)
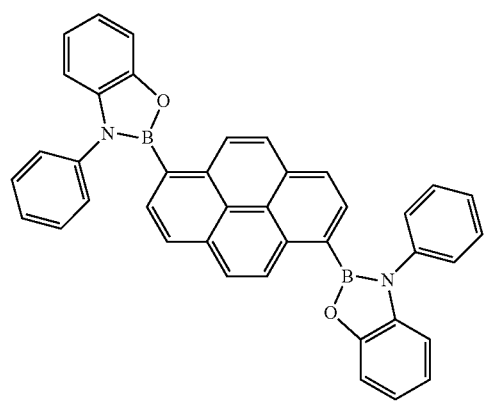

-continued
(93)
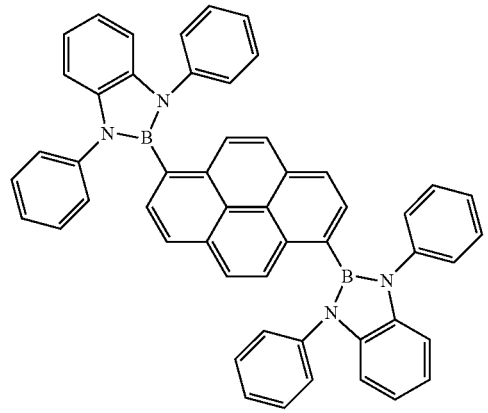
(94)
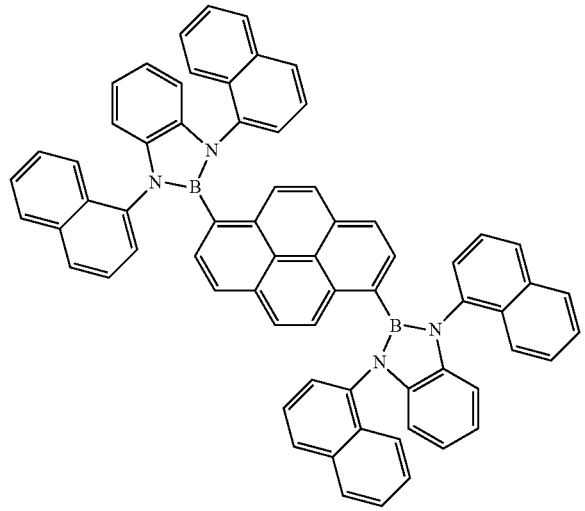
(95)
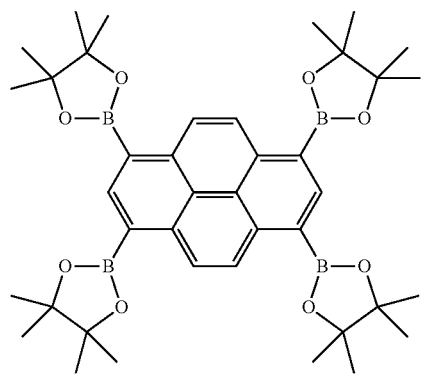
(96)
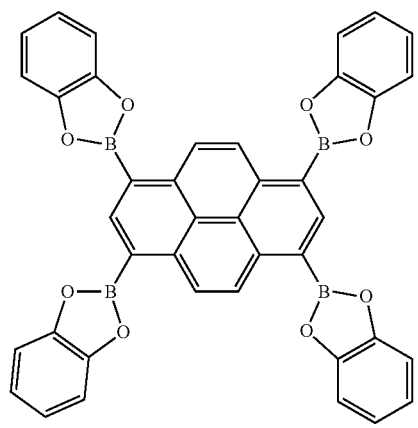
(97)
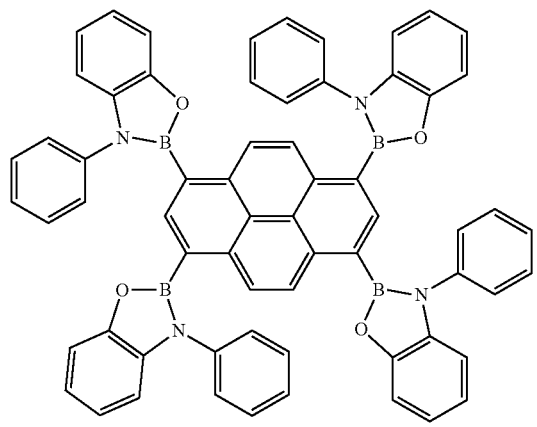
(98)
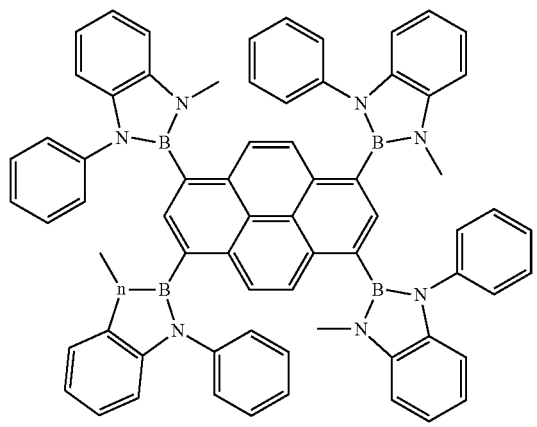
(99)
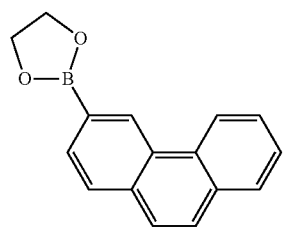
(100)
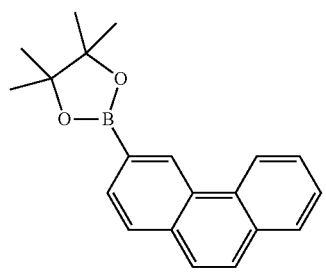

-continued
(101)
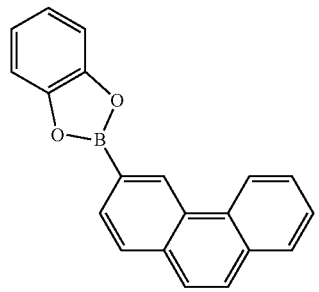
(102)
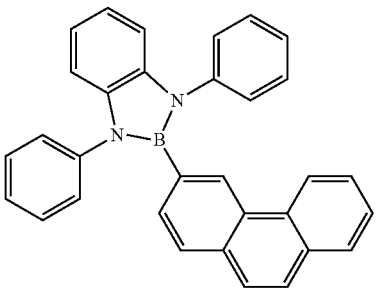
(103)
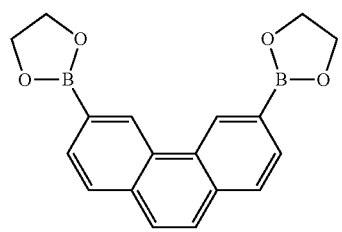
(104)
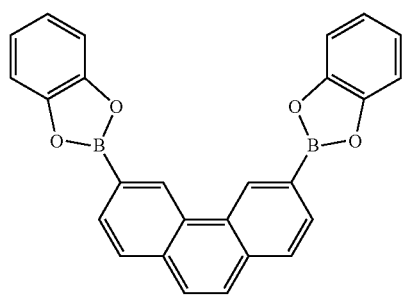
(105)
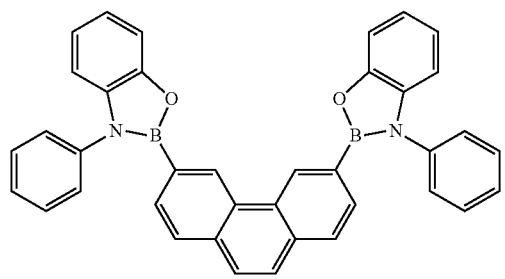
(106)
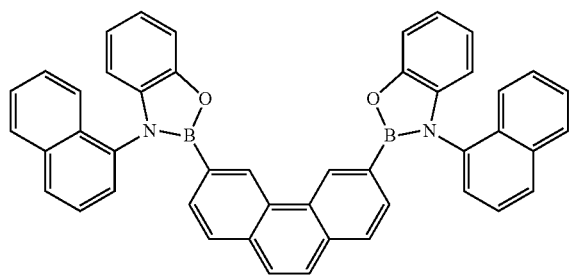
(107)
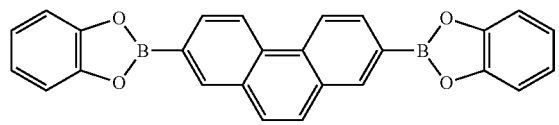
(108)
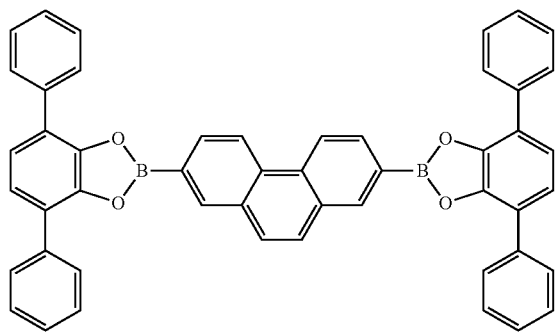
(109)
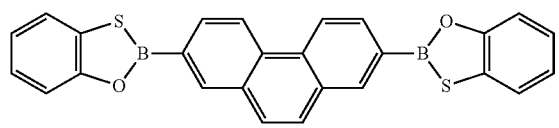
(110)
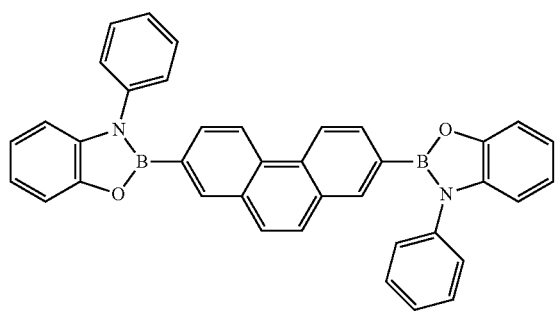

-continued
(111)
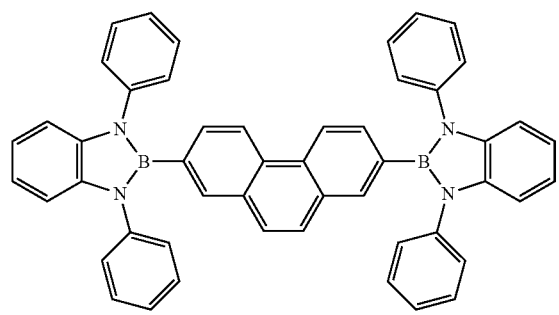
(112)
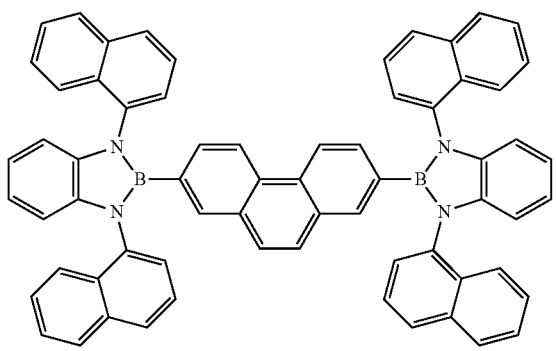
(113)
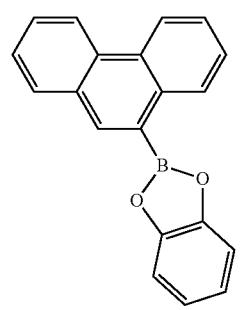
(114)
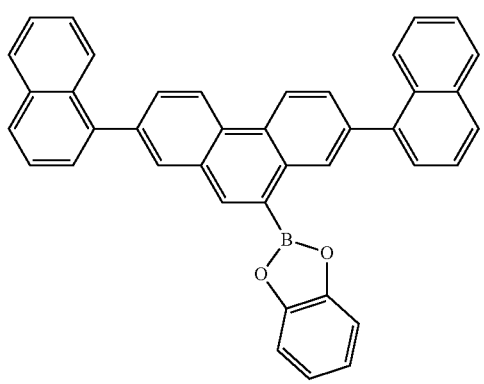
(115)
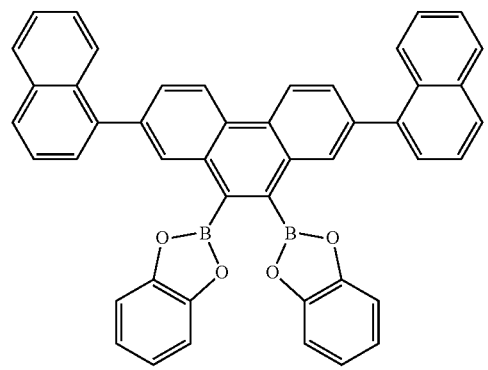
(116)
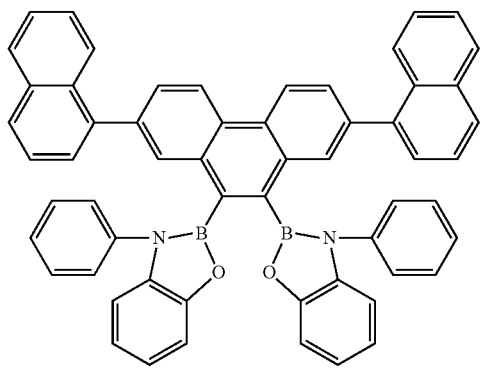
(117)
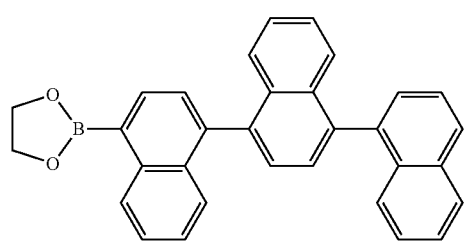
(118)
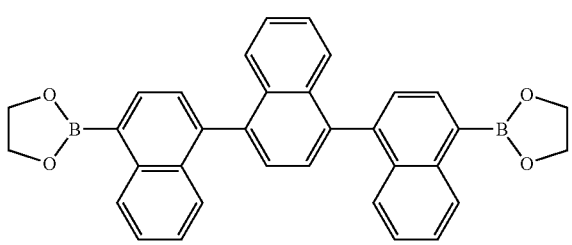
(119)
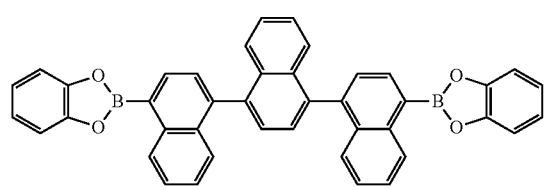
(120)
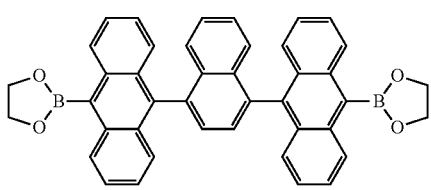

-continued
(121)
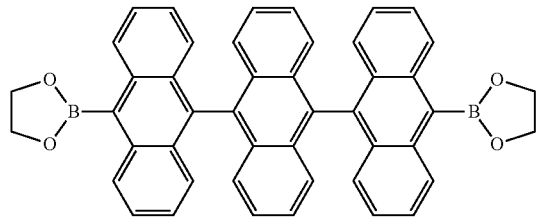
(122)
(123)
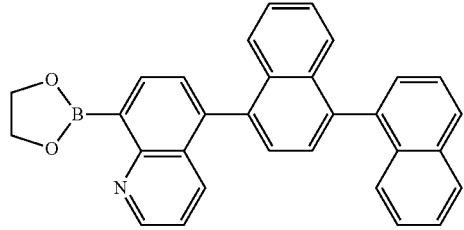
(124)
(125)
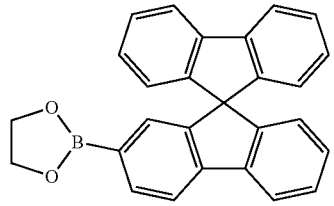
(126)
(127)
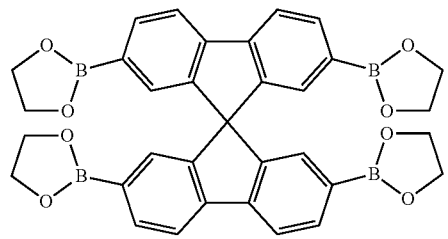
(128)
(129)
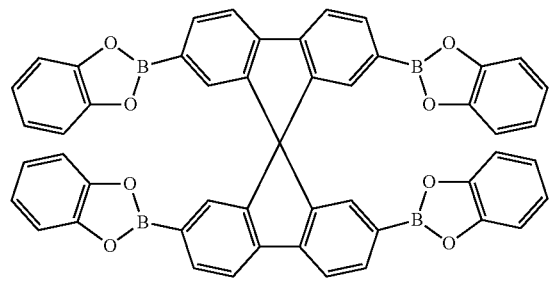
(130)
(131)
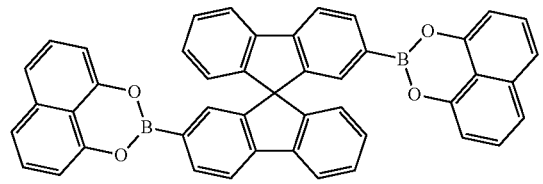
(132)
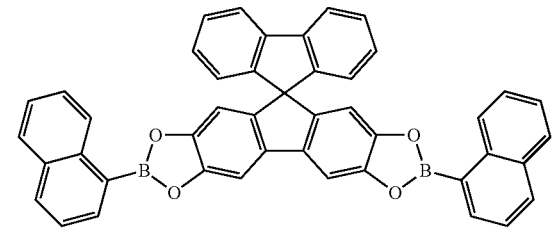

-continued
(133)
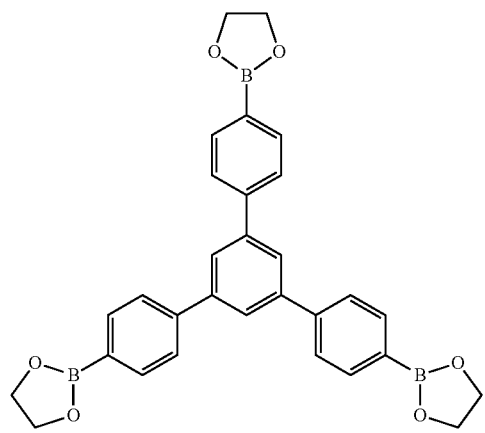
(134)
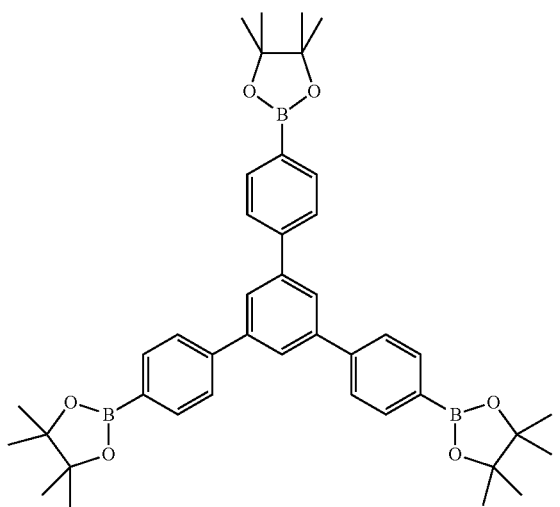
(135)
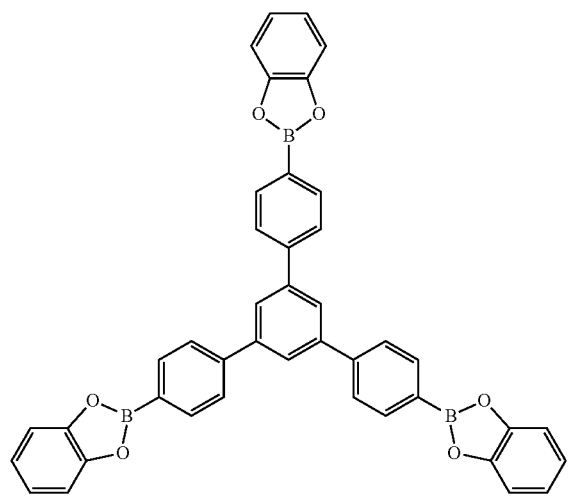
(136)
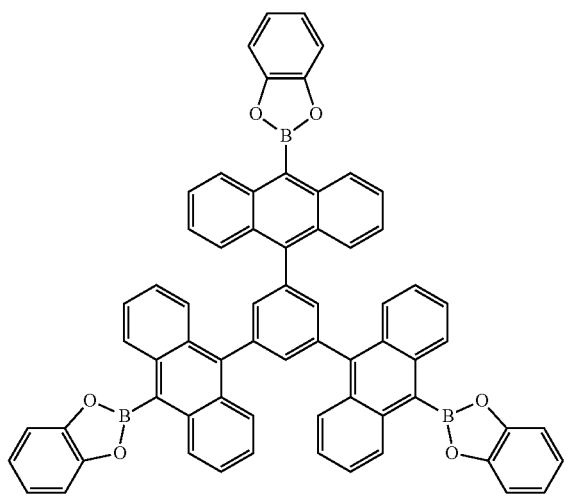
(137)
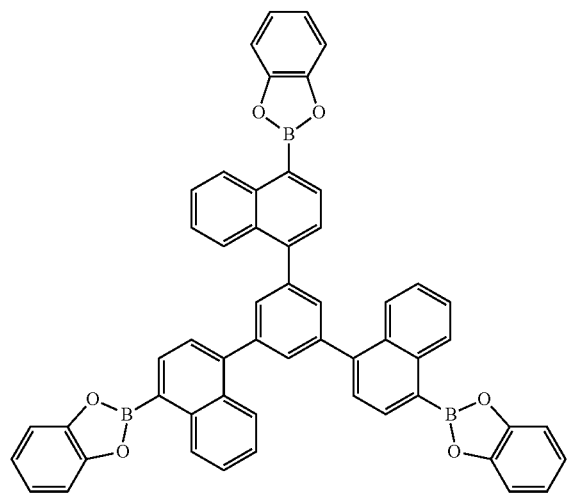
(138)
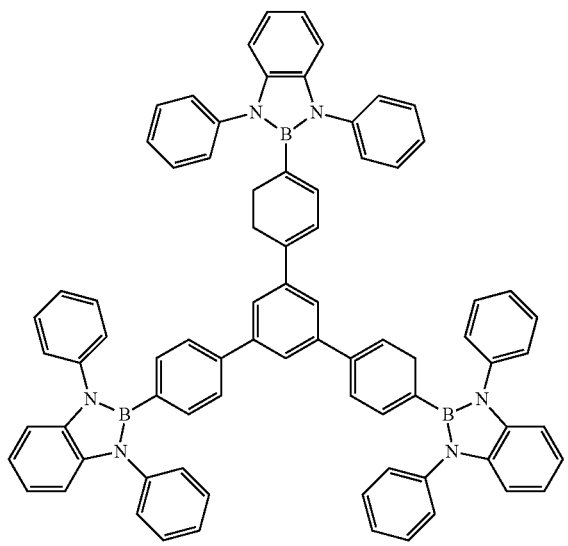

-continued
(139)
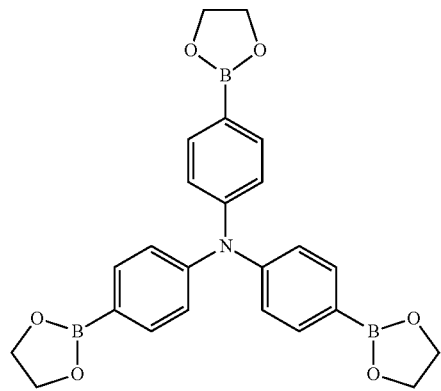
(140)
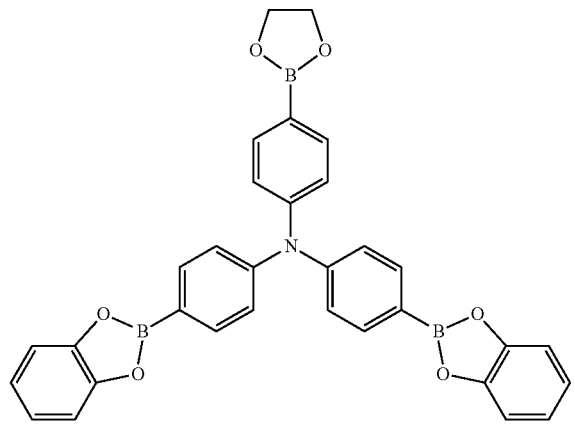
(141)
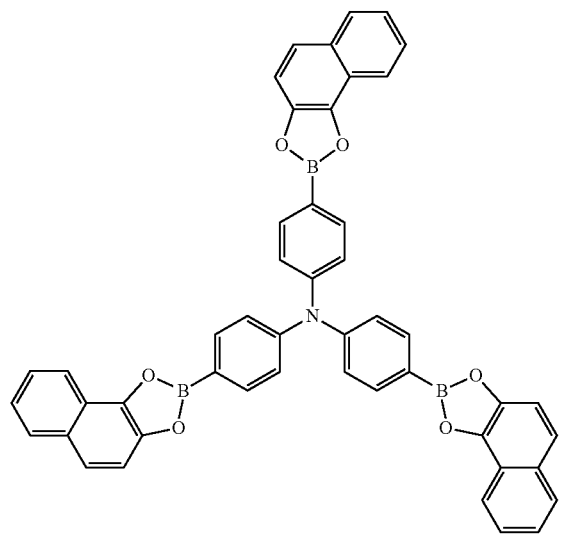
(142)
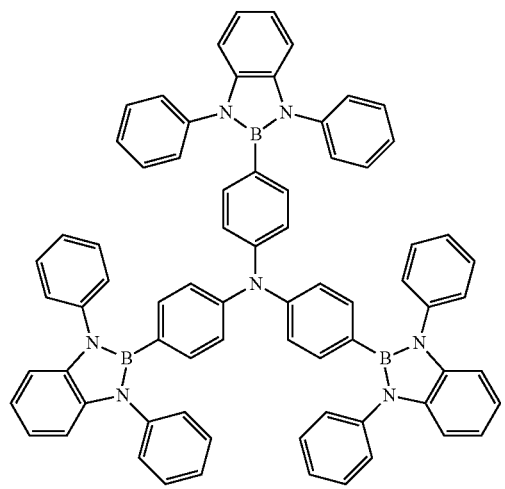
(143)
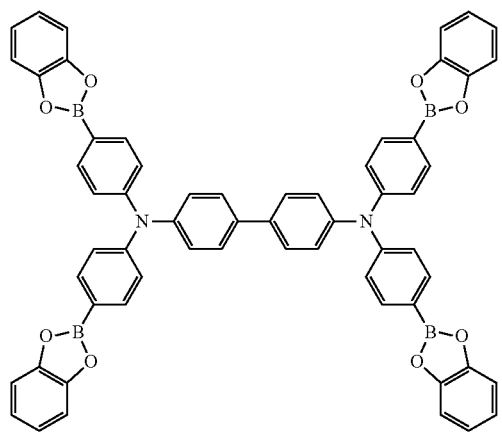
(144)
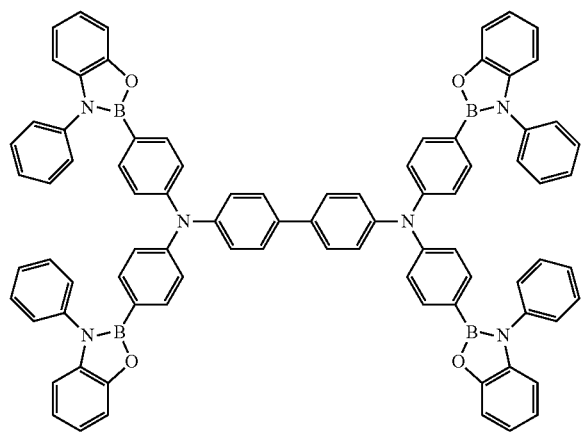

(145)
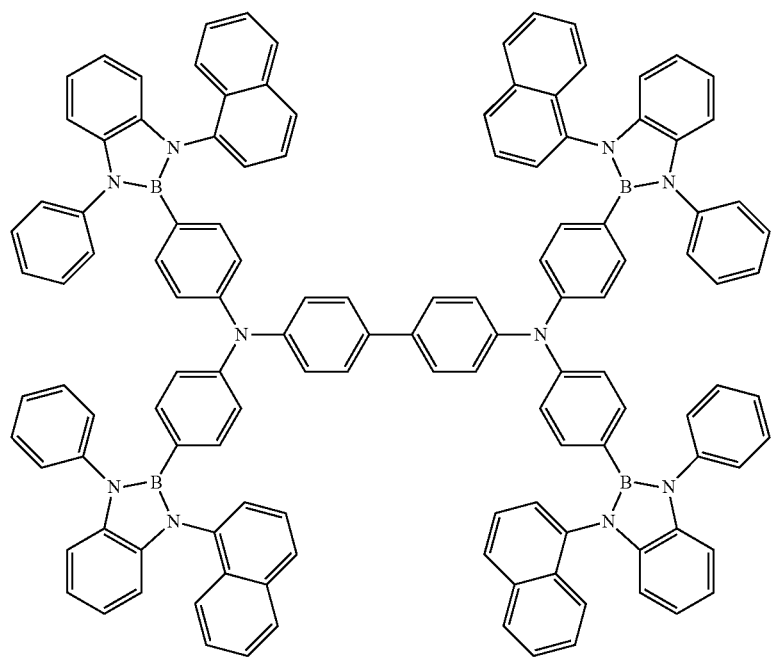
(146)
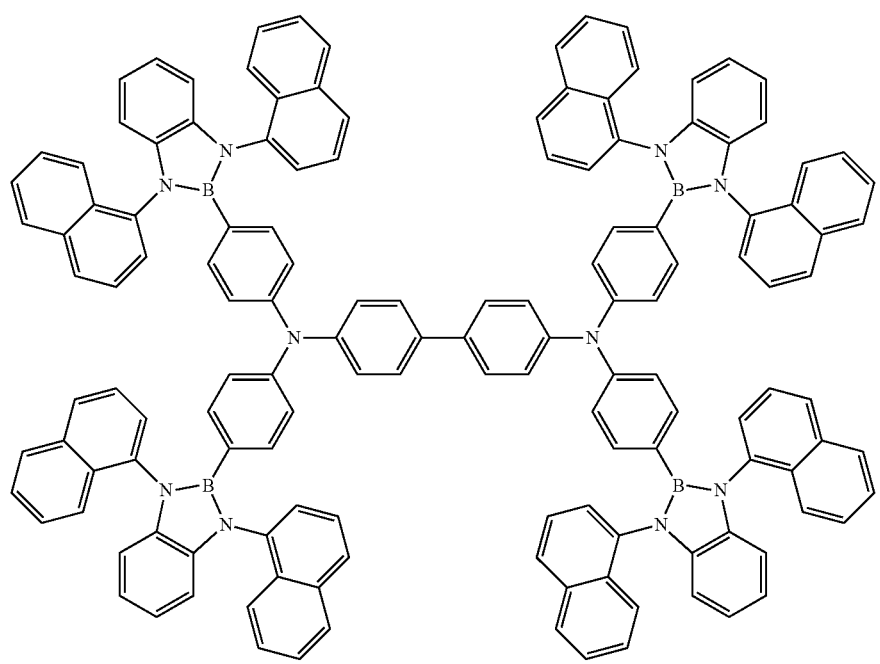

(147)
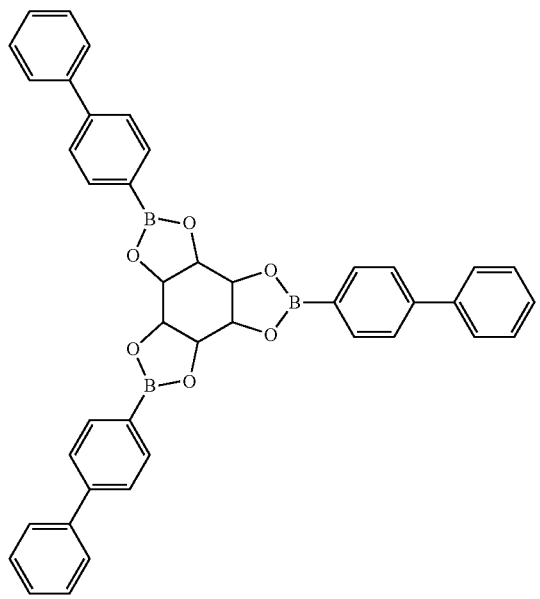
(148)
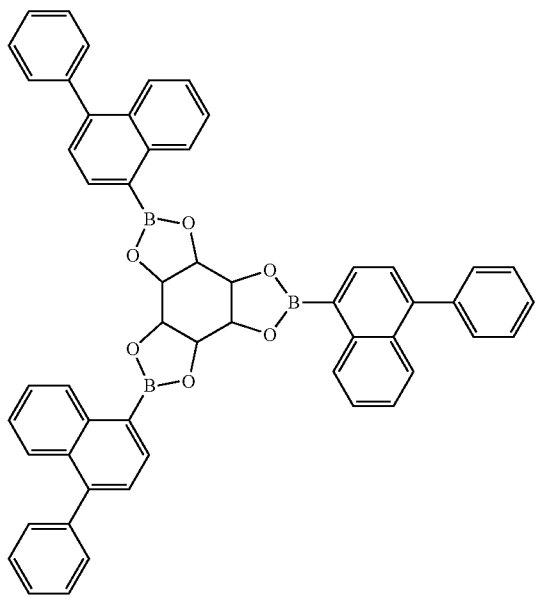
(149)
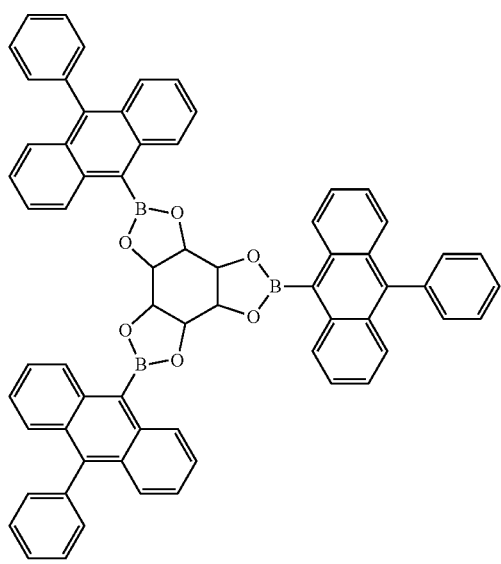
(150)
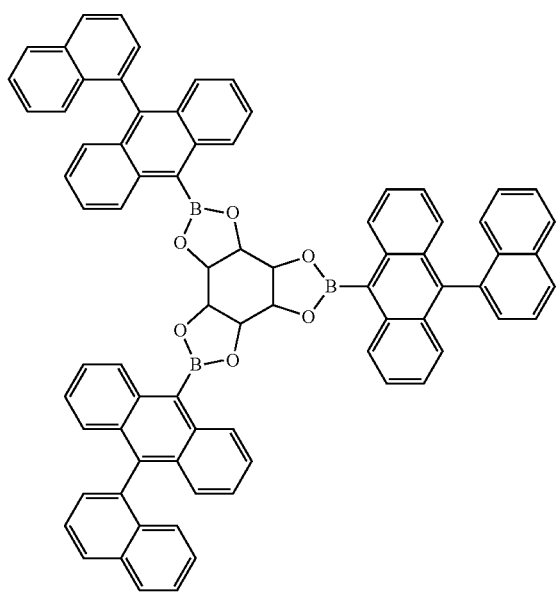

-continued
(151)
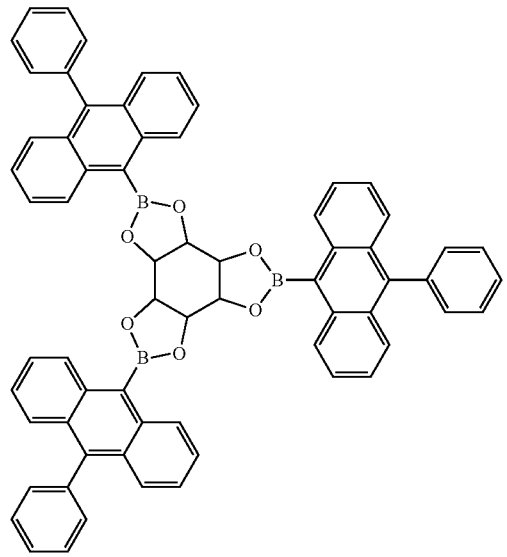
(152)
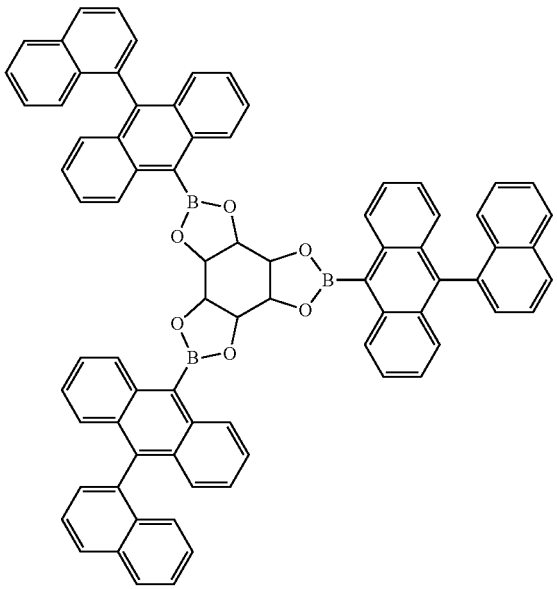
(153)
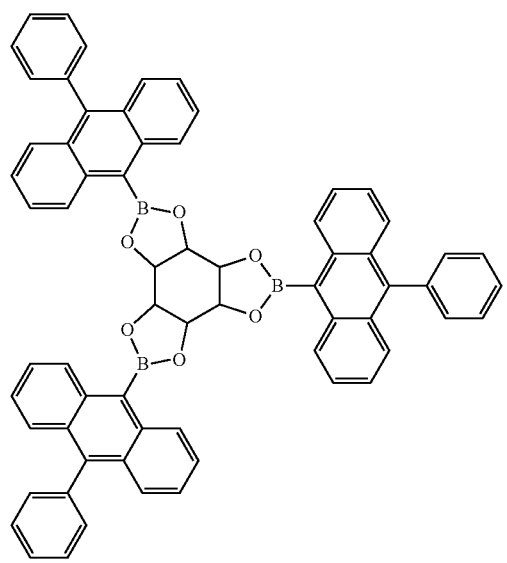
(154)
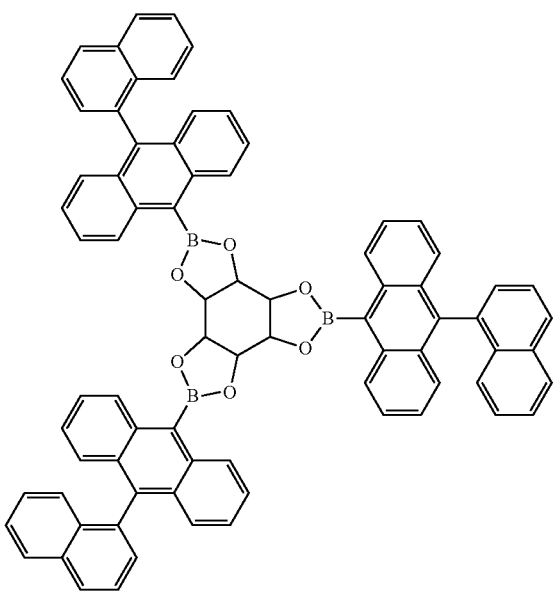
(155)
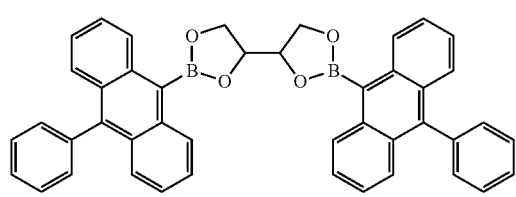
(156)
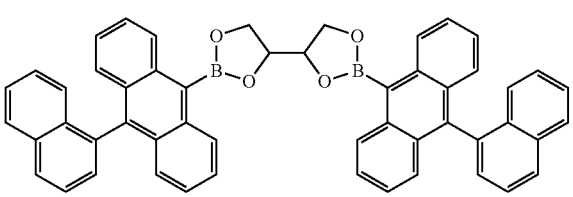
(157)
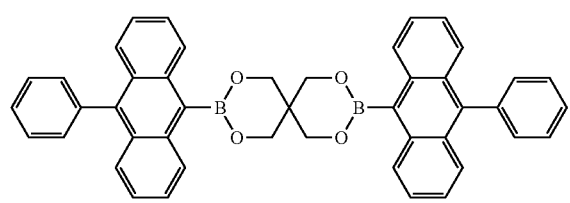
(158)
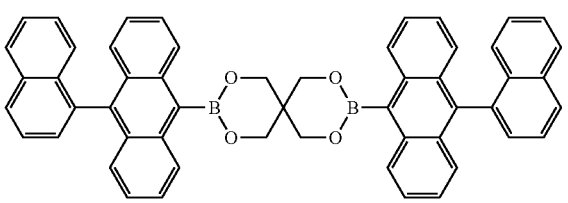

-continued
(159) 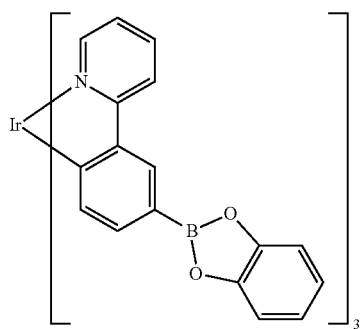
(160) 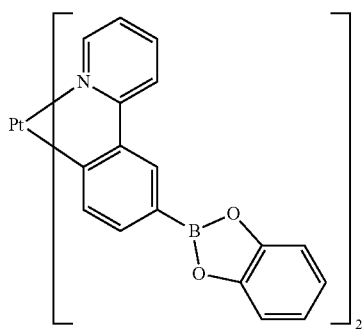
(161) 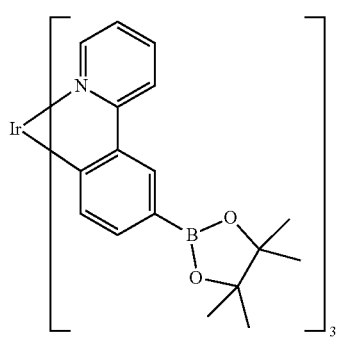
(162) 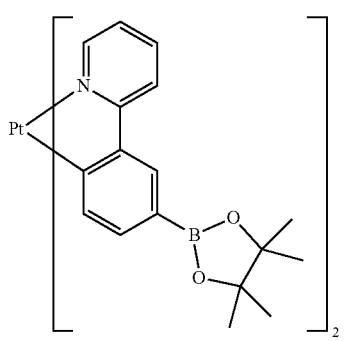
(163) 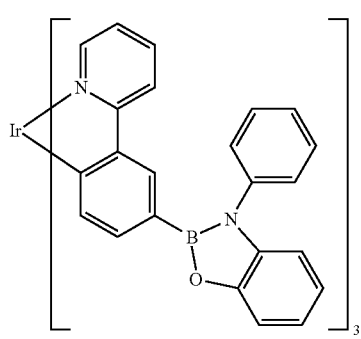
(164) 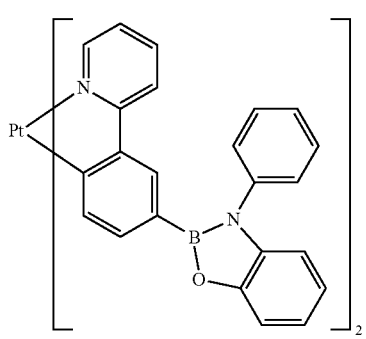
(165) 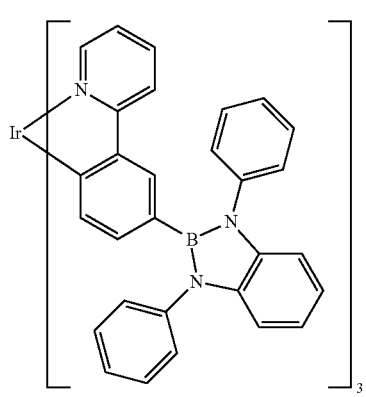
(166) 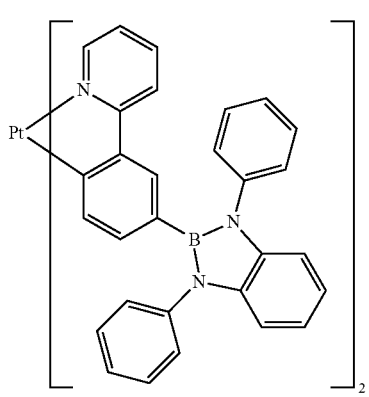

-continued
(167)
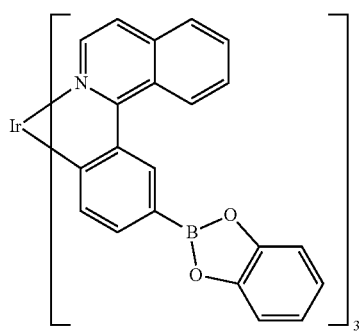
(168)
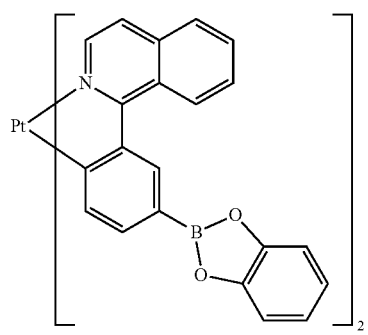
(169)
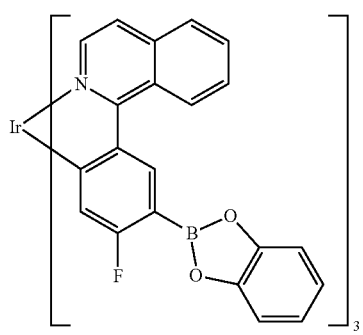
(170)
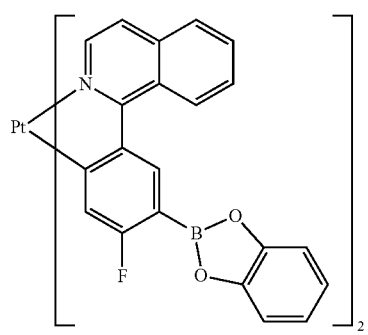
(171)
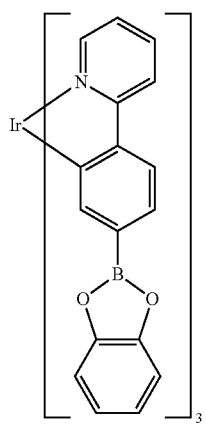
(172)
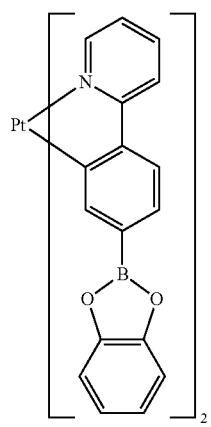
(173)
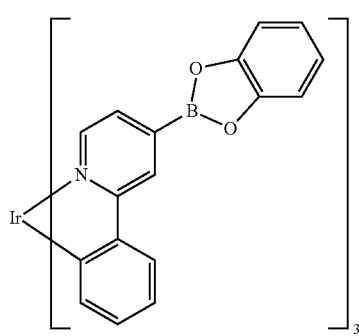
(174)
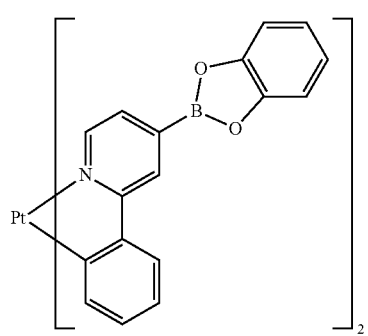

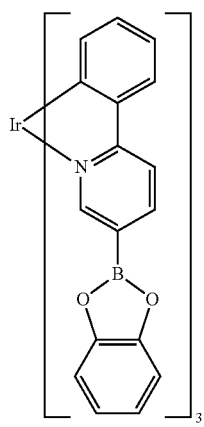
(175)
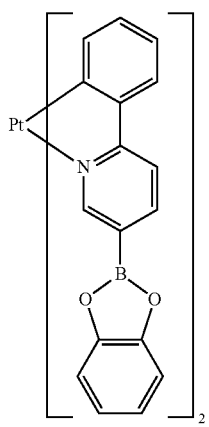
(176)
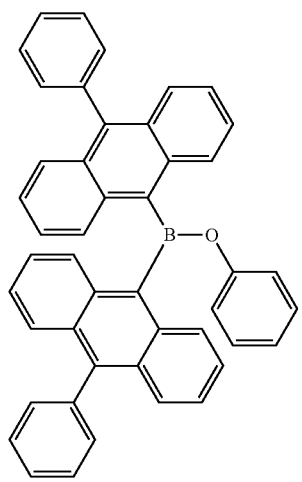
(177)
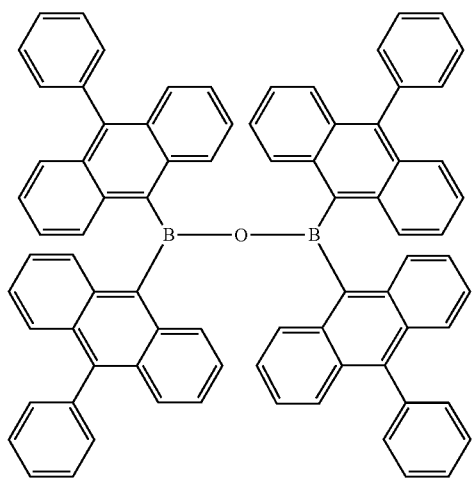
(178)
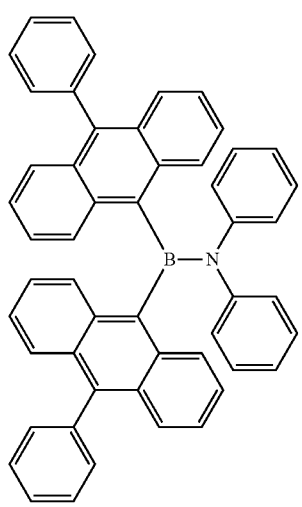
(179)
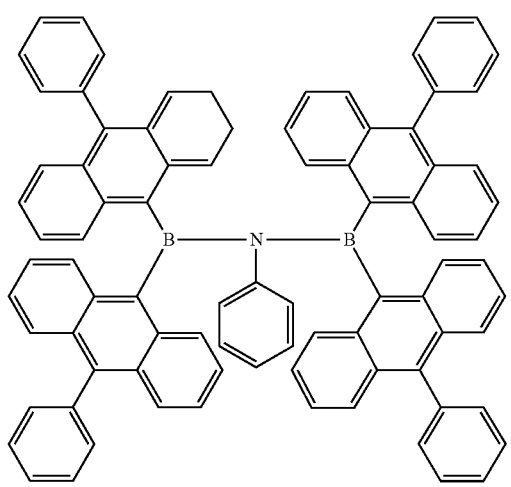
(180)

(181)
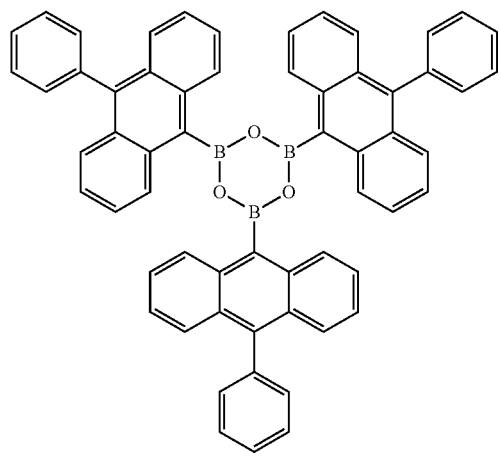
(182)
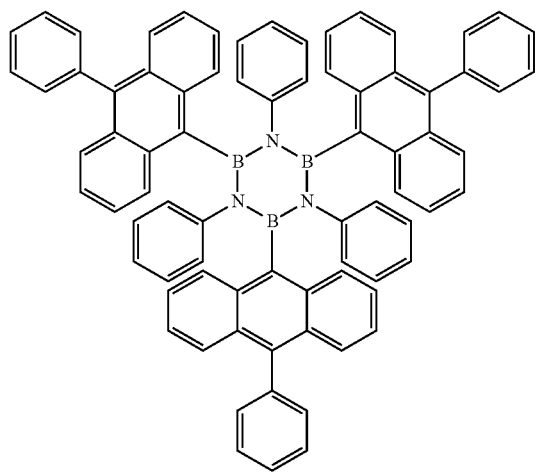
(183)
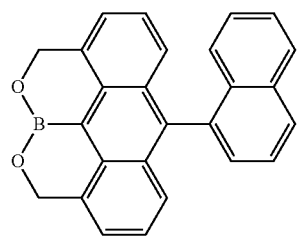
(184)
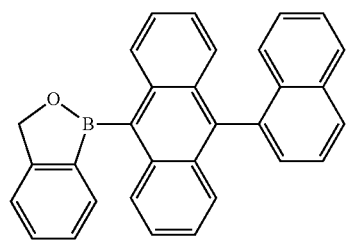
(185)
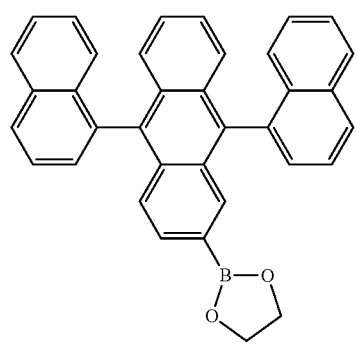
(186)
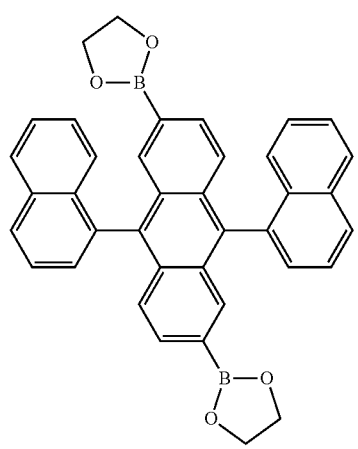

-continued
(187)
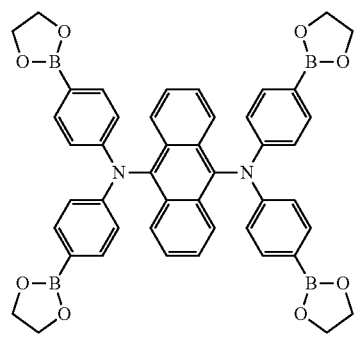
(188)
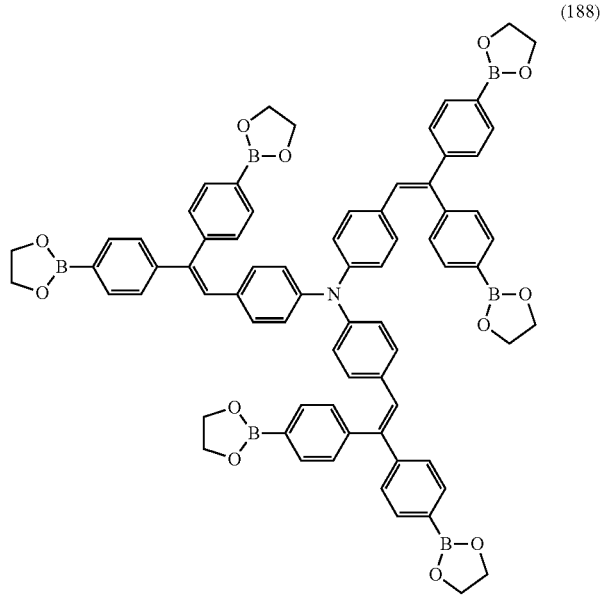
(189)
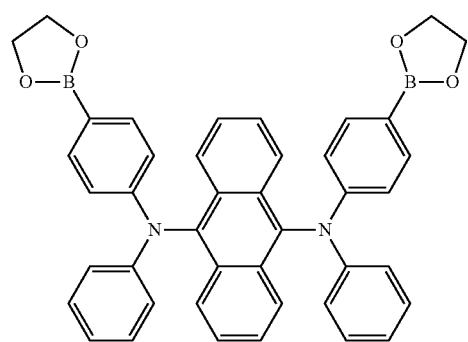
(190)
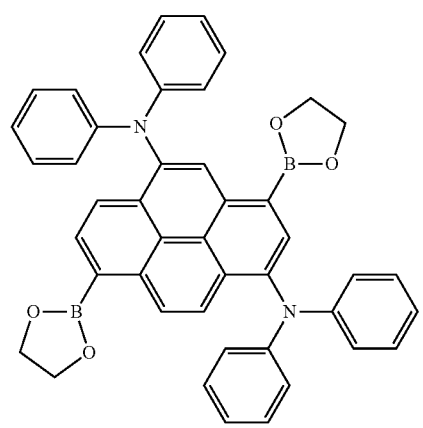
(191)
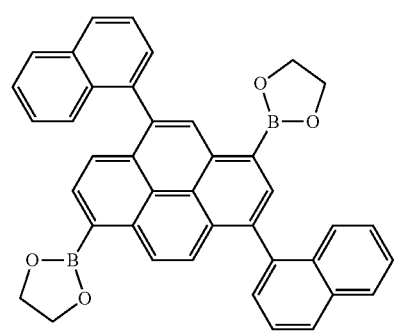
(192)
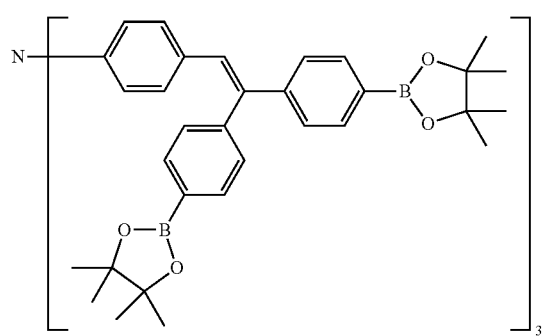

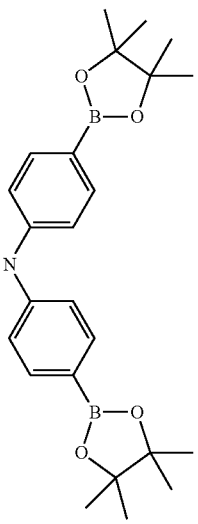
(193)
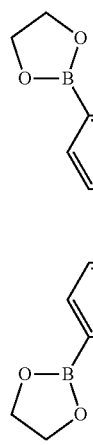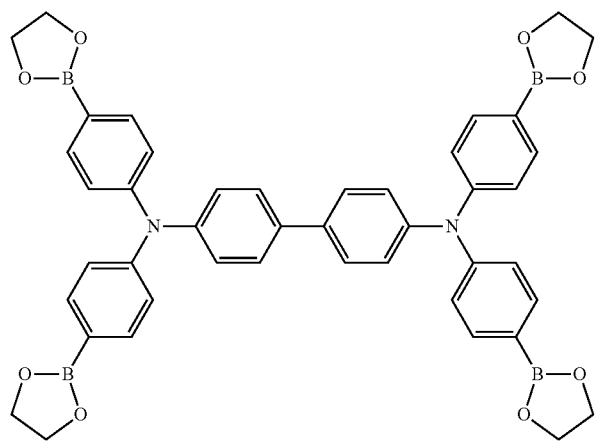
(194)
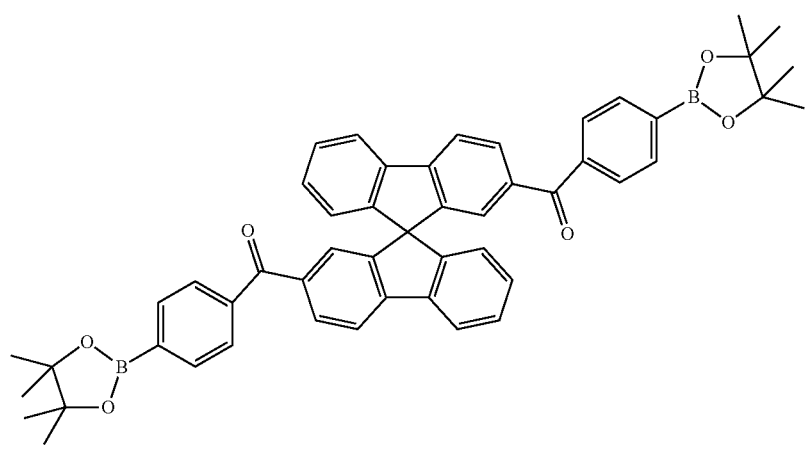
(195)

-continued (196)
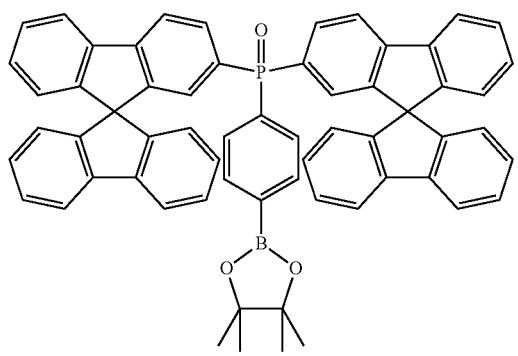

(197)
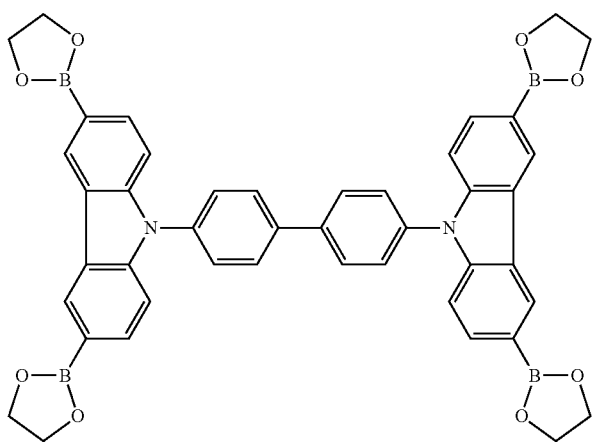

(198)
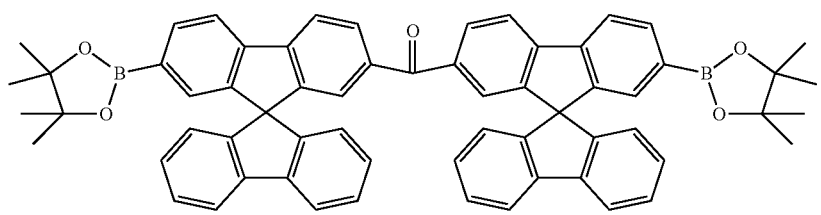

Aromatic boronic acid or borinic acid derivatives and the synthesis thereof are known, in particular, as intermediates for Suzuki coupling reactions. They can be synthesised readily by standard methods of organic chemistry: the synthesis is usually carried out from an aromatic halide, which is converted into an organolithium compound or a Grignard compound, followed by reaction with a trialkyl borate, usually trimethyl borate. The preparation can also be carried out by a one-pot process, in which the aromatic halide is reacted with a reactive metal (Li, Mg, etc.) or an organolithium compound in the presence of the alkyl borate (K.-T. Wong et al., J. Org. Chem. 2002, 67, 1041-1044). The boronic acid obtained by hydrolysis can either be converted into the boronic acid anhydride by dehydration, into the corresponding boronic acid ester by reaction with an alcohol with water separation or into the corresponding boronic acid amide by reaction with an amine. Reaction with a diol gives a cyclic boronic acid ester, while reaction with a diamine results in cyclic boronic acid amides (G. Kaupp et al., Chem. Eur. J. 2003, 9, 4156-4160). Correspondingly, reaction with thiols results in thioboronic acid esters and reaction with dithiols results in cyclic thioboronic acid esters. The alcohols, thiols and amines here may be aromatic or aliphatic. Reaction with aromatic or aliphatic amino alcohols is also possible and results in cyclic boronic acid amidoesters, likewise with aminothiols. Aromatic boronic acid derivatives can furthermore also be obtained by reaction of an aromatic halide with a compound which contains a boron-boron bond (for example bispinacolatodiborane) with palladium catalysis (JP 2004/189705; T. Ishiyama et al., Special Publication—Royal Society of Chemistry 1997, 201 (Advances in Boron Chemistry), 92-95). Another possible synthesis is reaction of the lithiated aromatic compound with chlorocatecholborane derivatives, which results directly in the boronic acid ester (M. Yamashita et al., Angew. Chem. Int. Ed. 2000, 39, 4055-4058). Cyclooligomerisation of borylacetylenes is also described in the literature (A. Goswami et al., Eur. J. Inorg. Chem. 2004, 2635-2645). The borinic acid derivatives can be synthesised analogously to the boronic acid derivatives, with the difference that the stoichiometric ratios between aryl compound and boron compound are selected correspondingly. The compounds are already formed in high purity in the synthesis and can be purified further by standard methods of organic chemistry, in particular by recrystallisation. Due to their high thermal stability, they can also be purified by sublimation without problems. This is of major importance for use in OLEDs, since sublimed compounds are usually employed for this purpose and the compounds are frequently applied by vapour deposition.

The aromatic halide employed as starting compound can either be a commercially available halide, for example an aryl bromide or aryl dibromide. It is furthermore possible first to build up more complex aromatic systems which contain, for example, a plurality of aryl groups. A standard reaction for this purpose is the Suzuki aryl-aryl coupling with palladium catalysis, the Hartwig-Buchwald aryl-N coupling with palladium catalysis or other transition metal-catalysed coupling reactions. In a next step, one of the aromatic rings can be halogenated, for example by bromination using bromine or NBS.

The invention furthermore relates to the use of oligomers, polymers or dendrimers containing aromatic boronic acid or borinic acid derivatives in organic electronic devices, in particular in organic electroluminescent devices, with the proviso that the boronic acid or borinic acid derivative in oligomers or polymers is not bonded to the chain ends of the oligomer or polymer or not only as end group.

The invention furthermore relates to organic electronic devices, in particular organic electroluminescent devices, comprising at least one oligomer, polymer or dendrimer which contains at least one boronic acid or borinic acid derivative, with the proviso that the boronic acid or borinic acid derivative in oligomers or polymers is bonded to at least one point within the main chain and/or side chain and is not bonded to the chain ends of the oligomer or polymer or not only as end group.

The polymers can be conjugated, partially conjugated or non-conjugated polymers. The boronic acid or borinic acid derivatives can be bonded into the main chain and/or into the side chain of the polymer. Polymers used in organic electronic devices are usually conjugated or partially conjugated polymers containing aromatic recurring units. In general, these polymers are synthesised by palladium-catalysed coupling reactions, in particular Suzuki coupling between an aromatic halide and an aromatic boronic acid or an aromatic boronic acid derivative. If the reaction has not taken place completely or end capping has not been carried out, it may be that boronic acids or boronic acid derivatives again remain in the polymer as end group and are also present in the organic electronic device. For the purposes of this invention, polymeric and oligomeric boronic acid or borinic acid derivatives do not encompass polymers which contain the boronic acid or borinic acid derivative bonded to the chain ends of the polymer or oligomer only as end group, since these groups only remain there as impurity from an incomplete reaction. For the purposes of this invention, polymers according to the invention are those which do not contain the boronic acid or borinic acid derivative bonded to a chain end of the polymer or not only as end group, but instead at least at one further point in the polymer which does not represent an end group. This applies equally to oligomers. The minimum boron content in the polymer here is preferably at least 5 ppm, particularly preferably at least 10 ppm, very particularly preferably at least 100 ppm.

A preferred embodiment of the invention involves conjugated or partially conjugated polymers which contain the boronic acid or borinic acid derivative bonded in a side chain of the polymer.

A further preferred embodiment of the invention involves non-conjugated polymers which contain the boronic acid or borinic acid derivative bonded in a side chain of the polymer. In a particularly preferred embodiment, the non-conjugated polymer framework is a derivative of oligomeric or polymeric sugars, for example amylose or amylopectin.

A further preferred embodiment of the invention involves partially conjugated or non-conjugated polymers which comprise the boronic acid or borinic acid derivative in the main chain of the polymer.

Preferred recurring units of the conjugated, partially conjugated or non-conjugated polymer or oligomer are selected from fluorenes (for example in accordance with EP 842208 or WO 00/22026), spirobifluorenes (for example in accordance with EP 707020, EP 894107 or EP 04028865.6), phenylenes (for example in accordance with WO 92/18552), carbazoles (for example in accordance with WO 04/070772 and WO 04/113468), thiophenes (for example in accordance with EP 1028136), dihydrophenanthrenes (for example in accordance with WO 05/014689), indenofluorenes (for example in accordance with WO 04/041901 and WO 04/113412), phenanthrenes (for example in accordance with WO 05/104264), aromatic ketones (for example in accordance with WO 05/040302) or also from a plurality of these units. Phosphorescent metal complexes may also represent recurring units of the polymer (for example in accordance with WO 02/068435 or WO 06/003000.

The Suzuki coupling that is usually used or also the Yamamoto coupling that is occasionally used (coupling of two aromatic halides) is not suitable as synthetic method if the polymer is intended to comprise aromatic boronic acid or borinic acid derivatives and if these units are already present in the monomers since these groups react under the usual polycondensation conditions. The synthesis of such polymers can thus not be carried out under the standard conditions as are generally frequently used for conjugated or partially conjugated polymers. For the synthesis of non-conjugated polymers, standard syntheses can be used, for example the polymerisation of vinylic double bonds which contain the boronic acid or borinic acid derivatives in the side group. A further possible synthesis is the synthesis by standard methods of a conjugated or partially conjugated polymer which contains unprotected or preferably protected alcohol, thiol or amino groups in the side chain. It preferably contains protected alcohol groups, particularly preferably protected diols. After deprotection, these can be reacted with a boronic acid in a polymer-analogous reaction to give the corresponding boronic acid derivative. Still a further synthetic method which results in the production of unconjugated or partially conjugated polymers is the reaction of an aliphatic or aromatic bis(diol), bis(dithiol) or bis(diamine) with an aromatic bisboronic acid in a polycondensation reaction, as shown in scheme 1a, or the reaction of an aromatic compound containing both two hydroxyl, thiol or amino groups and also a boronic acid group, as shown in scheme 1b:

Scheme 1a

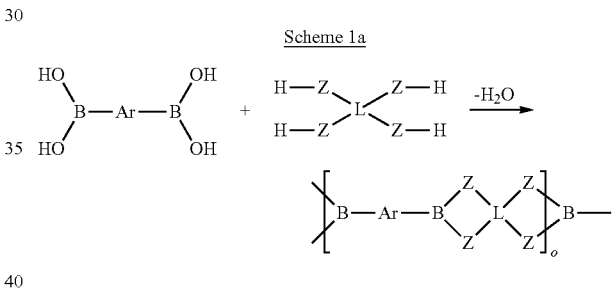

Scheme 1b

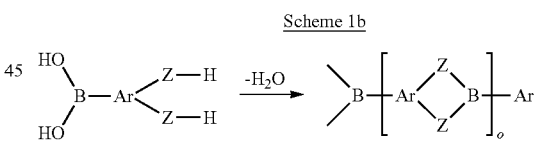

where B, Ar, L and Z have the same meaning as described above, and o on each occurrence, identically or differently, can adopt an integer between 3 and 10,000, preferably between 10 and 1000.

A corresponding reaction is possible using oligoboronic acids and/or oligoalcohols or oligoamines and results in dendrimers or in branched polymer structures.

The process according to scheme 1 is novel and is therefore likewise a subject-matter of the present invention.

It has been found that the compounds of the formulae (9) to (33) are valuable intermediates for carrying out the use according to the invention. These boronic acid and borinic acid derivatives are novel and are therefore also a subject-matter of the present invention.

The invention therefore relates to compounds of the formulae (9) and (9a)

Formula (9)

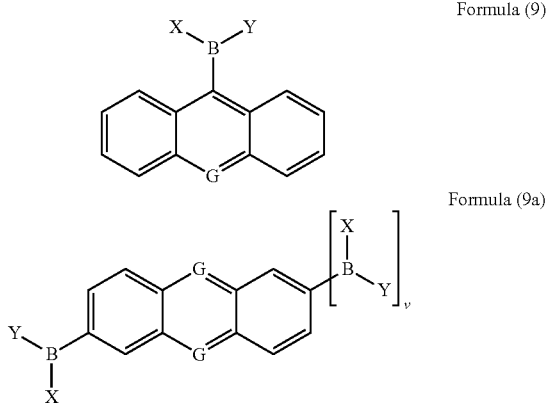

Formula (9a)

where the anthracene or acridine framework may also be substituted by substituents $R^1$ and where B, X, Y and $R^1$ have the same meaning as described above, and furthermore:
G is on each occurrence, identically or differently, C—H, C—$R^1$, C—BXY or N;
v is on each occurrence 0 or 1;
with the exception of the following compounds:

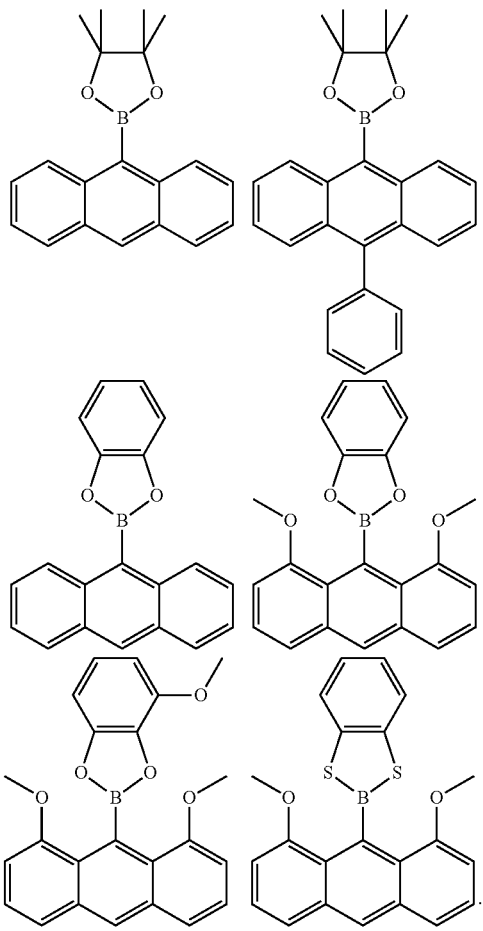

In a preferred embodiment of the formula (9), G stands for C—BXY or for C—$R^1$. G particularly preferably stands for C—$R^1$, where $R^1$ stands for an aromatic or heteroaromatic ring system. The anthracene framework is furthermore preferably unsubstituted apart from in the 9- and 10-positions.

In a preferred embodiment of the formula (9a), G stands for C—$R^1$. $R^1$ here particularly preferably stands for an aromatic or heteroaromatic ring system.

The invention furthermore relates to compounds of the formulae (10) and (11)

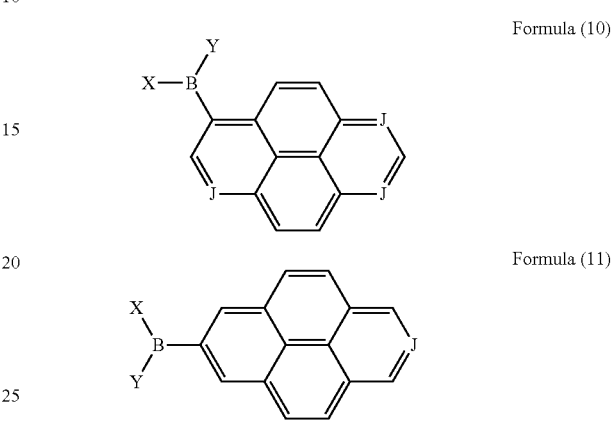

where the pyrene framework may also be substituted by substituents $R^1$ and where B, X, Y and $R^1$ have the same meaning as described above, and furthermore:
J is on each occurrence, identically or differently, C—H, C—$R^1$ or C—BXY;
with the exception of the following compounds:

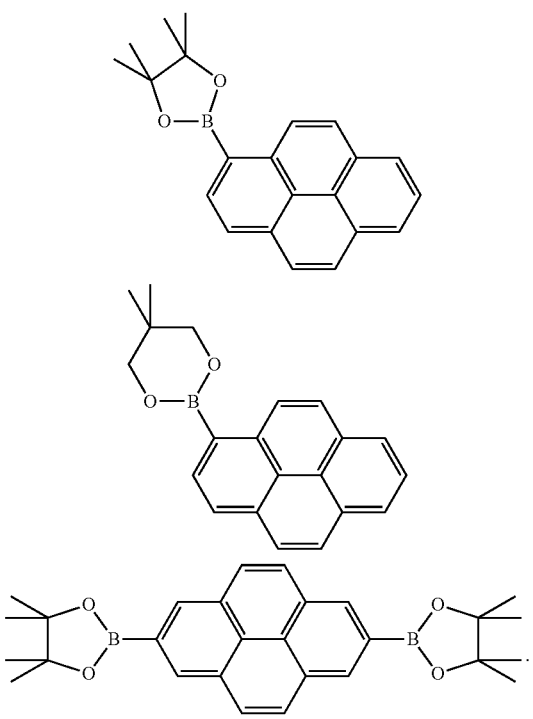

The invention furthermore relates to compounds of the formulae (12) to (17)

Formula (12)

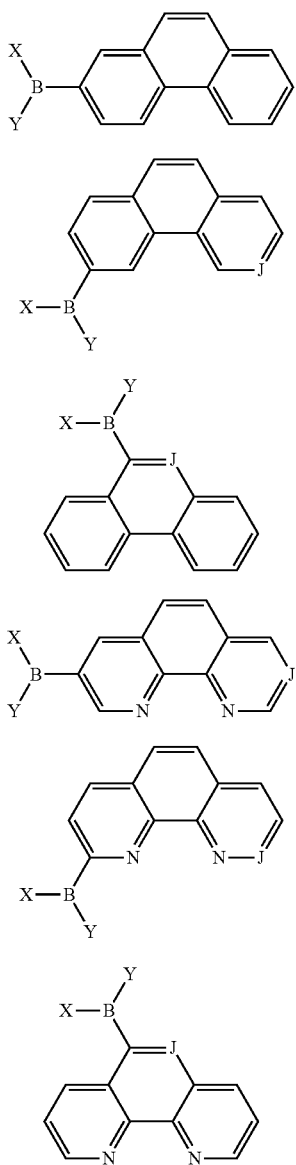

Formula (13)

Formula (14)

Formula (15)

Formula (16)

Formula (17)

where the phenanthrene or phenanthroline framework may also be substituted by substituents $R^1$ and where B, X, Y, J and $R^1$ have the same meaning as described above; with the exception of the following compound:

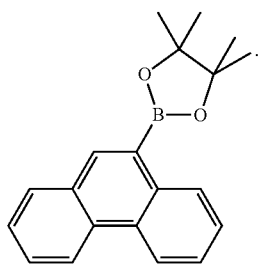 [SMILES: CC1(C)OB(c2cc3ccccc3c3ccccc23)OC1(C)C]

The invention furthermore relates to compounds of the formula (18)

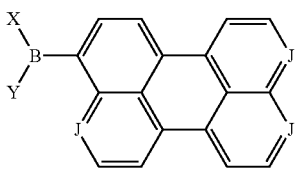

Formula (18)

where the perylene framework may also be substituted by substituents $R^1$ and B, X, Y, J and $R^1$ have the same meaning as described above.

The invention furthermore relates to compounds of the formulae (19) to (23)

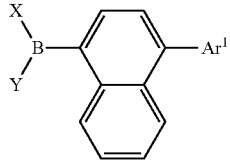

Formula (19)

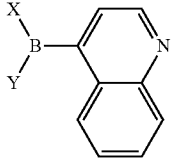

Formula (20)

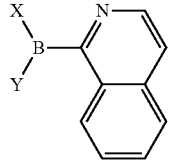

Formula (21)

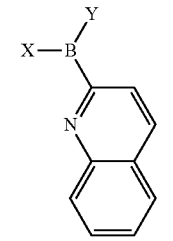

Formula (22)

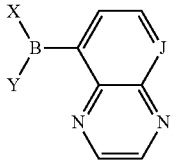

Formula (23)

where the naphthalene, quinoline, isoquinoline or quinoxaline framework may also be substituted by substituents $R^1$ and B, X, Y, J and $R^1$ have the same meaning as described above, and $Ar^1$ represents an aryl or heteroaryl group having 5 to 40 aromatic ring atoms, which may also be substituted by $R^1$.

The invention furthermore relates to compounds of the formulae (24) and (25)

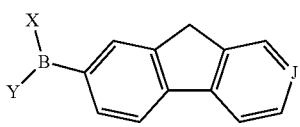

Formula (24)

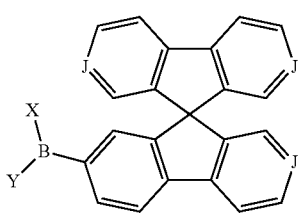

Formula (25)

where the fluorene or spirobifluorene system may also be substituted by substituents $R^1$ and B, X, Y, J and $R^1$ have the same meaning as described above, with the proviso that for $X=OR^2$ and $Y=OR^2$, the two radicals $R^2$ form an aromatic ring system with one another.

The compound of the formula (24) is preferably substituted in the 9,9-position by two substituents $R^1$ and is otherwise unsubstituted. The compound of the formula (25) is preferably unsubstituted or only carries substituents in one or more of positions 2, 7, 2' and 7'.

The invention furthermore relates to compounds of the formula (26)

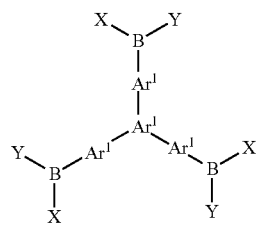

Formula (26)

where B, X, Y, $Ar^1$ and $R^1$ have the same meaning as described above.

The invention furthermore relates to compounds of the formula (27) and (27a)

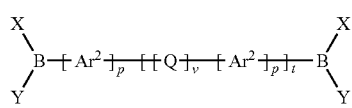

Formula (27)

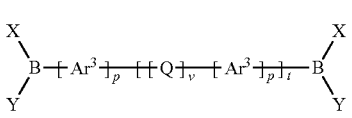

Formula (27a)

where B, X, Y, Ar and $R^1$ have the same meaning as described above and furthermore:
$Ar^2$ is on each occurrence, identically or differently, a fused aryl or heteroaryl group having 9 to 20 aromatic ring atoms, which may be substituted by $R^1$;
$Ar^3$ is on each occurrence, identically or differently, a fluorene or spirobifluorene group, which may be substituted by $R^1$;
Q is on each occurrence, identically or differently, a divalent unit selected from Ar, O, S, SO, $SO_2$, Se, SeO, $SeO_2$, Te, TeO, $TeO_2$, NAr, PAr, P(=O)Ar, AsAr, As(=O)Ar, SbAr, Sb(=O)Ar, $C(R^1)_2$, C=O, $Si(R^1)_2$ and O—BAr—O;
p is on each occurrence, identically or differently, 1, 2, 3, 4, 5 or 6;
v is on each occurrence, identically or differently, 0 or 1;
t is 1, 2, 3, 4 or 5;
with the proviso that $Ar^2$ in the formula (27) is not naphthyl on each occurrence if all p=1 and at the same time v=0 and t=1.

$Ar^2$ is preferably on each occurrence, identically or differently, a fused aryl or heteroaryl group having 9 to 20 C atoms, particularly preferably a fused aryl group having 10 to 16 C atoms.

p is furthermore preferably 2, 3, 4 or 5, particularly preferably 2, 3 or 4, very particularly preferably 2 or 3.

The invention furthermore relates to compounds of the formula (28)

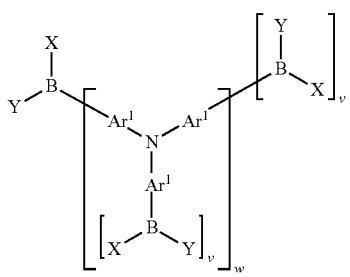

Formula (28)

where B, X, Y, $Ar^1$ and $R^1$ have the same meaning as described above, and furthermore:
v is on each occurrence, identically or differently, 0 or 1;
w is on each occurrence, identically or differently, 1, 2, 3, 4, 5 or 6;
with the proviso that boronic acid esters formed with pinacol, 1,2-ethanediol, 2,2-dimethyl-1,3-propanediol, 2,3-butanediol and isopropanol are excluded from the invention.

The invention furthermore relates to compounds of the formulae (29), (29a) and (29b)

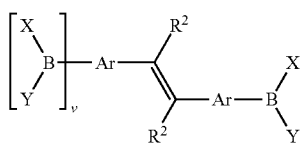

Formula (29)

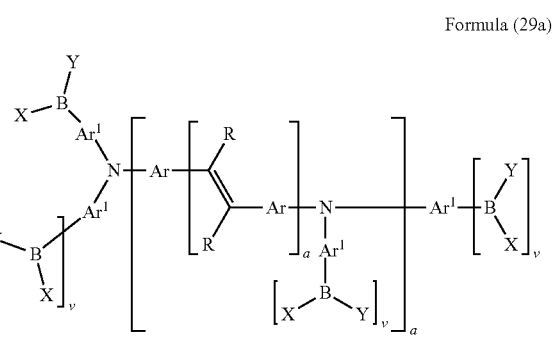

Formula (29a)

Formula (29b)

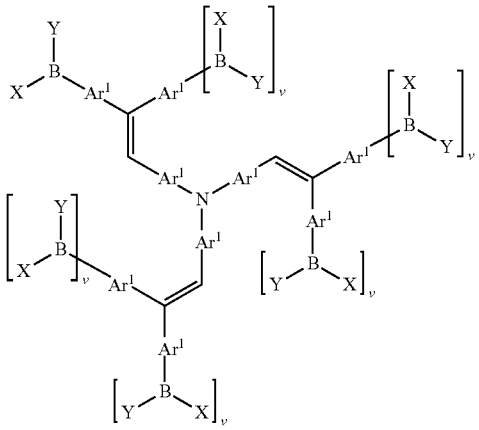

where B, X, Y, Ar, $R^1$, $R^2$ and v have the same meaning as described above, and where a on each occurrence, identically or differently, stands for 1, 2 or 3, with the proviso that structures of the formula (29) are not boronic acid esters of pinacol, glycol and/or 1,3-propanediol.

The symbol Ar or $Ar^1$ here preferably stands for a group which is derived from benzene, biphenyl or naphthalene, each of which may be substituted by $R^1$ or unsubstituted.

The invention furthermore relates to compounds of the formula (30), formula (31), formula (32) or formula (33)

Formula (30)

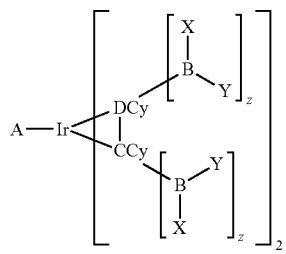

Formula (31)

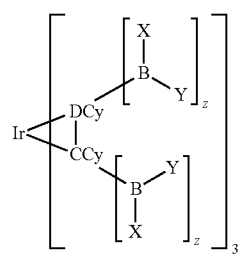

Formula (32)

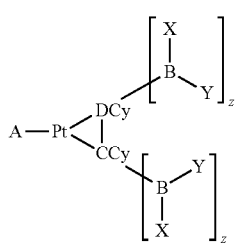

Formula (33)

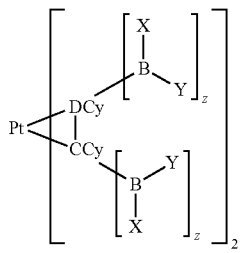

where B, X, Y, Z, Ar, $R^1$, $R^2$ and $R^3$ have the same meaning as described above, and furthermore:

DCy is on each occurrence, identically or differently, a cyclic group which contains at least one donor atom, preferably nitrogen or phosphorus, via which the cyclic group is bonded to the metal and which may in turn carry one or more substituents $R^1$; the groups DCy and CCy are bonded to one another via at least one covalent bond;

CCy is on each occurrence, identically or differently, a cyclic group which contains a carbon atom via which the cyclic group is bonded to the metal and which may in turn carry one or more substituents $R^1$;

A is on each occurrence, identically or differently, a monoanionic ligand which chelates in a bidentate manner, preferably a diketonate ligand;

z is on each occurrence, identically or differently, 0, 1, 2, 3, 4, 5 or 6, with the proviso that at least one z in each complex is other than 0 and furthermore with the proviso that z cannot adopt a number which is greater than the maximum number of substitutable hydrogen atoms on the corresponding ring DCy or CCy.

In a preferred embodiment of the invention, the group DCy is a monocyclic group having 5 or 6 aromatic ring atoms or a fused group having 9 or 10 aromatic ring atoms, particularly preferably selected from pyridine, pyrimidine, pyridazine, pyrazine, triazine, quinoline, isoquinoline, quinoxaline and benzopyrimidine; DCy particularly preferably stands for pyridine, quinoline or isoquinoline. These groups may each be substituted by $R^1$.

The group CCy is furthermore preferably a monocyclic group having 5 or 6 aromatic ring atoms or a fused group having 9 or 10 aromatic ring atoms, particularly preferably selected from benzene, naphthalene, anthracene, thiophene, benzothiophene, pyrrole and indole; CCy particularly preferably stands for benzene or naphthalene. These groups may each be substituted by $R^1$.

Although evident from the above description, it should again explicitly be emphasised that a plurality of radicals $R^1$ can form a ring system with one another. Radicals $R^1$ on the groups CCy and DCy can thus also connect these two rings via a further bridge.

The same preferences as already described above apply to the groups X and Y. Compounds of the formulae (5) to (33) can likewise be reacted with oligoalcohols, oligoamines or oligoaminoalcohols in order thus to obtain dimers, trimers, tetramers, etc. These are likewise a subject-matter of the present invention.

The invention again furthermore relates to oligomers, polymers and dendrimers comprising at least one boronic acid or borinic acid derivative, with the proviso that the boronic acid or borinic acid derivative in polymers and oligomers is not bonded to a chain end of the polymer or not only as end group.

The same preferences as already described above for the use of these compounds apply to the polymers, oligomers and dendrimers according to the invention.

The devices described above have the following surprising advantages over the prior art:
1. The stability of corresponding devices is higher compared with systems in accordance with the prior art, which is evident, in particular, from a longer lifetime of the OLEDs.
2. The boronic acid or borinic acid derivatives exhibit only a very small Stokes shift. The emission spectrum of the boronic acid or borinic acid derivative used as host thus has considerable overlap with the absorption spectrum of the dopant. The overlap of emission and absorption spectra is a prerequisite for good energy transfer to the dopant and thus for high efficiency.
3. In contrast to compounds used to date, some of which were difficult to purify owing to their poor solubility, the boronic acid and borinic acid derivatives are readily soluble and therefore simpler to purify or easier to process from solution.
4. The boronic acid or borinic acid derivatives employed can readily be synthesised by standard methods of organic chemistry and are easy to purify. They thus represent an advantage over compounds employed in accordance with the prior art.
5. The boronic acid and borinic acid derivatives have a lower evaporation temperature than comparable compounds which do not carry these substituents. This is of major advantage for the production of OLEDs by vacuum vapour deposition since thermally sensitive parts of the apparatus, such as, for example, the shadow masks, are thus heated to a smaller extent.
6. The boronic acid and borinic acid derivatives, in particular of triplet emitters, have higher thermal stability than corresponding compounds, in particular triplet emitters, in accordance with the prior art which are unsubstituted or substituted in accordance with the prior art only by alkyl or aryl groups, halogens, etc. Due to the higher sublimation stability, they are easier to process, in particular by sublimation during device production, which means a significant advantage over the materials in accordance with the prior art.
7. The boronic acid and borinic acid derivatives are significantly more stable to oxidation than boranes as employed in accordance with the prior art. They are thus easier to handle and are therefore more suitable for industrial use than aromatic boranes in accordance with the prior art.

The present application text and also the following examples are directed to the use of boronic acid or borinic acid derivatives in relation to OLEDs and the corresponding displays. In spite of this restriction, it is readily possible for the person skilled in the art, without inventive step, also to use boronic acid or borinic acid derivatives for further uses in other electronic devices.

The invention is explained by the following examples without wishing to be restricted thereby.

BRIEF DESCRIPTION OF THE DRAWING

The absorption and photoluminescence spectrum of anthracene-9,10-bis(boronic acid glycol ester) is shown in FIG. 1.

EXAMPLES

The following syntheses are carried out under a protective-gas atmosphere, unless indicated otherwise. The starting materials (9-bromoanthracene, 4-methylnaphth-1-ylboronic acid, 9,10-dibromoanthracene, ethylene glycol, pinacol, hexafluoro-2,3-bis(trifluoromethyl)butane-2,3-diol, pinacolborane, 1,4-dibromonaphthalene, p-xylene diethyl phosphonate, N,N,N',N'-tetraphenylbenzidine, 4-bromobenzoyl chloride, DPEPhos, inorganics, solvents) can be obtained from ALDRICH, Lancaster, Sensient, Strem or ABCR. Dibromopyrene (isomer mixture) can be prepared by the method of Minabe et al., *Bull. Chem. Soc. Jpn.* 1994, 67(1), 172, 2,6-dibromoanthraquinone can be prepared by the method of Lee et al., *Org. Lett.* 2005, 7(2), 323, bis(4-bromophenyl)methyl diethyl phosphonate can be prepared in accordance with JP 09003079, bis(4-bromophenyl) (4-formylphenyl)amine can be prepared by the method of Holmberg et al., *Poly. Mat. Sci. Engen.* 2001, 84, 717, 4-bromophenylphosphorus dibromide can be prepared by the method of Hinke et al., *Phos. Sulf. Rel. El.* 1983, 15(1), 93; fac-tris[2-(2-pyridinyl-κN)(5-bromophenyl)-κC]-iridium(III), fac-tris[2-(2-pyridinyl-κN)(4-fluoro-5-bromophenyl)-κC]-iridium(III) and fac-tris[2-(1-isoquinolinyl-κN)(5-bromophenyl)-κC]-iridium(III) are prepared in accordance with/analogously to WO 02/068435 (Example 4).

Example 1

Synthesis of anthracene-9,10-bis(boronic acid glycol ester)

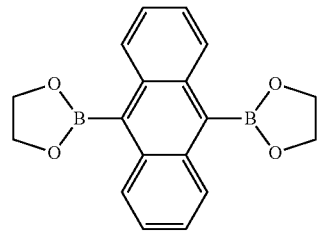 [SMILES: c1ccc2c(B3OCCO3)c3ccccc3c(B3OCCO3)c2c1]

428.0 ml (1.07 mol) of n-butyllithium (2.5M in n-hexane) are added over the course of 20 min. to a vigorously stirred suspension, cooled to −78° C., of 150.0 g (446 mmol) of 9,10-dibromoanthracene in 2000 ml of diethyl ether, and the mixture is subsequently stirred at −78° C. for 30 min. The suspension is allowed to warm to 20° C. over the course of 2 h, stirred at 20° C. for a further 2 h and re-cooled to −78° C. 199.0 ml (1.78 mol) of trimethyl borate are added over the course of 5 min. with vigorous stirring, and the suspension is allowed to re-warm to 20° C. After 15 h at 20° C., a mixture of 67.0 ml (1.12 mol) of acetic acid in 300 ml of water is added, and the mixture is stirred at room temperature for a further 5 h. After the water phase has been separated off, the organic phase is evaporated to dryness under reduced pressure. 500 ml of n-hexane are added to the slurry which remains, and the mixture is stirred vigorously for 1 h. The solid formed is subsequently filtered off with suction, washed twice with 200 ml of n-hexane and sucked dry. The solid is suspended in 500 ml of toluene, 60 ml of ethylene glycol are added, and the mixture is boiled on a water separator for 5 h. The crystals deposited after cooling of the toluene solution are filtered off with suction, recrystallised a further twice from toluene and subsequently sublimed (T=240° C., p=5×10$^{-5}$ mbar). Yield: 71.3 g (50.3% of theory), 99.9% according to $^1$H-NMR. The absorption and photoluminescence spectrum of anthracene-9,10-bis(bo-

Example 2

Synthesis of 10-(4-methylnaphth-1-yl)anthracene-9-boronic acid pinacol ester a) 9-(4-Methylnaphth-1-yl)anthracene

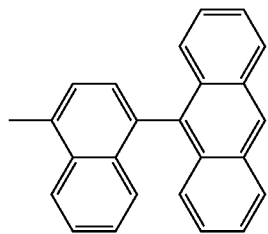 [SMILES: Cc1ccc(-c2c3ccccc3cc3ccccc23)c2ccccc12]

3.6 g (11.7 mmol) of tri-o-tolylphosphine and then 437 mg (1.9 mmol) of palladium(II) acetate are added with vigorous stirring to a suspension of 93.0 g (500 mmol) of 4-methylnaphthalene-1-boronic acid, 100.0 g (389 mmol) of 9-bromoanthracene, 212.3 g (1 mol) of tripotassium phosphate in a mixture of 400 ml of dioxane, 600 ml of toluene and 1000 ml of water, and the mixture is refluxed for 16 h. After the reaction mixture has been cooled, the organic phase is separated off and washed three times with 500 ml of water. The organic phase is subsequently filtered through silica gel and evaporated to dryness. The oil which remains is taken up in 1000 ml of ethanol and dissolved under reflux. After cooling, the colourless solid is filtered off with suction, again washed by stirring with 1000 ml of ethanol and finally dried under reduced pressure. Yield: 103.0 g (83.1% of theory), about 96% according to $^1$H-NMR.

b) 9-Bromo-10-(4-methylnaphth-1-yl)anthracene

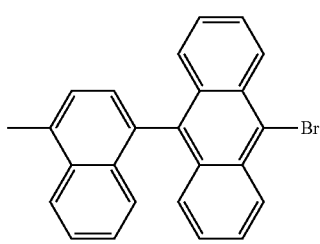 [SMILES: Cc1ccc(-c2c3ccccc3c(Br)c3ccccc23)c2ccccc12]

A mixture of 18.0 ml (352 mmol) of bromine in 100 ml of dichloromethane is added dropwise with vigorous stirring to a solution of 102.0 g (320 mmol) of 9-(4-methylnaphth-1-yl)anthracene in 2000 ml of dichloromethane at −5° C., and the mixture is stirred at room temperature for 12 h. The suspension is subsequently diluted with 1000 ml of ethanol. The precipitated solid is filtered off with suction, washed with 500 ml of a mixture of water and ethanol (1:1, v:v) and three times with 200 ml of ethanol. After washing twice with 1000 ml of boiling ethanol each time, the solid is dried under reduced pressure. Yield: 108.0 g (84.9% of theory), about 97% according to $^1$H-NMR.

c) 10-(4-Methylnaphth-1-yl)anthracene-9-boronic acid pinacol ester

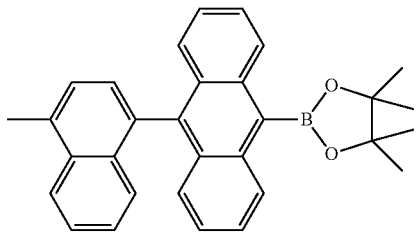

44.0 ml (110 mmol) of n-butyllithium (2.5M in n-hexane) are added over the course of 20 min. to a vigorously stirred suspension, cooled to −78° C., of 39.7 g (100 mmol) of 9-bromo-10-(4-methylnaphth-1-yl)anthracene in 1000 ml of diethyl ether, and the mixture is subsequently stirred at −78° C. for 30 min. The suspension is allowed to warm to 20° C. over the course of 2 h, is stirred at 20° C. for a further 2 h and re-cooled to −78° C. 28.0 ml (250 mol) of trimethyl borate are added over the course of 5 min. with vigorous stirring, and the suspension is allowed to re-warm to 20° C. After 15 h at 20° C., a mixture of 15.0 ml (250 mol) of acetic acid in 200 ml of water is added, and the mixture is stirred at room temperature for a further 5 h. After the water phase has been separated off, the organic phase is evaporated to dryness under reduced pressure. 300 ml of n-hexane are added to the slurry which remains, and the mixture is stirred vigorously for 1 h. The solid formed is subsequently filtered off with suction, washed twice with 100 ml of n-hexane and sucked dry. The solid is suspended in 150 ml of toluene, 13.0 g (110 mmol) of pinacol are added, and the mixture is boiled on a water separator for 5 h. The crystals deposited after cooling of the toluene solution are filtered off with suction, recrystallised twice from DMSO and subsequently sublimed (T=350° C., p=5×10$^{-5}$ mbar); yield: 30.4 g (68.4% of theory), 99.9% according to $^1$H-NMR.

Example 3

Synthesis of 9,10-bis(phenyl-2-boronic acid pinacol ester)anthracene a) 9,10-Bis(2-bromophenyl)anthracene

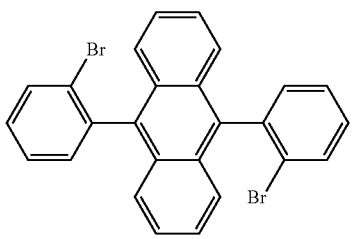 [SMILES: Brc1ccccc1-c1c2ccccc2c(-c2ccccc2Br)c2ccccc12]

6.7 g (5.8 mmol) of tetrakis(triphenylphosphino)palladium(0) are added to a solution of 149.0 ml (1.2 mol) of 1,2-dibromobenzene, 98.0 g (308 mmol) of 9,10-anthracenediboronic acid ethylene glycol ester and 179.0 g (3.1 mol) of potassium fluoride (anhydrous, spray-dried) in a mixture of 1300 ml of dioxane, 350 ml of ethanol and 950 ml of water, and the mixture is refluxed for 120 h. After cooling, the precipitated solid is filtered off with suction, washed three times with 100 ml of water each time and three times with 100 ml of ethanol each time and dried under reduced pressure. Yield: 64.3 g (132 mmol), 42.8% of theory; purity 98% according to $^1$H-NMR, atropisomerically pure.

b) Synthesis of 9,10-bis(phenyl-2-boronic acid pinacol ester)anthracene

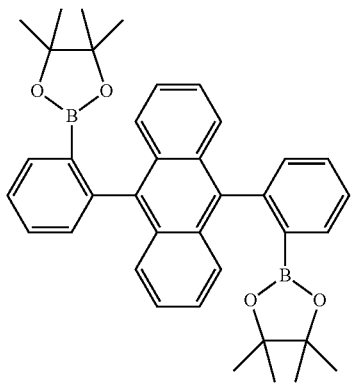 [SMILES: CC1(C)OB(c2ccccc2-c2c3ccccc3c(-c3ccccc3B3OC(C)(C)C(C)(C)O3)c3ccccc23)OC1(C)C]

40.0 ml of n-BuLi (2.5M in hexane) are added to a suspension of 19.5 g (40 mmol) of 9,10-bis(2-bromophenyl)anthracene in 1000 ml of diethyl ether, and the mixture is stirred at room temperature for 6 h. The reaction mixture is subsequently cooled to −78° C., and 26.8 ml (240 mmol) of trimethyl borate are added rapidly with vigorous stirring. After slow warming to room temperature, a mixture of 8 ml of acetic acid and 300 ml of water and then 500 ml of ethyl acetate are added, the mixture is stirred at room temperature for a further 1 h, and the organic phase is separated off, washed twice with 500 ml of water and evaporated under reduced pressure. 300 ml of toluene and 10.6 g (90 mmol) of pinacol are added to the residue, and the mixture is heated on a water separator. When the separation of water is complete, 250 ml of toluene are distilled off, and 300 ml of ethanol are added. After cooling, the colourless solid is filtered off with suction, recrystallised three times from toluene and dried under reduced pressure. Sublimation, p=1×10$^{-5}$ mbar, T=260° C. Yield: 10.6 g (18 mmol), 45.5% of theory; purity: 99.9% according to $^1$H-NMR.

Example 4

Synthesis of 1,2-bis(anthracen-9-yl-10-boronic acid pinacol ester)benzene a) 1,2-Bis(anthracen-9-yl)benzene

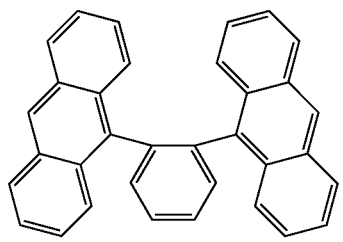 [SMILES: c1ccc(-c2c3ccccc3cc3ccccc23)c(-c2c3ccccc3cc3ccccc23)c1]

Procedure analogous to Example 3a. Instead of 149.0 ml (1.2 mol) of 1,2-dibromobenzene and 98.0 g (308 mmol) of 9,10-anthracenediboronic acid ethylene glycol ester, 12.1 ml (100 mmol) of dibromobenzene and 68.0 g (306 mmol) of 9-anthraceneboronic acid are used. After cooling, the solid is filtered off with suction, washed three times with 100 ml of ethanol each time and then washed twice by stirring with 1000 ml of refluxing acetic acid each time (1 h) and each time filtered off with suction after cooling to 90° C. The mother liquor is discarded in each case. The solid is finally washed once with boiling ethanol. Yield: 33.0 g (76 mmol), 76.6% of theory; purity: 98% according to $^1$H-NMR.

b) 1,2-Bis(10-bromoanthracen-9-yl)benzene

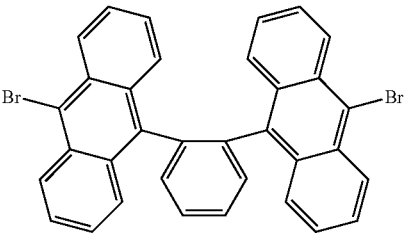 [SMILES: Brc1c2ccccc2c(-c2ccccc2-c2c3ccccc3c(Br)c3ccccc23)c2ccccc12]

142.4 g (800 mmol) of N-bromosuccinimide are added with exclusion of light to a suspension of 86.1 g (200 mmol) of 1,2-bis(anthracen-9-yl)benzene and 500 g of glass beads (diameter 4 mm) in 2000 ml of THF, stirred by a precision glass stirrer. The mixture is stirred at room temperature for 24 h, then the glass beads are filtered off via a sieve and washed with THF, and the solid is filtered off from the THF, washed three times with 200 ml of ethanol each time and then dried under reduced pressure. Yield: 114.1 g (194 mmol), 97.0% of theory; purity: 97% according to $^1$H-NMR.

c) 1,2-Bis(anthracen-9-yl-10-boronic acid pinacol ester)benzene

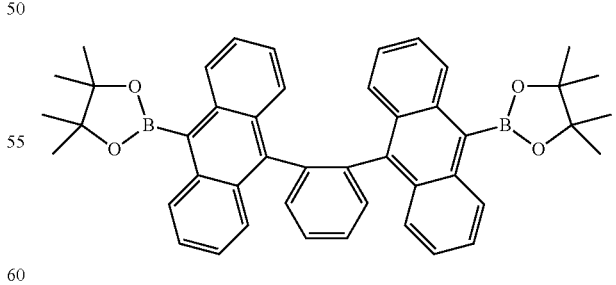

Preparation analogous to Example 3b. Instead of 19.5 g (40 mmol) of 9,10-bis(2-bromophenyl)anthracene, 23.5 g (40 mmol) of 1,2-bis(10-bromoanthracen-9-yl)benzene are used. Sublimation at p=1×10$^{-5}$ mbar, T=310° C. Yield: 17.1 g (25 mmol), 62.6% of theory; purity: 99.9% according to $^1$H-NMR.

Example 5

Synthesis of 1,4-bis(anthracen-9-yl-10-boronic acid pinacol ester)naphthalene a) 1,4-Bis(anthracen-9-yl)naphthalene

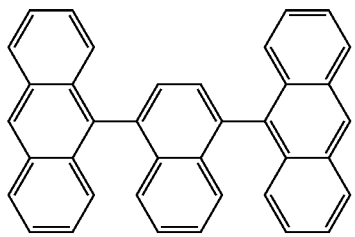 [SMILES: c1ccc2c(-c3ccc(-c4c5ccccc5cc5ccccc45)c4ccccc34)c3ccccc3cc2c1]

Procedure analogous to Example 3a. Instead of 149.0 ml (1.2 mol) of 1,2-dibromobenzene and 98.0 g (308 mmol) of 9,10-anthracenediboronic acid ethylene glycol ester, 28.6 g (100 mmol) of 1,4-dibromonaphthalene and 68.0 g (306 mmol) of 9-anthraceneboronic acid are used. After cooling, the solid is filtered off with suction and washed twice with 500 ml of boiling ethanol each time. Yield: 33.0 g (69 mmol), 68.7% of theory; purity: 98% according to $^1$H-NMR.

b) 1,4-Bis(10-bromoanthracen-9-yl)naphthalene

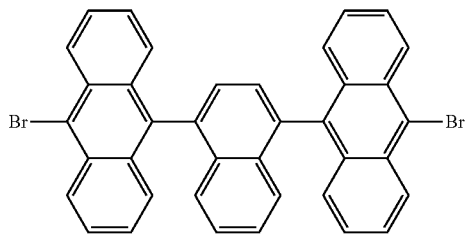 [SMILES: Brc1c2ccccc2c(-c2ccc(-c3c4ccccc4c(Br)c4ccccc34)c3ccccc23)c2ccccc12]

Procedure analogous to Example 4b. Instead of 86.0 g (200 mmol) of 1,2-bis(anthracen-9-yl)benzene and 142.4 g (800 mmol) of N-bromosuccinimide, 96.1 g (200 mmol) of 1,4-bis(anthracen-9-yl)naphthalene and 42.7 g (240 mmol) of N-bromosuccinimide are used. Yield: 109.2 g (171 mmol), 85.5% of theory; purity: 97% according to $^1$H-NMR.

c) 1,4-Bis(anthracen-9-yl-10-boronic acid pinacol ester)naphthalene

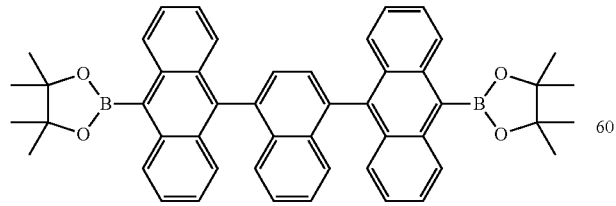

Preparation analogous to Example 3b. Instead of 19.5 g (40 mmol) of 9,10-bis(2-bromophenyl)anthracene, 25.5 g (40 mmol) of 1,4-bis(10-bromoanthracen-9-yl)naphthalene are used. Sublimation at $p=1\times10^{-5}$ mbar, $T=300°$ C. Yield: 12.1 g (16.5 mmol), 41.3% of theory; purity: 99.8% according to $^1$H-NMR.

Example 6

Synthesis of 9,10-bis(naphth-1-yl)anthracene-2,6-bis-(boronic acid pinacol ester)

a) 2,6-Dibromo-9,10-bis(naphth-1-yl)anthracene

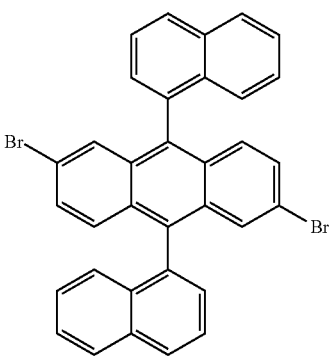 [SMILES: Brc1ccc2c(-c3cccc4ccccc34)c3cc(Br)ccc3c(-c3cccc4ccccc34)c2c1]

The corresponding Grignard reagent is prepared from 30.5 ml (220 mmol) of 1-bromonaphthalene and 5.5 g (225 mmol) of magnesium in 500 ml of THF. 36.6 g (100 mmol) of 2,6-dibromoanthraquinone are added to this Grignard reagent, the mixture is refluxed for 6 h and allowed to cool, 15 ml of acetic acid are added, the mixture is evaporated to dryness, the residue is taken up in 500 ml of DMF, 56.9 g (300 mmol) of tin(II) chloride are added, and the mixture is refluxed for 5 h. After cooling, 200 ml of 2N hydrochloric acid are added, the mixture is stirred for a further 1 h, the solid is filtered off with suction, washed three times with 200 ml of 2N hydrochloric acid each time, three times with 300 ml of water each time, and three times with 200 ml of ethanol each time, dried under reduced pressure and recrystallised once from DMF. Yield: 48.9 g (83 mmol), 83.1% of theory; purity: 98% according to $^1$H-NMR.

b) 9,10-Bis(naphth-1-yl)anthracene-2,6-bis(boronic acid pinacol ester)

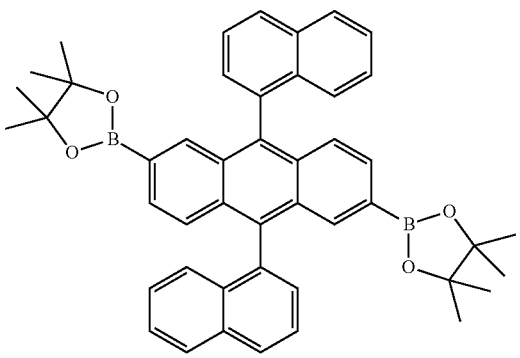

Preparation analogous to Example 3b. Instead of 19.5 g (40 mmol) of 9,10-bis(2-bromophenyl)anthracene, 23.5 g (40 mmol) of 2,6-dibromo-9,10-bis-(naphth-1-yl)anthracene are used. Recrystallisation twice from both toluene and then dioxane. Sublimation at p=1×10⁻⁵ mbar, T=270° C. Yield: 14.6 g (21 mmol), 53.5% of theory; purity: 99.9% according to $^1$H-NMR.

Example 7

Synthesis of 9,10-bis(naphth-1-yl-4-boronic acid pinacol ester)anthracene a) 9,10-Bis(4-bromonaphth-1-yl)anthracene

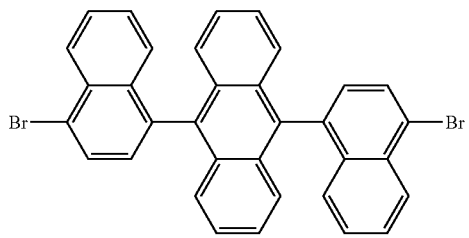 [SMILES: Brc1ccc(-c2c3ccccc3c(-c3ccc(Br)c4ccccc34)c3ccccc23)c2ccccc12]

48.0 ml (120 mmol) of n-butyllithium (2.5M in hexane) are added at −78° C. with vigorous stirring to a solution of 31.9 g (120 mmol) of 1,4-dibromonaphthalene in 1000 ml of THF. The mixture is stirred at −78° C. for 1 h, then allowed to warm to 0° C., 10.4 g (50 mmol) of anthraquinone are added, and the mixture is stirred at 0° C. for a further 3 h. After 15 ml of acetic acid have been added, the mixture is evaporated to dryness, the residue is taken up in 500 ml of DMF, 28.4 g (150 mmol) of tin(II) chloride are added, and the mixture is refluxed for 5 h. After cooling, 200 ml of 2N hydrochloric acid are added, the mixture is stirred for a further 1 h, the solid is filtered off with suction, washed three times with 200 ml of 2N hydrochloric acid each time, three times with 300 ml of water each time and three times with 200 ml of ethanol each time, dried under reduced pressure and recrystallised from NMP. Yield: 25.9 g (44 mmol), 88.0% of theory; purity: 98% according to $^1$H-NMR.

b) 9,10-Bis(4-bromonaphth-1-yl)anthracene

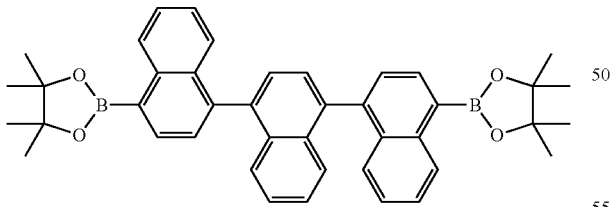

Preparation analogous to Example 3b. Instead of 19.5 g (40 mmol) of 9,10-bis(2-bromophenyl)anthracene, 23.5 g (40 mmol) of 9,10-bis(4-bromonaphth-1-yl)anthracene are used. Owing to the poor solubility of the 9,10-bis(4-bromonaphth-1-yl)anthracene, 200 g of glass beads (diameter 4 mm) are added to the batch, the stirring is carried out using a mechanical paddle stirrer, and the reaction time for the lithiation is increased to 24 h. Recrystallisation four times from dioxane. Sublimation at p=1×10⁻⁵ mbar, T=290° C. Yield: 17.6 g (26 mmol), 64.5% of theory; purity: 99.9% according to $^1$H-NMR.

Example 8

Synthesis of 1,6-bis(2,5-dimethylphenyl)pyrene-3,8-bis(boronic acid pinacol ester)

a) 1,6-Bis(2,5-dimethylphenyl)pyrene

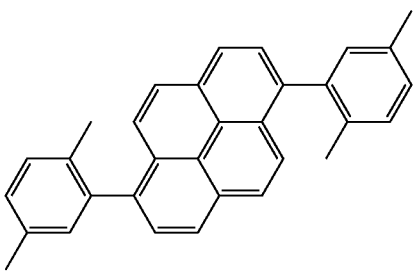 [SMILES: Cc1ccc(C)c(-c2ccc3ccc4c(-c5cc(C)ccc5C)ccc5ccc2c3c54)c1]

7.2 g (20 mmol) of tri-o-tolylphosphine and 740 mg (3.3 mmol) of palladium(II) acetate are added to a vigorously stirred suspension of 76.0 g (211 mmol) of dibromopyrene (isomer mixture), 72.9 g (486 mmol) of 2,5-dimethylphenylboronic acid and 222.4 g (966 mmol) of potassium phosphate monohydrate in a mixture of 500 ml of toluene, 500 ml of dioxane and 100 ml of water, and the mixture is refluxed for 12 h. After cooling to room temperature, the precipitated solid is filtered off with suction, washed with 200 ml of ethanol and dissolved in 500 ml of dichloromethane with warming, the solution is filtered through silica gel, the filtrate is evaporated to 1000 ml under reduced pressure, and 300 ml of ethanol are added. After standing for 2 h, the colourless crystals are filtered off with suction, washed with 100 ml of ethanol and dried under reduced pressure. Yield: 32.5 g (79 mmol), 37.5% of theory; purity 98% according to $^1$H-NMR.

b) 1,6-Bis(2,5-dimethylphenyl)-3,8-dibromopyrene

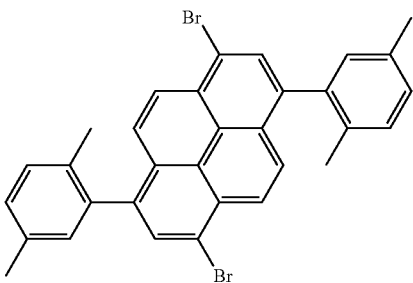 [SMILES: Cc1ccc(C)c(-c2cc(Br)c3ccc4c(-c5cc(C)ccc5C)cc(Br)c5ccc2c3c54)c1]

A suspension of 25.8 g (63 mmol) of 1,6-bis(2,5-dimethylphenyl)pyrene and 24.8 g (139 mmol) of N-bromosuccinimide in 800 ml of THF is stirred at room temperature with exclusion of light for 16 h. The reaction mixture is evaporated to 100 ml under reduced pressure, and 200 ml of ethanol and 200 ml of water are added. The precipitate is filtered off with suction, washed three times with 100 ml of ethanol, dried under reduced pressure and recrystallised twice from chlorobenzene. Yield: 26.0 g (46 mmol), 72.6% of theory; purity 97% according to $^1$H-NMR.

c) 1,6-Bis(2,5-dimethylphenyl)pyrene-3,8-bis(boronic acid pinacol ester)

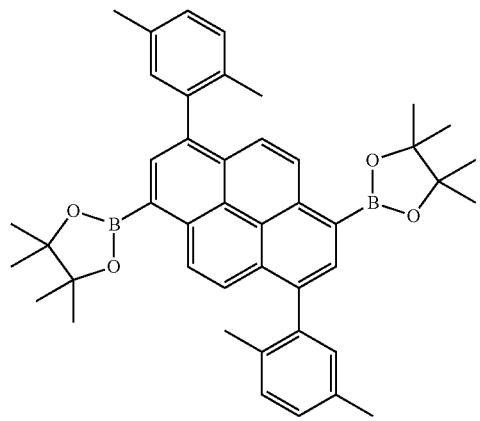

Procedure analogous to Example 3b. Instead of 19.5 g (40 mmol) of 9,10-bis(2-bromophenyl)anthracene, 22.7 g (40 mmol) of 1,6-bis(2,5-dimethylphenyl)-3,8-dibromopyrene are employed. The recrystallisation is carried out from dioxane. Sublimation, $p=1\times10^{-5}$ mbar, $T=290°$ C. Yield: 11.5 g (17 mmol), 43.3% of theory; purity: 99.9% according to $^1$H-NMR.

Example 9

Synthesis of 1,4-bis(anthracen-9-yl-10-boronic acid pyrocatechol ester)naphthalene

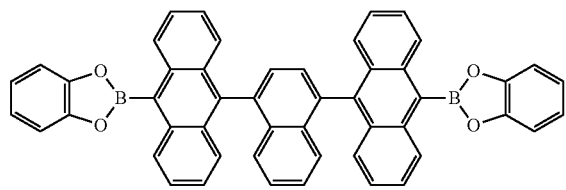 [SMILES: c1ccc2c(c1)OB(c1c3ccccc3c(-c3ccc(-c4c5ccccc5c(B5Oc6ccccc6O5)c5ccccc45)c4ccccc34)c3ccccc13)O2]

Preparation analogous to Example 3b. Instead of 19.5 g (40 mmol) of 9,10-bis(2-bromophenyl)anthracene, 25.5 g (40 mmol) of 1,4-bis(10-bromoanthracen-9-yl)naphthalene are used, and instead of 10.6 g (90 mmol) of pinacol, 9.9 g (90 mmol) of pyrocatechol are used. Sublimation at $p=1\times10^{-5}$ mbar, $T=330°$ C. Yield: 17.7 g (25 mmol), 61.8% of theory; purity: 99.7% according to $^1$H-NMR.

Example 10

Synthesis of 9,10-bis(naphth-1-yl)anthracene-3,8-bis-(boronic acid pyrocatechol ester)

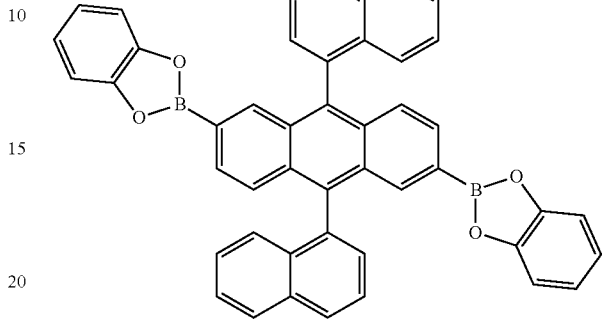

Preparation analogous to Example 3b. Instead of 19.5 g (40 mmol) of 9,10-bis(2-bromophenyl)anthracene, 23.5 g (40 mmol) of 2,6-dibromo-9,10-bis-(naphth-1-yl)anthracene are used, and instead of 10.6 g (90 mmol) of pinacol, 9.9 g (90 mmol) of pyrocatechol are used. Sublimation at $p=1\times10^{-5}$ mbar, $T=305°$ C. Yield: 9.2 g (14 mmol), 34.5% of theory; purity: 99.9% according to $^1$H-NMR.

Example 11

2,4,6-Tris[10-(4-methylnaphth-1-yl)anthracen-9-yl]-cyclotriboroxane

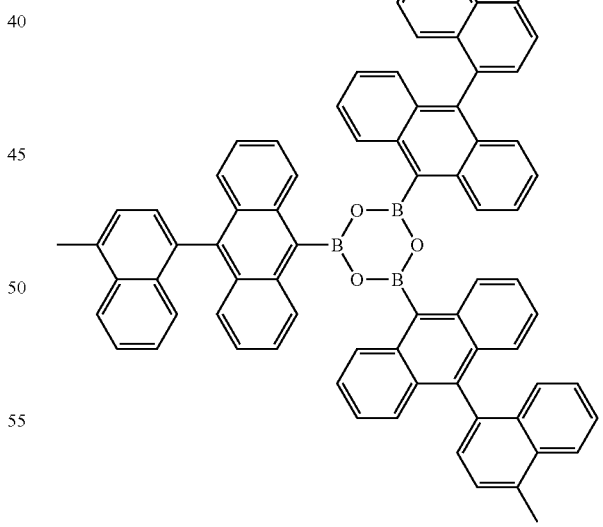

Preparation analogous to Example 2c. After isolation of the boronic acid, it is suspended in 300 ml of acetonitrile and boiled on a water separator for 5 h, during which the azeotrope is removed continuously down to 50 ml. After addition of 300 ml of ethanol and cooling, the deposited crystals are filtered off with suction, recrystallised four times from dioxane and subsequently sublimed ($T=370°$ C., $p=5\times$

Example 12

9,10-Bis(naphth-1-yl)anthracene-3,8-bis(boronic acid hexafluoro-2,3-bis(trifluoromethyl)but-2,3-yl ester)

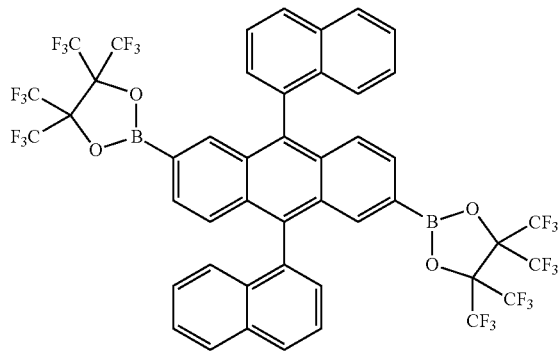 [SMILES: FC(F)(F)C1(C(F)(F)F)OB(c2ccc3c(-c4cccc5ccccc45)c4cc(B5OC(C(F)(F)F)(C(F)(F)F)C(C(F)(F)F)(C(F)(F)F)O5)ccc4c(-c4cccc5ccccc45)c3c2)OC1(C(F)(F)F)C(F)(F)F]

Preparation analogous to Example 3b. Instead of 19.5 g (40 mmol) of 9,10-bis(2-bromophenyl)anthracene, 23.5 g (40 mmol) of 2,6-dibromo-9,10-bis-(naphth-1-yl)anthracene are used. Instead of 10.6 g (90 mmol) of pinacol, 30.1 g (90 mmol) of hexafluoro-2,3-bis(trifluoromethyl)butane-2,3-diol are used. Recrystallisation five times from toluene/acetonitrile. Sublimation at p=1×10$^{-5}$ mbar, T=280° C. Yield: 18.1 g (16 mmol), 40.6% of theory; purity: 99.8% according to $^1$H-NMR.

Example 13

Synthesis of 9,10-bis(naphth-1-yl)anthracene-3,8-bis(2-(3-methyl-2,3-dihydrobenzo-1,3,2-oxazaborole)

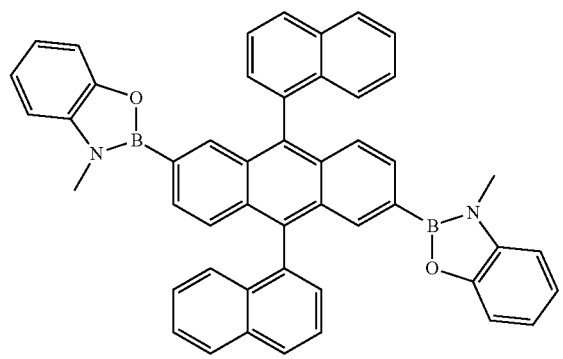 [SMILES: CN1B(c2ccc3c(-c4cccc5ccccc45)c4cc(B5Oc6ccccc6N5C)ccc4c(-c4cccc5ccccc45)c3c2)Oc2ccccc21]

Preparation analogous to Example 3b. Instead of 19.5 g (40 mmol) of 9,10-bis(2-bromophenyl)anthracene, 23.5 g (40 mmol) of 2,6-dibromo-9,10-bis-(naphth-1-yl)anthracene are used. Instead of 10.6 g (90 mmol) of pinacol, 11.1 g (90 mmol) of 2-methylaminophenol are used. Recrystallisation four times from DMF. Sublimation at p=1×10$^{-5}$ mbar, T=280° C. Yield: 14.9 g (21.5 mmol), 53.8% of theory; purity: 99.9% according to $^1$H-NMR.

10$^{-5}$ mbar); yield: 15.8 g (18 mmol), 45.9% of theory; purity: 99.9% according to $^1$H-NMR.

Example 14

Synthesis of tris((4-(2,2-di(4-phenylboronic acid pinacol ester)vinyl)phen-1-yl)amine a) Tris((4-(2,2-di(4-bromophenyl)vinyl)phen-1-yl)amine

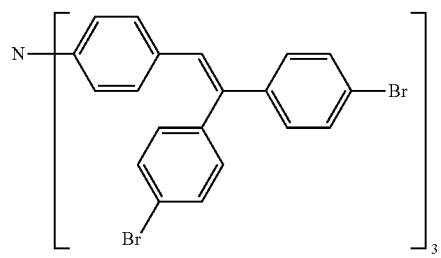

A solution of 184.8 g (400 mmol) of bis(4-bromophenyl)methyl diethylphosphonate in 200 ml of DMF is added to a suspension, cooled to 0° C., of 76.9 g (800 mmol) of sodium tert-butoxide in 1000 ml of anhydrous DMF. After the mixture has been stirred for a further 30 min., a solution of 32.9 g (100 mmol) of tris(4-formyl)amine in 300 ml of DMF is added over the course of 30 min., the mixture is stirred at 0° C. for a further 4 h, then 1000 ml of 1N hydrochloric acid and 500 ml of ethanol are added. The solid is filtered off with suction, washed three times with 300 ml of water and three times with 200 ml of ethanol and dried under reduced pressure. The product is subsequently recrystallised from DMF, filtered off with suction, washed three times with 200 ml of ethanol and dried under reduced pressure. Yield: 109.4 g (87 mmol), 87.3% of theory; purity: 99% according to $^1$H-NMR.

b) Tris((4-(2,2-di(4-phenylboronic acid pinacol ester)vinyl)phen-1-yl)amine

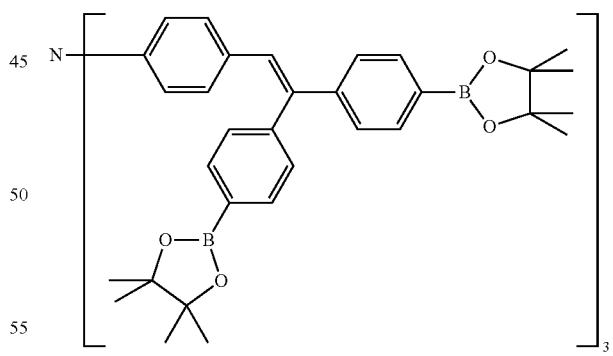

65 ml of n-BuLi (2.5M in hexane) are added to a suspension of 31.3 g (25 mmol) of tris((4-(2,2-di(4-bromophenyl)vinyl)phen-1-yl)amine in 1000 ml of diethyl ether, and the mixture is stirred at room temperature for 6 h. The reaction mixture is subsequently cooled to −78° C., and 44.5 ml (450 mmol) of trimethyl borate are added rapidly with vigorous stirring. After slow warming to room temperature, a mixture of 15 ml of acetic acid and 500 ml of water and then 500 ml of ethyl acetate are added, the mixture is stirred at room temperature for a further 1 h, and the organic phase is separated off, washed twice with 500 ml of water and evaporated under reduced pressure. 500 ml of toluene and 18.9 g (160 mmol) of pinacol are added to the residue, and the mixture is heated on a water separator.

When the separation of water is complete, 400 ml of toluene are distilled off, and 300 ml of ethanol are added. After cooling, the yellow solid is filtered off with suction, recrystallised five times from dioxane/ethanol (1:3, v:v) and sublimed under reduced pressure (p=1×10$^{-5}$ mbar, T=330° C.). Yield: 14.5 g (9 mmol), 37.7% of theory; purity: 99.9% according to $^1$H-NMR.

Example 15

Synthesis of 1,4-bis(4-di(4-phenylboronic acid pinacol ester)aminostyryl)benzene a) 1,4-Bis(4-di(4-bromophenyl)aminostyryl)benzene

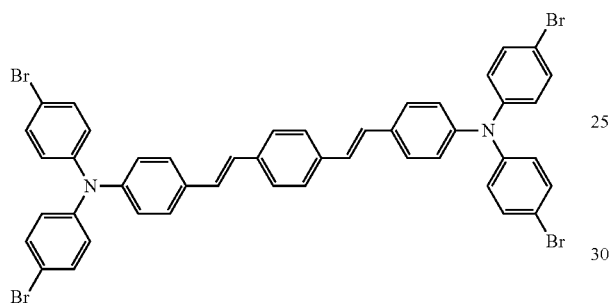

A solution of 37.8 g (100 mmol) of p-xylene diethylphosphonate in 200 ml of DMF is added to a suspension, cooled to 0° C., of 38.5 g (400 mmol) of sodium tert-butoxide in 1000 ml of anhydrous DMF. After the mixture has been stirred for a further 30 min., a solution of 90.5 g (210 mmol) of bis(4-bromophenyl)(4-formylphenyl)amine in 300 ml of DMF is added over the course of 30 min., the mixture is stirred at 0° C. for a further 4 h, and then 500 ml of 1N hydrochloric acid and 300 ml of ethanol are added. The solid is filtered off with suction, washed three times with 300 ml of water and three times with 200 ml of ethanol and dried under reduced pressure. The product is subsequently recrystallised from DMF, filtered off with suction, washed three times with 200 ml of ethanol and dried under reduced pressure. Yield: 86.1 g (92 mmol), 92.3% of theory; purity: 99% according to $^1$H-NMR.

b) 1,4-Bis(4-di(4-phenylboronic acid pinacol ester)aminostyryl)benzene

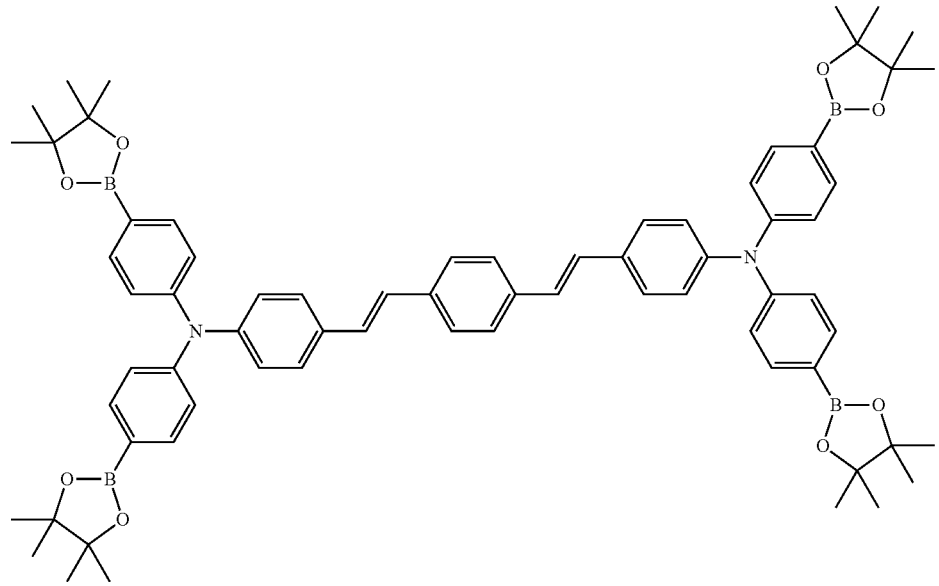

Preparation analogous to Example 14b. Instead of 31.3 g (25 mmol) of tris((4-(2,2-di(4-bromophenyl)vinyl)phen-1-yl)amine, 34.5 g (37 mmol) of 1,4-bis(4-di(4-bromophenyl)aminostyryl)benzene are used. Sublimation, p=1×10⁻⁵ mbar, T=310° C. Yield: 18.9 g (17 mmol), 45.6% of theory; purity: 99.7% according to ¹H-NMR.

Example 16

Synthesis of N,N,N',N'-tetrakis(4-1,3,2-dioxaborolan-2-ylphenyl)biphenyl-4,4'-diamine a) N,N,N',N'-tetra(4-bromophenyl)benzidine

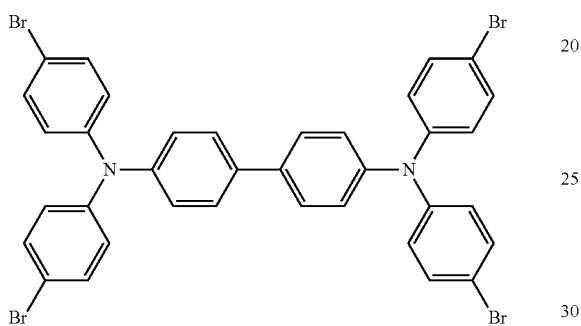

74.8 g (420 mmol) of N-bromosuccinimide are added in portions to a solution of 48.9 g (100 mmol) of N,N,N',N'-tetraphenylbenzidine in 500 ml of THF at 40° C. with vigorous stirring, and the mixture is stirred for 16 h. The mixture is subsequently transferred onto 2000 g of ice, and the resultant precipitate is filtered off with suction, washed three times with 300 ml of water and twice with 200 ml of ethanol and then recrystallised from DMF. Yield: 73.5 g (91 mmol), 91.4% of theory; purity 98% according to ¹H-NMR.

b) N4,N4',N4'',N4'''-tetrakis(4-1,3,2-dioxaborolan-2-ylphenyl)biphenyl-4,4'-diamine

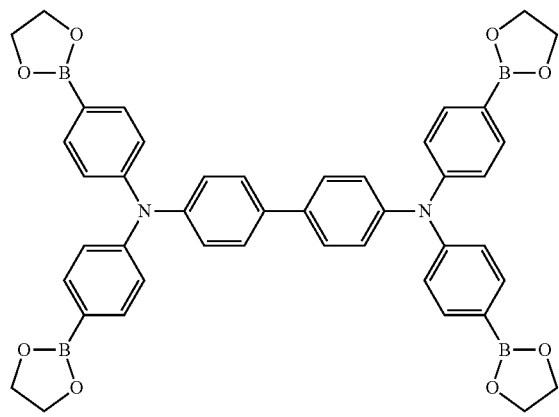 [SMILES: c1cc(N(c2ccc(B3OCCO3)cc2)c2ccc(-c3ccc(N(c4ccc(B5OCCO5)cc4)c4ccc(B5OCCO5)cc4)cc3)cc2)ccc1B1OCCO1]

Preparation analogous to Example 15b. Instead of 34.5 g (37 mmol) of 1,4-bis(4-di(4-bromophenyl)aminostyryl)benzene, 29.8 g (37 mmol) of N,N,N',N'-tetra(4-bromophenyl)benzidine are used, and instead of 18.9 g (160 mmol) of pinacol, 9.0 ml (160 mmol) of ethylene glycol are used. Recrystallisation from toluene. Sublimation, p=1×10⁻⁵ mbar, T=250° C. Yield: 21.3 g (28 mmol), 75.0% of theory; purity: 99.9% according to ¹H-NMR.

Example 17

Synthesis of 2,2'-bis(4-(4,4,5,5-tetramethyl-1,3,2-dioxaborolan-2-yl)phenyl)spiro-9,9'-bifluorene a) 2,2'-Bis(4-bromobenzoyl)spiro-9,9'-bifluorene

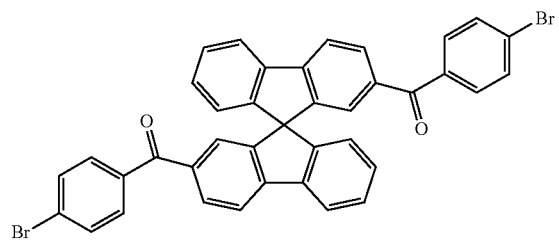 [SMILES: O=C(c1ccc(Br)cc1)c1ccc2c(c1)C1(c3ccccc3-2)c2ccccc2-c2ccc(C(=O)c3ccc(Br)cc3)cc21]

A solution of 24.1 g (110 mmol) of 4-bromobenzoyl chloride in 100 ml of 1,2-dichloroethane is added dropwise to a suspension of 16.0 g (120 mmol) of aluminium chloride in 300 ml of 1,2-dichloroethane. A solution of 15.8 g (50 mmol) of spiro-9,9'-bifluorene in 200 ml of 1,2-dichloroethane is added dropwise to this mixture. The mixture is subsequently stirred at room temperature for a further 4 hours and poured into a mixture of 1000 g of ice and 200 ml of 2N hydrochloric acid with vigorous stirring, and the precipitated solid is filtered off with suction. The solid is washed three times with 500 ml of water and three times with 200 ml of ethanol and dried under reduced pressure. Yield: 29.2 g (43 mmol), 85.6% of theory; purity: 98% according to ¹H-NMR.

b) 2,2'-Bis(4-(4,4,5,5-tetramethyl-1,3,2-dioxaborolan-2-yl)phenyl)-spiro-9,9'-bifluorene

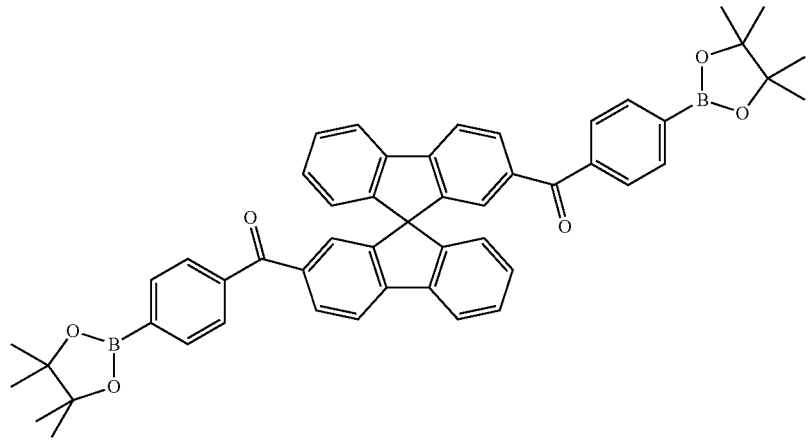

The preparation is carried out by the method of Melaimi et al., *J. Organomet. Chem.* 2004, 689(19), 2988, analogously to the preparation of 2-(4-acetylphenyl)-4,4,5,5-tetramethyl-1,3,2-dioxaborolane. Instead of 4-acetylbromobenzene, 17.1 g (25 mmol) of 2,2'-bis(4-bromobenzoyl)spiro-9,9'-bifluorene are employed. Sublimation, p=1×10$^{-5}$ mbar, T=265° C. Yield: 8.4 g (11 mmol), 43.2% of theory; purity: 99.9% according to $^1$H-NMR.

Example 18

Synthesis of 2-bis(spiro-9,9'-bifluorene)-(4-(4,4,5,5-tetramethyl-1,3,2-dioxaborolan-2-yl)phenyl)phosphine oxide a) 2-Bis(spiro-9,9'-bifluorene)-(4-bromophenyl))phosphine oxide

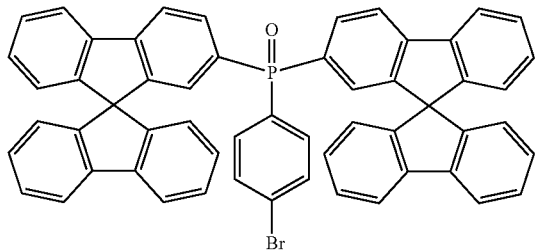 [SMILES: O=P(c1ccc(Br)cc1)(c1ccc2c(c1)C1(c3ccccc3-c3ccccc31)c1ccccc1-2)c1ccc2c(c1)C1(c3ccccc3-c3ccccc31)c1ccccc1-2]

Preparation analogous to WO 05/003253, Example 1. Instead of dichlorophenylphosphine, 41.6 g (120 mmol) of 4-bromophenylphosphorus dibromide are used. Recrystallisation twice from chlorobenzene. Yield: 71.0 g (71 mmol), 71.0% of theory; purity: 98% according to $^1$H-NMR.

b) 2-Bis(spiro-9,9'-bifluorene)-(4-(4,4,5,5-tetramethyl-1,3,2-dioxaborolan-2-yl)phenyl)phosphine oxide

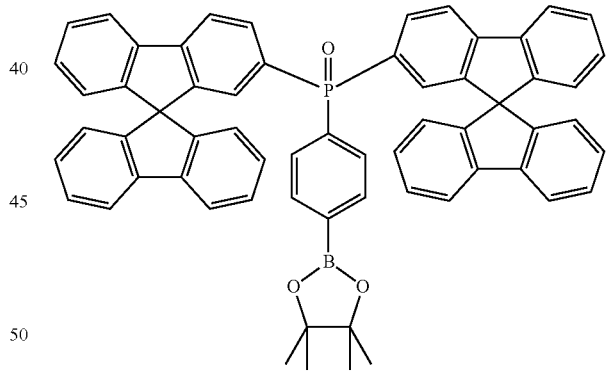

Preparation analogous to Example 17b. Instead of 17.1 g (25 mmol) of 2,2'-bis(4-bromobenzoyl)spiro-9,9'-bifluorene, 20.8 g (25 mmol) of 2-bis-(spiro-9,9'-bifluorene)-(4-bromophenyl))phosphine oxide are employed. Sublimation, p=1×10$^{-5}$ mbar, T=310° C. Yield: 8.0 g (9 mmol), 36.3% of theory; purity: 99.9% according to $^1$H-NMR.

Example 19

Synthesis of 4,4'-bis(4,4'-bis(1,3,2-dioxaborolan-2-yl)-carbazolyl)biphenyl a) 4,4'-Bis(4,4'-bisbromocarbazolyl)biphenyl

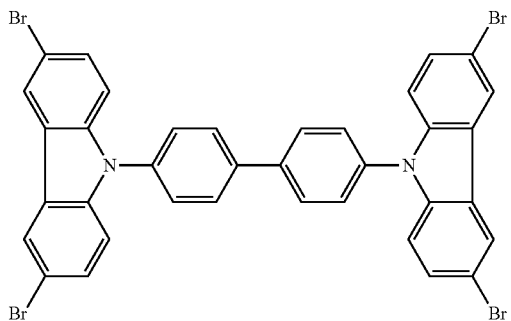 [SMILES: Brc1ccc2c(c1)c1cc(Br)ccc1n2-c1ccc(-c2ccc(-n3c4ccc(Br)cc4c4cc(Br)ccc43)cc2)cc1]

74.8 g (420 mmol) of N-bromosuccinimide are added in portions to a solution of 48.5 g (100 mmol) of biscarbazolylbiphenyl in 1000 ml of THF at 40° C. with vigorous stirring, and the mixture is then stirred for 16 h. The mixture is subsequently transferred onto 2000 g of ice, and the resultant precipitate is filtered off with suction, washed three times with 300 ml of water and twice with 200 ml of ethanol and recrystallised from DMF. Yield: 74.3 g (93 mmol), 92.8% of theory; purity 98% according to $^1$H-NMR.

b) 4,4'-Bis(4,4'-bis(1,3,2-dioxaborolan-2-yl)carbazolyl)biphenyl

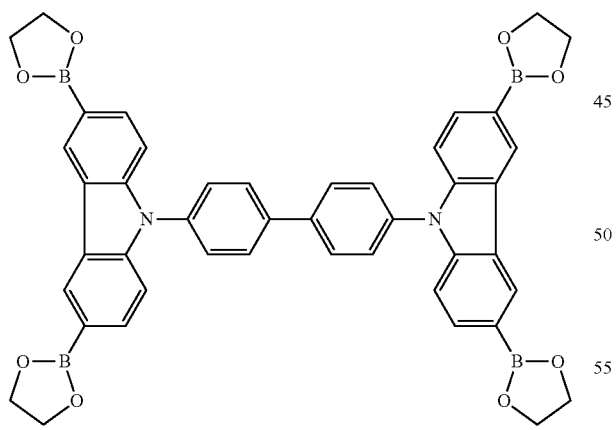

Preparation analogous to Example 16b. Instead of 29.8 g (37 mmol) of N,N,N',N'-tetra(4-bromophenyl)benzidine, 29.6 g (37 mmol) of 4,4'-bis-(4,4'-bisbromocarbazolyl)biphenyl are used, and instead of 18.9 g (160 mmol) of pinacol, 9.0 ml (160 mmol) of ethylene glycol are used. Recrystallisation from dioxane. Sublimation, p=1×10$^{-5}$ mbar, T=270° C. Yield: 21.3 g (28 mmol), 75.3% of theory; purity: 99.9% according to $^1$H-NMR.

Example 20

Synthesis of 1,6-bis((4-methylphenyl)amino)pyrene-3,8-bis(boronic acid pinacol ester)

a) 1,6-Bis((4-methylphenyl)amino)pyrene

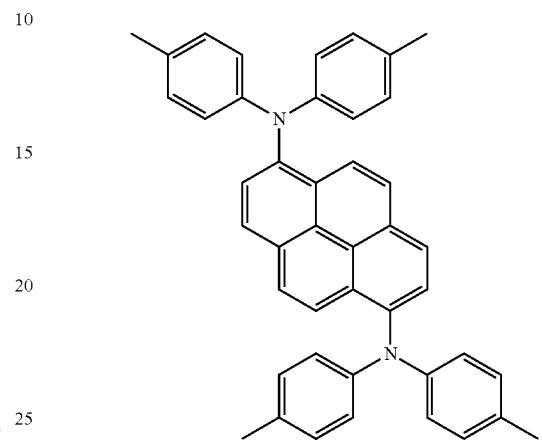

1.05 ml (5.2 mmol) of di-tert-butylphosphine chloride and then 898 mg (4.0 mmol) of palladium(II) acetate are added to a vigorously stirred suspension of 76.0 g (211 mmol) of dibromopyrene (isomer mixture), 94.7 g (480 mmol) of bis(4-methylphenyl)amine and 50.0 g (520 mmol) of sodium tert-butoxide in 1000 ml of toluene, and the mixture is refluxed for 5 h. After cooling to room temperature, 1000 ml of water are added, and the precipitated solid is filtered off with suction, washed with 200 ml of ethanol and dried under reduced pressure. Recrystallisation, three times from DMF. Yield: 41.4 g (70 mmol), 33.1% of theory; purity 99% according to $^1$H-NMR.

b) 1,6-Bis((4-methylphenyl)amino)-3,8-dibromopyrene

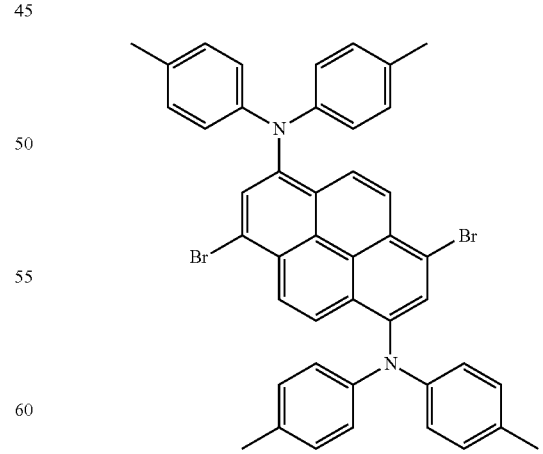

Preparation analogous to Example 8b. Instead of 25.8 g (63 mmol) of 1,6-bis(2,5-dimethylphenyl)pyrene, 29.6 g (50 mmol) of 1,6-bis((4-methyl-phenyl)amino)pyrene are used, and instead of 24.8 g (139 mmol) of N-bromosuccinimide, 19.6 g (110 mmol) of N-bromosuccinimide are used. Yield: 27.4 g (36.5 mmol), 73.0% of theory; purity 99% according to $^1$H-NMR.

c) 1,6-Bis((4-methylphenyl)amino)pyrene-3,8-bis (boronic acid pinacol ester)

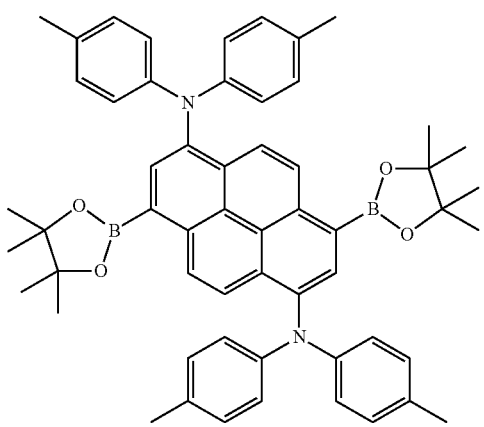

Procedure analogous to Example 3b. Instead of 19.5 g (40 mmol) of 9,10-bis(2-bromophenyl)anthracene, 30.0 g (40 mmol) of 1,6-bis((4-methyl-phenyl)amino)-3,8-dibromopyrene are employed. The recrystallisation is carried out from chlorobenzene. Sublimation, p=1×10$^{-5}$ mbar, T=285° C. Yield: 13.8 g (16 mmol), 40.8% of theory; purity: 99.9% according to $^1$H-NMR.

Example 21

Synthesis of 9,10-bis((bis-4-(4,4,5,5-tetramethyl-1,3,2-dioxaborolan-2-yl)phenyl)amino)anthracene a) 9,10-Bis(diphenylamino)anthracene

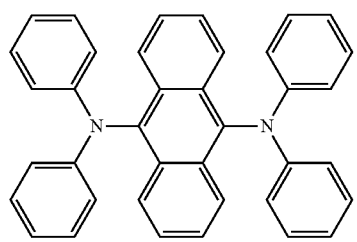 [SMILES: c1ccc(N(c2ccccc2)c2c3ccccc3c(N(c3ccccc3)c3ccccc3)c3ccccc23)cc1]

Preparation analogous to Example 20a. Instead of 76.0 g (211 mmol) of dibromopyrene (isomer mixture) and 94.7 g (480 mmol) of bis(4-methyl-phenyl)amine, 70.9 g (211 mmol) of 9,10-dibromoanthracene and 81.2 g (480 mmol) of diphenylamine are used. Yield: 86.2 g (168 mmol), 79.7% of theory; purity 99% according to $^1$H-NMR.

b) 9,10-Bis-N,N-(di(4-bromophenyl)amino)anthracene

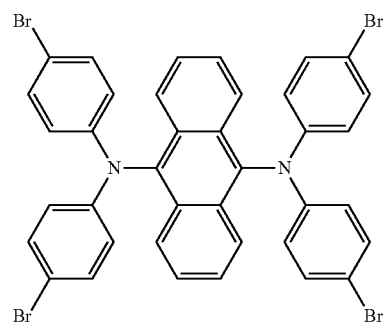 [SMILES: Brc1ccc(N(c2ccc(Br)cc2)c2c3ccccc3c(N(c3ccc(Br)cc3)c3ccc(Br)cc3)c3ccccc23)cc1]

Preparation analogous to Example 16a. Instead of 48.9 g (100 mmol) of N,N,N',N'-tetraphenylbenzidine, 51.3 g (100 mmol) of 9,10-bis(diphenylamino)anthracene are used. Yield: 70.8 g (85 mmol), 85.5% of theory; purity 98% according to $^1$H-NMR.

c) 9,10-Bis((bis-4-(4,4,5,5-tetramethyl-1,3,2-dioxaborolan-2-yl)-phenyl)amino)anthracene

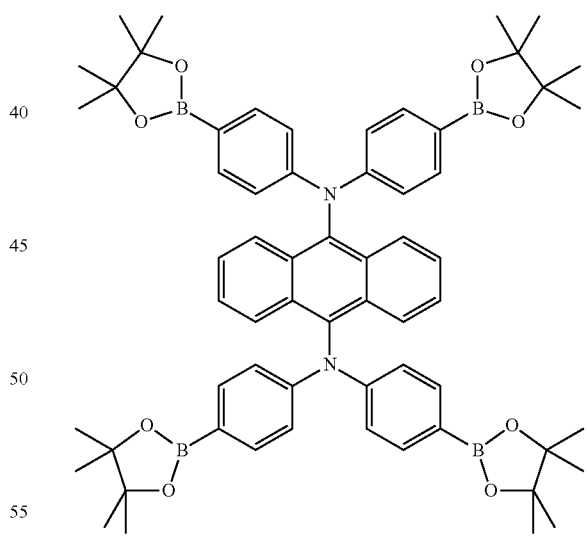

Preparation analogous to Example 3b. Instead of 19.5 g (40 mmol) of 9,10-bis(2-bromophenyl)anthracene, 16.6 g (20 mmol) of 9,10-bis(di(4-bromo-phenyl)amino)anthracene are used. The recrystallisation is carried out from chlorobenzene. Sublimation, p=1×10$^{-5}$ mbar, T=285° C. Yield: 9.9 g (9.7 mmol), 48.7% of theory; purity 99.8% according to $^1$H-NMR.

Example 22

Synthesis of fac-tris[2-(2-pyridinyl-κN)(5-(4,4,5,5-tetramethyl-1,3,2-dioxaborolan-2-yl)phenyl)-κC]-iridium(III)

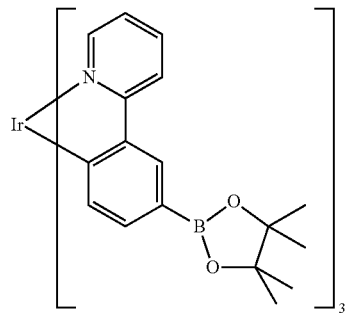

The preparation is carried out by the method of Broutin et al., *Org. Lett.* 2004, 6(24), 4419 analogously to the general preparation procedure for phenylboronates. 892 mg (1 mmol) of fac-tris[2-(2-pyridinyl-κN)(5-bromo-phenyl)-κC]iridium(III) in 10 ml of dioxane and 1.3 g (10 mmol) of pinacolborane are employed, and the reaction time is 16 h. Chromatographic purification on deactivated silica gel (5% of triethylamine), eluent dichloromethane:n-hexane (1:10, v:v). Sublimation, p=1×10$^{-5}$ mbar, T=295° C. Yield: 325 mg (315 μmol), 31.5% of theory; purity: 99.9% according to $^1$H-NMR.

Example 23

Synthesis of fac-tris[2-(2-pyridinyl-κN)(4-fluoro-5-(4,4,5,5-tetramethyl-1,3,2-dioxaborolan-2-yl)phenyl)-κC]iridium(III)

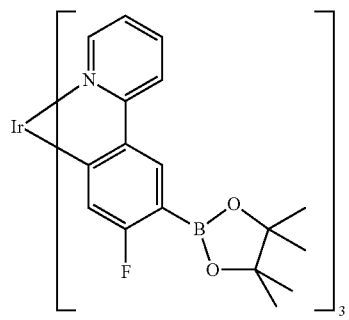

The preparation is carried out by the method of Broutin et al., *Org. Lett.* 2004, 6(24), 4419 analogously to the general preparation procedure for phenylboronates. 946 mg (1 mmol) of fac-tris[2-(2-pyridinyl-κN)(4-fluoro-5-bromophenyl)-κC]iridium(III) in 10 ml of dioxane and 1.3 g (10 mmol) of pinacolborane are employed, and the reaction time is 16 h. Chromatographic purification on deactivated silica gel (5% of triethylamine), eluent dichloromethane:n-hexane (1:10, v:v). Sublimation, p=1×10$^{-5}$ mbar, T=280° C. Yield: 324 mg (298 μmol), 29.8% of theory; purity: 99.8% according to $^1$H-NMR.

Example 24

Synthesis of fac-tris[2-(1-isoquinolinyl-κN)(5-(4,4,5,5-tetramethyl-1,3,2-dioxaborolan-2-yl)phenyl)-κC]-iridium(III)

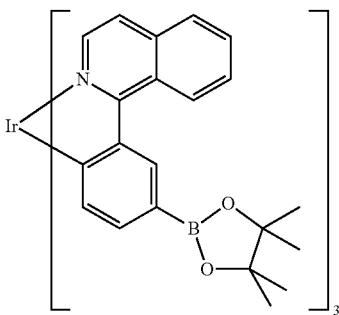

The preparation is carried out by the method of Broutin et al., *Org. Lett.* 2004, 6(24), 4419 analogously to the general preparation procedure for phenylboronates. 1042 mg (1 mmol) of fac-tris[2-(1-isoquinolinyl-κN)(5-bromophenyl)-κC]iridium(III) in 10 ml of dioxane and 1.3 g (10 mmol) of pinacolborane are employed, and the reaction time is 16 h. Chromatographic purification on deactivated silica gel (5% of triethylamine), eluent dichloromethane:n-hexane (1:10, v:v). Sublimation, p=1×10$^{-5}$ mbar, T=340° C. Yield: 485 mg (410 μmol), 41.0% of theory; purity: 99.9% according to $^1$H-NMR.

Example 25

Production of OLEDs Comprising the Materials According to the Invention According to Examples 1 to 13

OLEDs are produced by a general process in accordance with WO 04/058911, which is adapted in individual cases to the particular circumstances (for example layer-thickness variation in order to achieve optimum efficiency or colour).

The results for various OLEDs are presented in Examples 26 to 39 below. The basic structure and the materials used (apart from the emitting layer) are identical in the examples for better comparability. OLEDs having the following structure are produced analogously to the above-mentioned general process:

| | |
|---|---|
| Hole-injection layer (HIL) | 20 nm PEDOT (spin-coated from water; from H. C. Starck, Goslar, Germany; poly(3,4-ethylenedioxy-2,5-thiophene)) |
| Hole-transport layer (HTL) | 30 nm 4,4',4''-tris(N-1-naphthyl-N-phenyl-amino)triphenylamine (abbreviated to NaphDATA, purchased from SynTec) |
| Hole-transport layer (HTL) | 30 nm NPB (N-naphthyl-N-phenyl-4,4'-diaminobiphenyl) |
| Emission layer (EML) | 30 nm layer of the host materials in accordance with Examples 1 to 13 (see table), doped with 5% of tris[4-(2,2-diphenyl-vinyl)-phenyl]amine as dopant (abbreviated to D1, vapour-deposited, synthesised in accordance with WO 06/000388) |

-continued

| | |
|---|---|
| OR: | as comparative example 30 nm 9,10-bis(1-naphthylanthracene) as host material (abbreviated to H), doped with 5% of tris[4-(2,2-diphenylvinyl)phenyl]amine as dopant (abbreviated to D1) |
| Electron conductor (ETC) | 20 nm AlQ$_3$ (purchased from SynTec, tris(quinolinato)aluminium(III)) |
| Cathode | 1 nm LiF, 150 nm Al on top |

These OLEDs are characterised by standard methods; the electroluminescence spectra, the efficiency (measured in cd/A), the power efficiency (measured in lm/W) as a function of the brightness, calculated from current/voltage/brightness characteristic lines (IUL characteristic lines), are determined for this purpose.

Table 1 shows the results for some OLEDs (Examples 26 to 39).

The host material employed for the comparative example is 9,10-bis(1-naphthyl)anthracene; the dopant employed in all examples is D1. Both are prepared as follows:

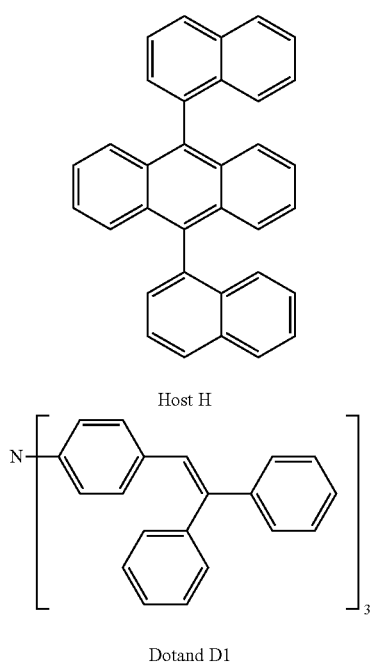

Host H

Dotand D1

As can be seen from the examples in Table 1, OLEDs comprising the host materials according to Examples 1 to 13 according to the invention exhibit lower operating voltages. Besides significantly improved power efficiencies, equivalent to lower power consumption for the same operating brightnesses, this also results in improved lifetimes.

TABLE 1

| Example | EML | Max. efficiency (cd/A) | Voltage (V) at 1000 cd/m² | CIE |
|---|---|---|---|---|
| Example 26 (Comparison) | Host H Dopant D1 | 7.9 | 6.6 | x = 0.17; y = 0.31 |
| Example 27 | Host acc. to Ex. 1 Dopant D1 | 8.2 | 5.3 | x = 0.16; y = 0.28 |
| Example 28 | Host acc. to Ex. 2 Dopant D1 | 8.3 | 5.2 | x = 0.16; y = 0.29 |
| Example 29 | Host acc. to Ex. 3 Dopant D1 | 8.2 | 5.3 | x = 0.16; y = 0.29 |
| Example 30 | Host acc. to Ex. 4 Dopant D1 | 8.0 | 5.4 | x = 0.16; y = 0.30 |
| Example 31 | Host acc. to Ex. 5 Dopant D1 | 8.5 | 5.0 | x = 0.16; y = 0.28 |
| Example 32 | Host acc. to Ex. 6 Dopant D1 | 8.6 | 4.9 | x = 0.16; y = 0.29 |
| Example 33 | Host acc. to Ex. 7 Dopant D1 | 8.7 | 4.7 | x = 0.15; y = 0.27 |
| Example 34 | Host acc. to Ex. 8 Dopant D1 | 8.5 | 4.9 | x = 0.16; y = 0.28 |
| Example 35 | Host acc. to Ex. 9 Dopant D1 | 8.3 | 5.0 | x = 0.17; y = 0.29 |
| Example 36 | Host acc. to Ex. 10 Dopant D1 | 8.4 | 5.1 | x = 0.16; y = 0.29 |
| Example 37 | Host acc. to Ex. 11 Dopant D1 | 8.7 | 5.4 | x = 0.15; y = 0.27 |
| Example 38 | Host acc. to Ex. 12 Dopant D1 | 8.6 | 5.5 | x = 0.16; y = 0.28 |
| Example 39 | Host acc. to Ex. 13 Dopant D1 | 7.9 | 5.3 | x = 0.16; y = 0.29 |

Example 40

Production of OLEDs Comprising the Host Materials According to Examples 5 to 8 or Host H and the Emitters According to Examples 14 and 15

The results for various OLEDs are presented in Examples 41 to 51 below. The basic structure and the materials used (apart from the emitting layer) are identical in the examples for better comparability. OLEDs having the following structure are produced analogously to the above-mentioned general process:

| | |
|---|---|
| Hole-injection layer (HIL) | 20 nm PEDOT (spin-coated from water; from H. C. Starck, Goslar, Germany; poly(3,4-ethylenedioxy-2,5-thiophene)) |
| Hole-transport layer (HTL) | 30 nm 4,4',4''-tris(N-1-naphthyl-N-phenyl-amino)triphenylamine (abbreviated to NaphDATA, purchased from SynTec) |
| Hole-transport layer (HTL) | 30 nm NPB (N-naphthyl-N-phenyl-4,4'-diaminobiphenyl) |
| Emission layer (EML) | 30 nm layer of the host materials in accordance with Examples 5, 6, 7, 8 (see table), doped with 5% of dopant according to Example 14 or 15 |
| OR: | as comparative example 9,10-bis(1-naphthyl-anthracene) as host material (abbreviated to H), doped with 5% of tris[4-(2,2-diphenyl-vinyl)phenyl]amine as dopant (abbreviated to D1), vapour-deposited, synthesised in accordance with WO 06/000388 or doped with 5% of 1,4-bis(4-di(3-methyl-phenyl)aminostyryl)benzene as dopant (abbreviated to D2), vapour-deposited, synthesised in accordance with JP 06001973 |
| Electron conductor (ETC) | 20 nm AlQ$_3$ (purchased from SynTec, tris(quinolinato)aluminium(III)) |
| Cathode | 1 nm LiF, 150 nm Al on top |

These OLEDs are characterised by standard methods; the electroluminescence spectra, the efficiency (measured in cd/A), the power efficiency (measured in lm/W) as a function of the brightness, calculated from current/voltage/ brightness characteristic lines (IUL characteristic lines), are determined for this purpose.

Table 2 shows the results for some OLEDs (Examples 41 to 51). The host material for the comparative examples is 9,10-bis(1-naphthyl)anthracene (see above), and the dopants employed for the comparative examples are D1 (see above) and D2.

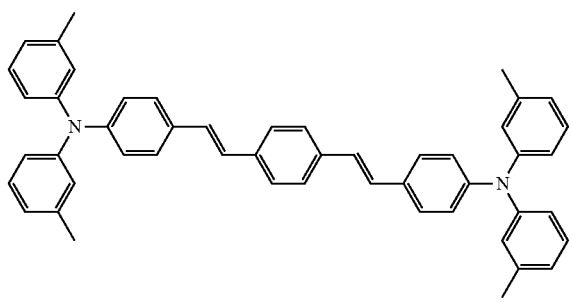

Dotand D2

As can be seen from the examples in Table 2, OLEDs comprising the host materials according to the invention exhibit significantly improved efficiencies at the same time as comparable colour coordinates and improved lifetimes.

In addition, the considerably improved thermal stability of the dopant according to Example 15 according to the invention compared with dopant D2, which is structurally analogous, but is not substituted by 4,4,5,5-tetramethyl-1,3, 2-dioxaborolan-2-yl groups, should again be pointed out at this point. This improved stability is of crucial importance, in particular on industrial use, since dopants in industrial use must have lifetimes of several days to weeks at high temperatures.

TABLE 2

| Example | EML | Max. efficiency (cd/A) | Voltage (V) at 1000 cd/m² | CIE |
| --- | --- | --- | --- | --- |
| Example 41 (comparison) | Host H Dopant D | 7.9 | 6.6 | x = 0.17; y = 0.31 |
| Example 42 | Host H Dopant acc. to Ex. 14 | 9.8 | 5.1 | x = 0.19; y = 0.31 |
| Example 43 | Host H Dopant acc. to Ex. 15 | 12.3 | 5.0 | x = 0.21; y = 0.33 |
| Example 44 | Host acc. to Ex. 5 Dopant acc. to Ex. 14 | 10.2 | 5.0 | x = 0.17; y = 0.31 |
| Example 45 | Host acc. to Ex. 6 Dopant acc. to Ex. 14 | 10.3 | 4.9 | x = 0.18; y = 0.32 |
| Example 46 | Host acc. to Ex. 7 Dopant acc. to Ex. 14 | 9.9 | 5.2 | x = 0.18; y = 0.32 |
| Example 47 | Host acc. to Ex. 8 Dopant acc. to Ex. 14 | 10.6 | 4.9 | x = 0.18; y = 0.32 |
| Example 48 | Host acc. to Ex. 5 Dopant acc. to Ex. 15 | 13.2 | 5.0 | x = 0.19; y = 0.32 |
| Example 49 | Host acc. to Ex. 6 Dopant acc. to Ex. 15 | 13.0 | 4.9 | x = 0.19; y = 0.32 |
| Example 50 | Host acc. to Ex. 7 Dopant acc. to Ex. 15 | 12.9 | 5.2 | x = 0.19; y = 0.32 |
| Example 51 | Host acc. to Ex. 8 Dopant acc. to Ex. 15 | 12.7 | 4.9 | x = 0.19; y = 0.32 |

Example 52

Production of OLEDs Comprising the Hole-Transport Material According to Example 16

The results for various OLEDs are presented in Examples 53 and 54 below. The basic structure and the materials used (apart from the emitting layer) are identical in the examples for better comparability. OLEDs having the following structure are produced analogously to the above-mentioned general process:

| | |
| --- | --- |
| Hole-injection layer (HIL) | 20 nm PEDOT (spin-coated from water; from H. C. Starck, Goslar, Germany; poly(3,4-ethylenedioxy-2,5-thiophene)) |
| Hole-transport layer (HTL) OR: | 30 nm layer of the hole-transport material according to Example 16 as comparative example 30 nm layer of N,N,N',N'-tetraphenyl-[1,1'-biphenyl]-4,4'-diamine (abbreviated to TAD; purchased from SynTec) |
| Hole-transport layer (HTL) | 30 nm NPB (N-naphthyl-N-phenyl-4,4'-diaminobiphenyl) |
| Emission layer (EML) | 30 nm layer of the host material according to Example 8 (see table), doped with 5% of dopant according to Example 14 |
| Electron conductor (ETC) | 20 nm AlQ₃ (purchased from SynTec, tris-(quinolinato)aluminium(III)) |
| Cathode | 1 nm LiF, 150 nm Al on top |

These OLEDs are characterised by standard methods; the electroluminescence spectra, the efficiency (measured in cd/A), the power efficiency (measured in lm/W) as a function of the brightness, calculated from current/voltage/ brightness characteristic lines (IUL characteristic lines), are determined for this purpose.

Table 3 shows the results for two OLEDs (Examples 53 and 54). As can be seen from the examples in Table 3, OLEDs comprising the hole-transport material according to Example 16 according to the invention exhibit significantly improved efficiencies at the same time as comparable colour coordinates and improved lifetimes.

TABLE 3

| Example | HTL | Max. efficiency (cd/A) | Voltage (V) at 1000 cd/m² | CIE |
| --- | --- | --- | --- | --- |
| Example 53 (comparison) | TAD | 9.0 | 5.6 | x = 0.19; y = 0.33 |
| Example 54 | HTL acc. to Ex. 16 | 10.8 | 4.7 | x = 0.18; y = 0.32 |

Example 55

Production of OLEDs Comprising Matrix Materials According to Examples 17, 18 and 19 and Emitters According to Examples 22, 23 and 24

OLEDs are produced by a general process in accordance with WO 04/93207, which is adapted in individual cases to the particular circumstances (for example layer-thickness variation in order to achieve optimum efficiency or colour).

The results for various OLEDs are compared here. The basic structure, such as the materials used, degree of doping and their layer thicknesses, is identical in the example experiments for better comparability. Only the host material in the emitter layer is exchanged, and the examples are carried out with different triplet emitters.

The first example describes a comparison standard in accordance with the prior art in which the emitter layer consists of the matrix material CBP.

Furthermore, OLEDs comprising an emitter layer consisting of the matrix materials according to Examples 17, 18 and 19 according to the invention are described.

Green- and red-emitting OLEDs having the following structure are produced analogously to the above-mentioned general process:

| | |
|---|---|
| PEDOT | 60 nm (spin-coated from water; purchased from H. C. Starck; poly [3,4-ethylenedioxy-2,5-thiophene]) |
| NaphDATA | 20 nm (vapour-deposited; NaphDATA purchased from SynTec; 4,4',4''-tris(N-1-naphthyl-N-phenylamino)triphenylamine |
| S-TAD | 20 nm (vapour-deposited; S-TAD prepared in accordance with WO99/12888; 2,2',7,7'-tetrakis(diphenylamino)spirobifluorene) |
| Emitter layer: | 20 nm of the matrix material according to Example 17, 18 or 19 in each case doped with 10% of E1 (synthesised in accordance with WO 04/085449) or E2 (synthesised in accordance with US 2003/0068526) |
| OR: | 20 nm of the matrix material according to Example 17, 18 or 19 in each case doped with 10% of the emitter in accordance with Example 22, 23 or 24 |
| OR: | as comparative example 20 nm CBP (vapour-deposited; CBP purchased from ALDRICH and purified further, finally sublimed twice; 4,4'-bis(N-carbazolyl)biphenyl) (comparison standard), doped with 10% of E1 (synthesised in accordance with WO 04/085449) or E2 (synthesised in accordance with US 2003/0068526) |
| Bathocuproin (BCP) | 10 nm (vapour-deposited; BCP purchased from ABCR, used as supplied; 2,9-dimethyl-4,7-diphenyl-1,10-phenanthroline); not used in all examples |
| AlQ$_3$ | 10 nm (vapour-deposited; AlQ$_3$ purchased from SynTec; tris(quinolinolato)aluminium(III)), not used in all examples |
| Ba/Al | 3 nm Ba, 150 nm Al on top as cathode |

These OLEDs are characterised by standard methods; the electroluminescence spectra, the efficiency (measured in cd/A), the power efficiency (measured in lm/W) as a function of the brightness, calculated from current/voltage/brightness characteristic lines (IUL characteristic lines), and the lifetime are determined for this purpose. The lifetime is defined as the time after which the initial brightness of 1000 cd/m$^2$ has dropped to half. For an overview, the triplet emitters used and the host materials used are shown below:

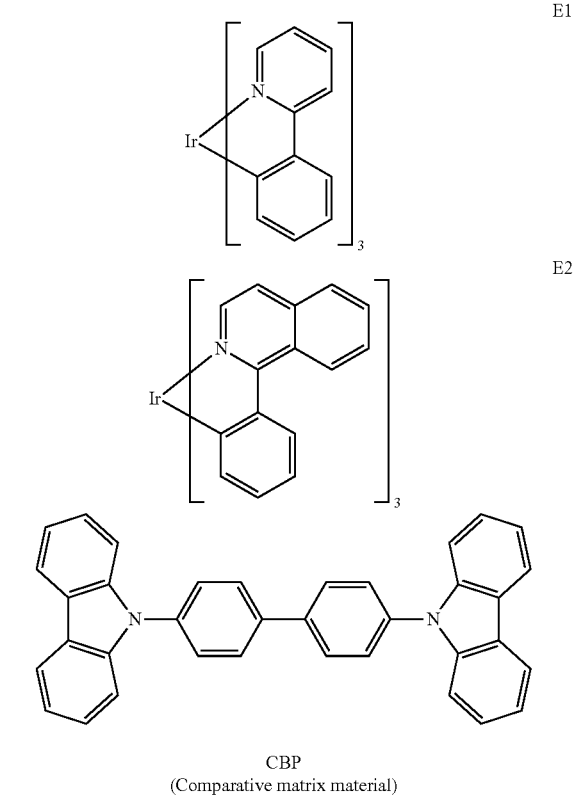

E1

E2

CBP
(Comparative matrix material)

TABLE 4

| Experiment | EML | HBL | ETL | Max. efficiency (cd/A) | Max. power efficiency (lm/W) | x, y (CIE) | Lifetime (h) at 1000 cd/cm$^2$ |
|---|---|---|---|---|---|---|---|
| Example 56 (comparison) | CBP E1 | BCP (10 nm) | AlQ$_3$ (10 nm) | 25.0 | 12.2 | 0.33, 0.61 | 400 |
| Example 57 | Matrix acc. to Ex. 17 E1 | BCP (10 nm) | AlQ$_3$ (10 nm) | 32.2 | 26.7 | 0.32, 0.60 | 1050 |
| Example 58 | Matrix acc. to Ex. 18 E1 | BCP (10 nm) | AlQ$_3$ (10 nm) | 43.0 | 36.5 | 0.32, 0.60 | 1200 |
| Example 59 | Matrix acc. to Ex. 19 E1 | BCP (10 nm) | AlQ$_3$ (10 nm) | 33.9 | 17.4 | 0.31, 0.61 | 650 |
| Example 60 (Comparison) | CBP Emitter acc. to Ex. 22 | BCP (10 nm) | AlQ$_3$ (10 nm) | 20.9 | 17.2 | 0.31, 0.63 | 900 |
| Example 61 | Matrix acc. to Ex. 17 Emitter acc. to Ex. 22 | BCP (10 nm) | AlQ$_3$ (10 nm) | 34.8 | 28.8 | 0.30, 0.62 | 2200 |
| Example 62 | Matrix acc. to Ex. 18 Emitter acc. to Ex. 22 | BCP (10 nm) | AlQ$_3$ (10 nm) | 47.2 | 36.8 | 0.30, 0.62 | 2600 |
| Example 63 | Matrix acc. to Ex. 19 Emitter acc. to Ex. 22 | BCP (10 nm) | AlQ$_3$ (10 nm) | 35.0 | 19.1 | 0.30, 0.61 | 1750 |
| Example 64 | Matrix acc. to Ex. 17 Emitter acc. to Ex. 22 | | | 42.0 | 34.6 | 0.31, 0.62 | 2000 |
| Example 65 | Matrix acc. to Ex. 18 Emitter acc. to Ex. 22 | | | 56.4 | 46.8 | 0.31, 0.62 | 2100 |
| Example 66 | Matrix acc. to Ex. 18 Emitter acc. to Ex. 22 | | | 59.2 | 51.9 | 0.30, 0.61 | 1550 |

TABLE 4-continued

| Experiment | EML | HBL | ETL | Max. efficiency (cd/A) | Max. power efficiency (lm/W) | x, y (CIE) | Lifetime (h) at 1000 cd/cm$^2$ |
|---|---|---|---|---|---|---|---|
| Example 67 | Matrix acc. to Ex. 18 Emitter acc. to Ex. 23 | | | 45.2 | 33.2 | 0.38, 0.52 | 1550 |
| Example 68 (Comparison) | CBP E2 | | | 6.5 | 4.8 | 0.68, 0.32 | 5000 (extrapolated) |
| Example 69 | Matrix acc. to Ex. 17 E2 | | | 7.7 | 6.7 | 0.69, 0.31 | 25000 (extrapolated) |
| Example 70 | Matrix acc. to Ex. 18 E2 | | | 8.1 | 7.6 | 0.68, 0.32 | 27000 (extrapolated) |
| Example 71 | Matrix acc. to Ex. 19 E2 | | | 7.2 | 5.4 | 0.68, 0.32 | 8000 (extrapolated) |
| Example 72 | CBP Emitter acc. to Ex. 24 | | | 13.4 | 9.0 | 0.66, 0.34 | 11000 (extrapolated) |
| Example 73 | Matrix acc. to Ex. 17 Emitter acc. to Ex. 24 | | | 14.3 | 11.5 | 0.67, 0.33 | 32000 (extrapolated) |
| Example 74 | Matrix acc. to Ex. 18 Emitter acc. to Ex. 24 | | | 14.7 | 12.2 | 0.66, 0.34 | 27000 (extrapolated) |
| Example 75 | Matrix acc. to Ex. 19 Emitter acc. to Ex. 24 | | | 14.1 | 10.1 | 0.66, 0.34 | 15000 (extrapolated) |

Electroluminescence Spectra:

The OLEDs, both from the comparative examples and also the OLEDs comprising the matrices and emitters according to the invention, exhibit comparable colour coordinates, where the emitters according to Examples 22, 23 and 24 according to the invention, which carry 4,4,5,5-tetramethyl-1,3,2-dioxaborolan-2-yl groups, have somewhat hypsochromically shifted emission.

Efficiency:

OLEDs produced using the matrix materials according to Example 17, 18 or 19 according to the invention and comprising the emitters according to Examples 22, 23 and 24 exhibit both significantly better photometric efficiency and also better power efficiencies compared with the matrix material in accordance with the prior art. This applies, in particular, to the power efficiency, which is crucial from a technical point of view, due to the lower operating voltages on use of the matrix materials according to the invention.

Lifetime:

The lifetime achieved on use of the matrix materials 17, 18 and 19 according to the invention and emitters 22, 23 and 24 considerably exceeds that of the comparative examples comprising the matrix material CBP.

Layer Simplification:

As can be seen from Examples 64, 65 and 66, it is possible using the matrix materials according to the invention to produce OLEDs which comprise neither a hole-blocking layer nor an electron-conductor layer without thereby impairing the overall electro-optical property profile. This is a considerable advantage from a production point of view.

Thermal Stability:

The emitters according to Examples 22, 23 and 24 have significantly higher thermal stability compared with the compounds which are structural analogous, but are not substituted by boronic acid ester groups. This improved stability is of crucial importance, in particular on industrial use, since dopants in industrial use must have lifetimes of from several days to weeks at high temperatures.

Example 76

Production of OLEDs Comprising the Electron-Transport Materials According to Examples 17, 18 and 19

OLEDs are produced by a general process in accordance with WO 04/058911, which is adapted in individual cases to the particular circumstances (for example layer-thickness variation in order to achieve optimum efficiency or colour).

The results for various OLEDs are presented in Examples 77 to 79 below. The basic structure and the materials used (apart from the electron-transport layer) are identical in the examples for better comparability. OLEDs having the following structure are produced analogously to the above-mentioned general process:

| | |
|---|---|
| Hole-injection layer (HIL) | 20 nm PEDOT (spin-coated from water; from H. C. Starck, Goslar, Germany; poly(3,4-ethylenedioxy-2,5-thiophene)) |
| Hole-transport layer (HTL) | 30 nm 4,4',4''-tris(N-1-naphthyl-N-phenyl-amino)triphenylamine (abbreviated to NaphDATA, purchased from SynTec) |
| Hole-transport layer (HTL) | 30 nm NPB (N-naphthyl-N-phenyl-4,4'-diaminobiphenyl) |
| Emission layer (EML) | 30 nm doped layer of 9,10-bis(1-naphthyl-anthracene) as host material (abbreviated to H), doped with 5% of tris[4-(2,2-diphenyl-vinyl)phenyl]amine as dopant (abbreviated to D1), vapour-deposited |
| Electron conductor (ETC) OR: | 20 nm of the electron conductor according to Example 17 or 18 as comparative example 20 nm AlQ$_3$ (purchased from SynTec, tris(quinolinato)-aluminium(III)) |
| Cathode | 1 nm LiF, 150 nm Al on top |

These OLEDs are characterised by standard methods; the electroluminescence spectra, the efficiency (measured in cd/A), the power efficiency (measured in lm/W) as a function of the brightness, calculated from current/voltage/brightness characteristic lines (IUL characteristic lines), are determined for this purpose.

Table 5 shows the results for some OLEDs (Examples 79 and 80) in which the electron-transport layer (ETL) consists of the compounds 17 or 18 according to the invention. The comparative material used in the comparative example is AlQ$_3$ in accordance with the prior art.

As can be seen from Examples 77 to 79 in Table 5, OLED devices comprising the electron-transport materials according to Examples 17 and 18 according to the invention exhibit a significantly lower operating voltage at 1000 cd/m$^2$, which is evident from better power efficiencies.

TABLE 5

| Example | ETL | Max. efficiency (cd/A) | Voltage (V) at 1000 cd/m² | CIE |
|---|---|---|---|---|
| Example 77 (comparison) | AlQ₃ | 7.9 | 6.6 | x = 0.17; y = 0.31 |
| Example 78 | ETL acc. to Ex. 17 | 8.0 | 5.1 | x = 0.16; y = 0.31 |
| Example 79 | ETL acc. to Ex. 18 | 8.0 | 5.0 | x = 0.16; y = 0.31 |

Example 80

Production of OLEDs Comprising the Emitter Materials According to Examples 20 and 21

OLEDs are produced by a general process in accordance with WO 04/058911, which is adapted in individual cases to the particular circumstances (for example layer-thickness variation in order to achieve optimum efficiency or colour).

The results for various OLEDs are presented in Examples 81 and 82 below. The basic structure and the materials used (apart from the electron-transport layer) are identical in the examples for better comparability. OLEDs having the following structure are produced analogously to the above-mentioned general process:

| | |
|---|---|
| Hole-injection layer (HIL) | 20 nm PEDOT (spin-coated from water; from H. C. Starck, Goslar, Germany; poly(3,4-ethylenedioxy-2,5-thiophene)) |
| Hole-transport layer (HTL) | 30 nm 4,4',4''-tris(N-1-naphthyl-N-phenyl-amino)triphenylamine (abbreviated to NaphDATA, purchased from SynTec) |
| Hole-transport layer (HTL) | 30 nm NPB (N-naphthyl-N-phenyl-4,4'-diaminobiphenyl) |
| Emission layer (EML) | 30 nm doped layer of 9,10-bis(1-naphthyl-anthracene) as host material (abbreviated to H), doped with 5% of the emitter materials according to Example 20 or 21 |
| Electron conductor (ETC) | 20 nm AlQ₃ (purchased from SynTec, tris-(quinolinato)aluminium(III)) |
| Cathode | 1 nm LiF, 150 nm Al on top |

These OLEDs are characterised by standard methods; the electroluminescence spectra, the efficiency (measured in cd/A), the power efficiency (measured in lm/W) as a function of the brightness, calculated from current/voltage/brightness characteristic lines (IUL characteristic lines), are determined for this purpose.

Table 6 shows the results for some OLEDs (Examples 81 and 82) in which the emitter materials consist of compounds 20 and 21 according to the invention.

As can be seen from Examples 81 and 82 in Table 6, OLED devices comprising the emitter materials according to Examples 20 and 21 according to the invention exhibit efficient green emission.

TABLE 6

| Example | EML | Max. efficiency (cd/A) | Voltage (V) at 1000 cd/m² | CIE |
|---|---|---|---|---|
| Example 81 | Emitter acc. to Ex. 20 | 21.0 | 5.1 | x = 0.27; y = 0.62 |
| Example 82 | Emitter acc. to Ex. 21 | 18.2 | 5.0 | x = 0.24; y = 0.58 |

Example 83

Sublimation Temperatures

In Table 7 below, the sublimation temperatures (at a pressure of $1 \times 10^{-5}$ mbar) of some compounds which are described in the preceding examples are compared with the sublimation temperatures of compounds which have the same basic structure, but are not substituted by boronic acid esters. It can be seen from the examples given that the sublimation temperature of the corresponding boronic esters is in all cases lower than that of the unsubstituted compounds. This is a considerable industrial advantage since temperature-sensitive parts of the vapour-deposition apparatus, such as, for example, shadow masks, are thus only heated to a smaller extent.

It is furthermore evident that some of the compounds which, as unsubstituted compound, exhibit decomposition during sublimation can be sublimed without decomposition if they are substituted by boronic acid ester groups. This is a considerable industrial advantage.

TABLE 7

| Compound | T$_{sublimation}$ | Comparison | T$_{sublimation}$ |
|---|---|---|---|
| from Example 6 | 270° C. stable | standard OLED material | 360° C. stable |

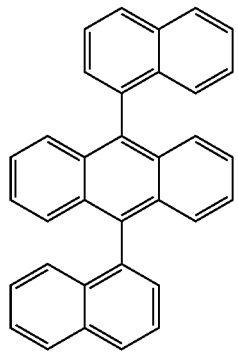

TABLE 7-continued
| Compound | T$_{sublimation}$ | Comparison | T$_{sublimation}$ |
|---|---|---|---|
| from Example 7 | 290° C. stable | standard OLED material 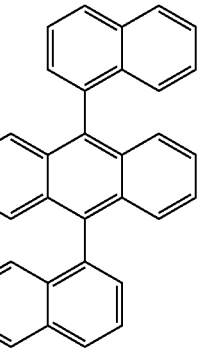 | 360° C. stable |
| from Example 14 | 300° C. stable | WO 06/000388 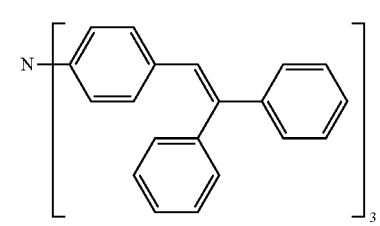 | 315° C. stable |
| from Example 17 | 265° C. stable | WO 04/093207 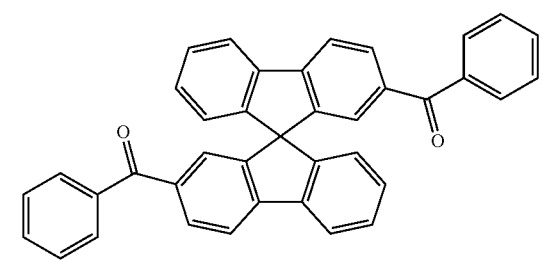 | 290° C. stable |
| from Example 18 | 310° C. stable | WO 05/003253 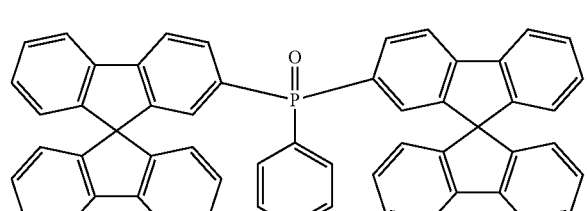 | 385° C. stable |

TABLE 7-continued
| Compound | T$_{sublimation}$ | Comparison | T$_{sublimation}$ |
|---|---|---|---|
| from Example 22 | 295° C. stable | standard OLED material 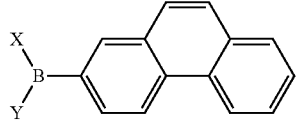 | 340° C. little decomposition |
| from Example 24 | 340° C. stable | WO 05/033244 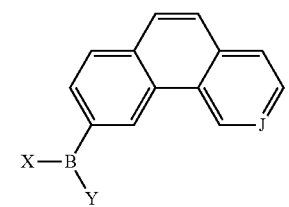 | 385° C. strong decomposition |
The invention claimed is:
1. A compound of formulae (9), (10), (11), (12), (13), (14), (15), (16), (17), (18), (19), (20), (21), (22), (23), (24), (25), or (26)
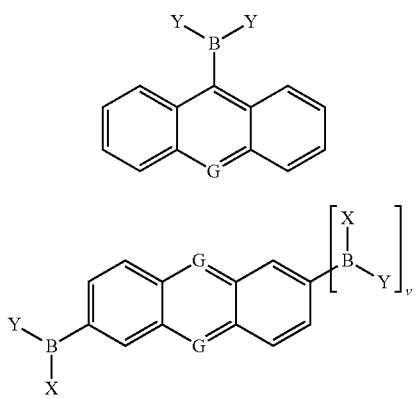
Formula (9)
Formula (9a)
Formula (10)
Formula (11)
Formula (12)
Formula (13)
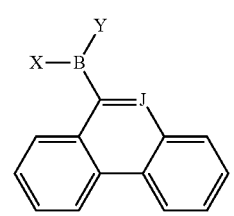
Formula (14)
Formula (15)

Formula (16)

Formula (17)

Formula (18)

Formula (19)

Formula (20)

Formula (21)

Formula (22)

Formula (23)

Formula (24)

Formula (25)

Formula (26)

wherein said compounds of formulae (9), (10), (11), (12), (13), (14), (15), (16), (17), (18), (19), (20), (21), (22), (23), (24), (25), or (26) are optionally substituted by $R^1$, wherein B is a boron atom;

X is, identically or differently on each occurrence, $OR^2$, $SR^2$, $N(R^2)_2$, $NHR^2$, or $OBAr_2$;

Y is, identically or differently on each occurrence, Ar or X;

$R^1$ is, identically or differently on each occurrence, F, Cl, Br, I, CN, a straight-chain alkyl, alkoxy, or thioalkoxy chain having up to 40 C atoms optionally substituted by $R^3$, or a branched or cyclic alkyl, alkoxy, or thioalkoxy chain having 3 to 40 C atoms, optionally substituted by $R^3$, wherein one or more non-adjacent C atoms of said straight-chain, branched, or cyclic alkyl, alkoxy, or thioalkoxy chain is optionally replaced by N—$R^3$, O, S, CO, O—CO—O, CO—O, —$CR^3$=$CR^3$—, or —C≡C—and wherein one or more H atoms of said straight-chain, branched, or cyclic alkyl, alkoxy, or thioalkoxy chain is optionally replaced by F, Cl, Br, I, CN, or an aromatic or heteroaromatic ring system having 5 to 40 aromatic ring atoms optionally substituted by one or more $R^3$, or a combination of two, three or four of these systems; and wherein two or more $R^1$ optionally define a mono- or polycyclic, aliphatic, or aromatic ring system;

$R^3$ is, identically or differently on each occurrence, H or an aliphatic or aromatic hydrocarbon radical having up to 20 C atoms.

$Ar^1$ is, identically or differently on each occurrence, an aryl or heteroaryl group having 5 to 40 aromatic ring atoms, which may be substituted by $R^1$;

G is, identically or differently on each occurrence, C—H, C—$R^1$, C—BXY, or N;

J is, identically or differently on each occurrence, C—H, C—$R^1$, or C—BXY;

v is, identically or differently on each occurrence, 0 or 1;

$R^2$ is, identically or differently on each occurrence, a straight-chain alkyl chain having up to 40 C atoms optionally substituted by $R^3$ or a branched or cyclic alkyl chain having 3 to 40 C atoms optionally substituted by $R^3$; wherein one or more non-adjacent C atoms is optionally replaced by N—R³, O, S, CO, O—CO—O, CO—O, —CR³=CR³—, or —C≡C—, with the proviso that a heteroatom is not bonded directly to the oxygen or sulfur or nitrogen of the group X or Y; and wherein one or more H atoms is optionally replaced by F, Cl, Br, I, CN, or an aromatic or heteroaromatic ring system having 5 to 40 aromatic ring atoms optionally substituted by one or more radicals R³, or a combination of two, three or four of these systems; and wherein two or more radicals R² optionally define a mono- or polycyclic, aliphatic, or aromatic ring system;

with the proviso when X is OR² and Y is OR² in formulae (24) and (25), the two R² define an aromatic ring system, and with the proviso that the following compounds are excluded:

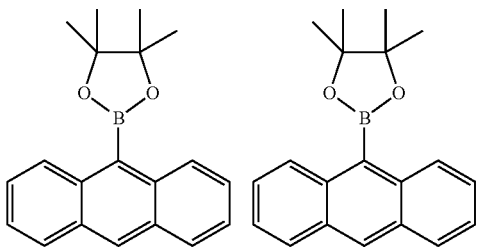

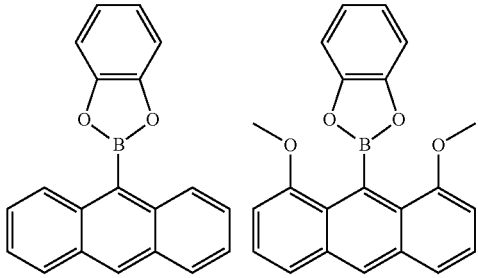

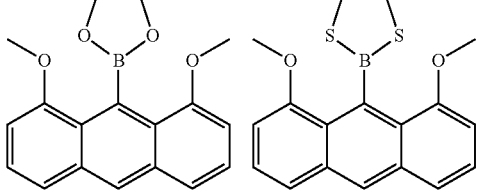

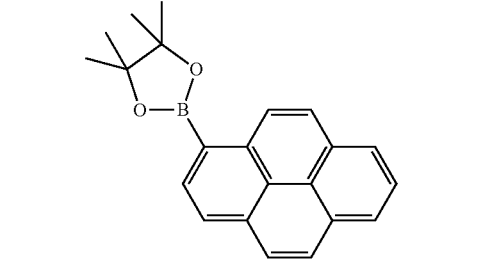

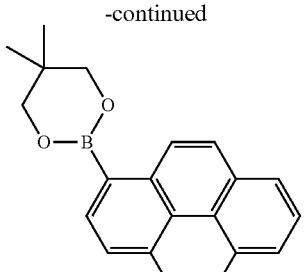

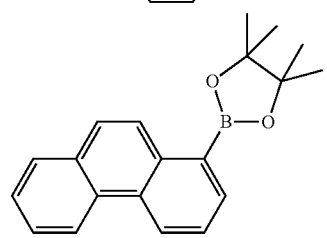

2. A compound of formulae (27), (27a), or (28)

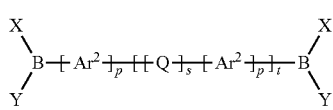
Formula (27)

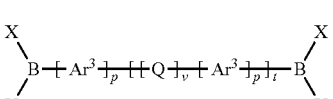
Formula (27a)

Formula (28)

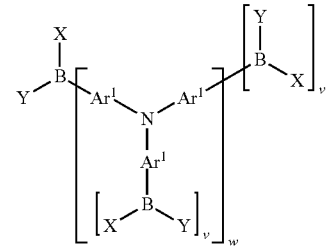

wherein
B is a boron atom;
X is, identically or differently on each occurrence, OR², SR², N(R²)₂, NHR², or OBAr₂;
Y is, identically or differently on each occurrence, Ar or X;
Ar is, identically or differently on each occurrence, an aromatic or heteroaromatic ring system having 5 to 40 aromatic ring atoms optionally substituted by one or more R¹;
Ar¹ is, identically or differently on each occurrence, an aryl or heteroaryl group having 5 to 40 aromatic ring atoms, which may be substituted by R¹;
R¹ is, identically or differently on each occurrence, F, Cl, Br, I, CN, a straight-chain alkyl, alkoxy, or thioalkoxy chain having up to 40 C atoms optionally substituted by $R^3$, or a branched or cyclic alkyl, alkoxy, or thioalkoxy chain having 3 to 40 C atoms, optionally substituted by $R^3$, wherein one or more non-adjacent C atoms of said straight-chain, branched, or cyclic alkyl, alkoxy, or thioalkoxy chain is optionally replaced by N—$R^3$, O, S, CO, O—CO—O, CO—O, —$CR^3$=$CR^3$—, or —C≡C—and wherein one or more H atoms of said straight-chain, branched, or cyclic alkyl, alkoxy, or thioalkoxy chain is optionally replaced by F, Cl, Br, I, CN, or an aromatic or heteroaromatic ring system having 5 to 40 aromatic ring atoms optionally substituted by one or more $R^3$, or a combination of two, three or four of these systems; and wherein two or more $R^1$ optionally define a mono- or polycyclic, aliphatic, or aromatic ring system;

$R^3$ is, identically or differently on each occurrence, H or an aliphatic or aromatic hydrocarbon radical having up to 20 C atoms.

v is, identically or differently on each occurrence, 0 or 1;

Z is, identically or differently on each occurrence, O, S, $NR^2$, or NH;

L is, identically or differently on each occurrence, an organic group having 4 to 60 C atoms, to which at least four groups Z are bonded in such a way that they are able, with the boron atom, to form a cyclic system;

$R^2$ is, identically or differently on each occurrence, a straight-chain alkyl chain having up to 40 C atoms optionally substituted by $R^3$ or a branched or cyclic alkyl chain having 3 to 40 C atoms optionally substituted by $R^3$; wherein one or more non-adjacent C atoms is optionally replaced by N—$R^3$, O, S, CO, O—CO—O, CO—O, —$CR^3$=$CR^3$—, or —C≡C—with the proviso that a heteroatom is not bonded directly to the oxygen or sulfur or nitrogen of the group X or Y; and wherein one or more H atoms is optionally replaced by F, Cl, Br, I, CN, or an aromatic or heteroaromatic ring system having 5 to 40 aromatic ring atoms optionally substituted by one or more radicals $R^3$, or a combination of two, three or four of these systems; and wherein two or more radicals $R^2$ optionally define a mono- or polycyclic, aliphatic, or aromatic ring system;

$Ar^2$ is, identically or differently on each occurence, a fused aryl or heteroaryl group having 9 to 20 C atoms;

$Ar^3$ is, identically or differently on each occurence, a flourene or spirobiflourene group optionally substituted by $R^1$;

Q is, identically or differently on each occurrence, a divalent unit selected from Ar, O, S, SO, $SO_2$, Se, SeO, $SeO_2$, Te, TeO, $TeO_2$, NAr, PAr, P(=O)Ar, AsAr, As(=O)Ar, SbAr, Sb(=O)Ar, $C(R^1)_2$, C=O, $Si(R^1)_2$, and O—BAr—O;

p is, identically or differently on each occurrence, 1, 2, 3, 4, 5, or 6;

is 0 or 1;

t is 1, 2, 3, 4, or 5;

w is, identically or differently on each occurrence, 1, 2, 3, 4, 5, or 6;

with the proviso that $Ar^2$ in formula (27) is not naphthyl on each occurrence if all p equal 1 and at the same time s equals 0 and t equals 1, and with the proviso that boronic acid esters of formula (28) formed with pinacol, 1,2-ethanediol, 2,2-dimethyl-1,3-propanediol, 2,3-butanediol, and isopropanol are excluded.

\* \* \* \* \*